(12) United States Patent
Shankaranarayana et al.

(10) Patent No.: US 12,144,925 B2
(45) Date of Patent: *Nov. 19, 2024

(54) REMOTE VENTILATOR ADJUSTMENT

(71) Applicant: Covidien LP, Mansfield, MA (US)

(72) Inventors: Kiran Shankaranarayana, San Diego, CA (US); David M. Lafreniere, Fallbrook, CA (US); Ryan Gleim, Vista, CA (US); Mehran Shafiei, Vista, CA (US); Ankit B. Patel, San Diego, CA (US); Eon Joo Son, La Jolla, CA (US)

(73) Assignee: Covidien LP, Mansfield, MA (US)

( * ) Notice: Subject to any disclaimer, the term of this patent is extended or adjusted under 35 U.S.C. 154(b) by 66 days.

This patent is subject to a terminal disclaimer.

(21) Appl. No.: 18/185,767

(22) Filed: Mar. 17, 2023

(65) Prior Publication Data

US 2023/0211099 A1    Jul. 6, 2023

Related U.S. Application Data

(63) Continuation of application No. 17/241,638, filed on Apr. 27, 2021, now Pat. No. 11,672,934.
(Continued)

(51) Int. Cl.
*A61M 16/00* (2006.01)
*G06F 3/04817* (2022.01)
(Continued)

(52) U.S. Cl.
CPC ...... *A61M 16/024* (2017.08); *A61M 16/0063* (2014.02); *A61M 16/022* (2017.08);
(Continued)

(58) Field of Classification Search
CPC ............ A61M 16/024; A61M 16/0063; A61M 16/022; A61M 2205/3553;
(Continued)

(56) References Cited

U.S. PATENT DOCUMENTS

| | | |
|---|---|---|
| 3,577,984 A | 5/1971 | Levy et al. |
| 3,659,590 A | 5/1972 | Jones et al. |

(Continued)

FOREIGN PATENT DOCUMENTS

| | | |
|---|---|---|
| EP | 0414777 | 3/1991 |
| EP | 1421966 | 5/2004 |

(Continued)

OTHER PUBLICATIONS

US 7,284,551 B2, 10/2007, Jones et al. (withdrawn)
(Continued)

*Primary Examiner* — Ankur Jain

(57) ABSTRACT

Aspects of the technology include methods and systems for performing remote adjustments to a ventilator with a remote device. A remote device may include an interactive display including a remote position indicator. The remote position indicator may be associated or correlated with a local ventilator position indicator. A selection and/or adjustment at the remote device (or an activation at the remote device) at the interactive display may result in a selection, adjustment, or activation at the ventilator. Information may be transmitted to the ventilator from the remote device to remotely adjust the ventilator. Additionally or alternatively, the remote device may additionally display a view of, or replicate, some or all portions of the ventilator display.

20 Claims, 23 Drawing Sheets

Related U.S. Application Data

(60) Provisional application No. 63/050,214, filed on Jul. 10, 2020, provisional application No. 63/023,343, filed on May 12, 2020.

(51) Int. Cl.
*G06F 3/0482* (2013.01)
*G06F 3/04847* (2022.01)
*G16H 40/67* (2018.01)
*H04N 7/18* (2006.01)
*H04W 84/18* (2009.01)

(52) U.S. Cl.
CPC ........ *G06F 3/04817* (2013.01); *G06F 3/0482* (2013.01); *G06F 3/04847* (2013.01); *G16H 40/67* (2018.01); *H04N 7/183* (2013.01); *A61M 2205/3553* (2013.01); *A61M 2205/3584* (2013.01); *A61M 2205/505* (2013.01); *A61M 2205/52* (2013.01); *H04W 84/18* (2013.01)

(58) Field of Classification Search
CPC .... A61M 2205/3584; A61M 2205/505; A61M 2205/52; A61M 16/06; A61M 16/08; A61M 2205/14; G06F 3/04817; G06F 3/0482; G06F 3/04847; G16H 40/67; G16H 20/40; H04N 7/183; H04W 84/18
See application file for complete search history.

(56) References Cited

U.S. PATENT DOCUMENTS

| | | |
|---|---|---|
| 3,871,371 A | 3/1975 | Weigl |
| 3,940,742 A | 2/1976 | Hudspeth et al. |
| 3,961,624 A | 6/1976 | Weigl |
| 3,961,627 A | 6/1976 | Ernst et al. |
| 3,977,394 A | 8/1976 | Jones et al. |
| 3,991,304 A | 11/1976 | Hillsman |
| 3,996,928 A | 12/1976 | Marx |
| 4,034,743 A | 7/1977 | Greenwood et al. |
| 4,036,217 A | 7/1977 | Ito et al. |
| 4,053,951 A | 10/1977 | Hudspeth et al. |
| 4,090,513 A | 5/1978 | Togawa |
| 4,112,931 A | 9/1978 | Burns |
| 4,187,842 A | 2/1980 | Schreiber |
| 4,215,409 A | 7/1980 | Strowe |
| 4,241,739 A | 12/1980 | Elson |
| 4,258,718 A | 3/1981 | Goldman |
| 4,296,756 A | 10/1981 | Dunning et al. |
| 4,308,872 A | 1/1982 | Watson et al. |
| 4,323,064 A | 4/1982 | Hoenig et al. |
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,917,108 A | 4/1990 | Mault |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,137,026 A | 8/1992 | Waterson et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,261,397 A | 11/1993 | Grunstein |
| 5,261,415 A | 11/1993 | Dussault |
| 5,277,195 A | 1/1994 | Williams |
| 5,279,304 A | 1/1994 | Einhorn et al. |
| 5,293,875 A | 3/1994 | Stone |
| 5,303,698 A | 4/1994 | Tobia et al. |
| 5,303,699 A | 4/1994 | Bonassa et al. |
| 5,307,795 A | 5/1994 | Whitwam et al. |
| 5,319,355 A | 6/1994 | Russek |
| 5,333,106 A | 7/1994 | Lanpher et al. |
| 5,339,825 A | 8/1994 | McNaughton et al. |
| 5,355,893 A | 10/1994 | Mick et al. |
| 5,357,975 A | 10/1994 | Kraemer et al. |
| 5,363,842 A | 11/1994 | Mishelevich et al. |
| 5,365,922 A | 11/1994 | Raemer |
| 5,373,851 A | 12/1994 | Reinhold, Jr. et al. |
| 5,383,470 A | 1/1995 | Kolbly |
| 5,402,796 A | 4/1995 | Packer et al. |
| 5,404,871 A | 4/1995 | Goodman et al. |
| 5,442,940 A | 8/1995 | Secker et al. |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,517,985 A | 5/1996 | Kirk et al. |
| 5,518,002 A | 5/1996 | Wolf et al. |
| 5,534,851 A | 7/1996 | Russek |
| 5,537,992 A | 7/1996 | Bjoernstijerna et al. |
| 5,542,410 A | 8/1996 | Goodman et al. |
| 5,549,117 A | 8/1996 | Tacklind et al. |
| 5,553,620 A | 9/1996 | Snider et al. |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,579,775 A | 12/1996 | Dempsey et al. |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall et al. |
| 5,611,335 A | 3/1997 | Makhoul et al. |
| 5,626,144 A | 5/1997 | Tacklind et al. |
| 5,632,281 A | 5/1997 | Rayburn |
| 5,634,461 A | 6/1997 | Faithfull et al. |
| 5,634,471 A | 6/1997 | Fairfax et al. |
| 5,642,735 A | 7/1997 | Kolbly |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,669,379 A | 9/1997 | Somerson et al. |

(56) References Cited

U.S. PATENT DOCUMENTS

| | | |
|---|---|---|
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,687,717 A | 11/1997 | Halpern et al. |
| 5,692,497 A | 12/1997 | Schnitzer et al. |
| 5,704,346 A | 1/1998 | Inoue |
| 5,704,366 A | 1/1998 | Tacklind et al. |
| 5,704,367 A | 1/1998 | Ishikawa et al. |
| 5,706,801 A | 1/1998 | Remes et al. |
| 5,724,990 A | 3/1998 | Ogino |
| 5,730,140 A | 3/1998 | Fitch |
| 5,730,145 A | 3/1998 | Defares et al. |
| 5,735,287 A | 4/1998 | Thomson |
| 5,738,092 A | 4/1998 | Mock et al. |
| 5,740,792 A | 4/1998 | Ashley et al. |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,778,874 A | 7/1998 | Maguire et al. |
| 5,794,612 A | 8/1998 | Wachter et al. |
| 5,800,361 A | 9/1998 | Rayburn |
| 5,806,514 A | 9/1998 | Mock et al. |
| 5,809,997 A | 9/1998 | Wolf |
| 5,813,397 A | 9/1998 | Goodman et al. |
| 5,819,723 A | 10/1998 | Joseph |
| 5,822,715 A | 10/1998 | Worthington et al. |
| 5,826,570 A | 10/1998 | Goodman et al. |
| 5,827,179 A | 10/1998 | Lichter et al. |
| 5,839,430 A | 11/1998 | Cama |
| 5,865,171 A | 2/1999 | Cinquin |
| 5,865,174 A | 2/1999 | Kloeppel |
| 5,875,777 A | 3/1999 | Eriksson |
| 5,878,744 A | 3/1999 | Pfeiffer |
| 5,881,723 A | 3/1999 | Wallace et al. |
| 5,884,622 A | 3/1999 | Younes |
| 5,891,023 A | 4/1999 | Lynn |
| 5,899,203 A | 5/1999 | Defares et al. |
| 5,915,379 A | 6/1999 | Wallace et al. |
| 5,915,380 A | 6/1999 | Wallace et al. |
| 5,921,920 A | 7/1999 | Marshall et al. |
| 5,924,418 A | 7/1999 | Lewis |
| 5,931,160 A | 8/1999 | Gilmore et al. |
| 5,932,812 A | 8/1999 | Delsing |
| 5,937,854 A | 8/1999 | Stenzler |
| 5,956,501 A | 9/1999 | Brown |
| 5,957,861 A | 9/1999 | Combs et al. |
| 5,971,937 A | 10/1999 | Ekstrom |
| 5,975,081 A | 11/1999 | Hood et al. |
| 5,979,440 A | 11/1999 | Honkonen et al. |
| 5,980,466 A | 11/1999 | Thomson |
| 6,003,070 A | 12/1999 | Frantz |
| 6,012,450 A | 1/2000 | Rubsamen |
| 6,017,315 A | 1/2000 | Starr et al. |
| 6,024,089 A | 2/2000 | Wallace et al. |
| 6,026,323 A | 2/2000 | Skladnev et al. |
| 6,032,119 A | 2/2000 | Brown et al. |
| 6,055,506 A | 4/2000 | Frasca, Jr. |
| 6,073,110 A | 6/2000 | Rhodes et al. |
| 6,099,481 A | 8/2000 | Daniels et al. |
| 6,106,481 A | 8/2000 | Cohen |
| 6,118,847 A | 9/2000 | Hernandez-Guerra et al. |
| 6,119,684 A | 9/2000 | Nohl et al. |
| 6,148,814 A | 11/2000 | Clemmer et al. |
| 6,148,815 A | 11/2000 | Wolf |
| 6,155,257 A | 12/2000 | Lurie et al. |
| 6,158,432 A | 12/2000 | Biondi et al. |
| 6,159,147 A | 12/2000 | Lichter et al. |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,179,784 B1 | 1/2001 | Daniels |
| 6,186,956 B1 | 2/2001 | McNamee |
| 6,190,326 B1 | 2/2001 | McKinnon et al. |
| 6,192,876 B1 | 2/2001 | Denyer et al. |
| 6,198,963 B1 | 3/2001 | Haim et al. |
| 6,199,550 B1 | 3/2001 | Wiesmann et al. |
| 6,202,642 B1 | 3/2001 | McKinnon |
| 6,213,955 B1 | 4/2001 | Karakasoglu et al. |
| 6,223,744 B1 | 5/2001 | Garon |
| 6,224,553 B1 | 5/2001 | Nevo |
| 6,233,539 B1 | 5/2001 | Brown |
| 6,234,963 B1 | 5/2001 | Blike et al. |
| 6,240,920 B1 | 6/2001 | Strom |
| 6,251,082 B1 | 6/2001 | Rayburn |
| 6,261,238 B1 | 7/2001 | Gavriely |
| 6,269,810 B1 | 8/2001 | Brooker et al. |
| 6,269,812 B1 | 8/2001 | Wallace et al. |
| 6,273,088 B1 | 8/2001 | Hillsman |
| 6,279,574 B1 | 8/2001 | Richardson et al. |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,373 B1 | 10/2001 | Wallace et al. |
| 6,322,502 B1 | 11/2001 | Schoenberg et al. |
| 6,339,410 B1 | 1/2002 | Milner et al. |
| 6,340,348 B1 | 1/2002 | Krishnan et al. |
| 6,342,040 B1 | 1/2002 | Starr et al. |
| 6,349,722 B1 | 2/2002 | Gradon et al. |
| 6,349,724 B1 | 2/2002 | Burton et al. |
| 6,355,002 B1 | 3/2002 | Faram et al. |
| 6,360,745 B1 | 3/2002 | Wallace et al. |
| 6,362,620 B1 | 3/2002 | Debbins et al. |
| 6,367,475 B1 | 4/2002 | Kofoed et al. |
| 6,369,838 B1 | 4/2002 | Wallace et al. |
| 6,370,419 B2 | 4/2002 | Lampotang et al. |
| 6,375,614 B1 | 4/2002 | Braun et al. |
| 6,377,046 B1 | 4/2002 | Debbins et al. |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,397,286 B1 | 5/2002 | Chatenever et al. |
| 6,402,698 B1 | 6/2002 | Mault |
| 6,408,043 B1 | 6/2002 | Hu et al. |
| 6,415,792 B1 | 7/2002 | Schoolman |
| 6,416,471 B1 | 7/2002 | Kumar et al. |
| 6,421,650 B1 | 7/2002 | Goetz et al. |
| 6,427,687 B1 | 8/2002 | Kirk |
| 6,435,175 B1 | 8/2002 | Stenzler |
| 6,436,053 B1 | 8/2002 | Knapp, II et al. |
| 6,450,164 B1 | 9/2002 | Banner et al. |
| 6,454,708 B1 | 9/2002 | Ferguson et al. |
| 6,459,933 B1 | 10/2002 | Lurie et al. |
| 6,463,930 B2 | 10/2002 | Biondi et al. |
| 6,471,658 B1 | 10/2002 | Daniels et al. |
| 6,477,424 B1 | 11/2002 | Thompson et al. |
| 6,488,029 B1 | 12/2002 | Hood et al. |
| 6,488,629 B1 | 12/2002 | Saetre et al. |
| RE37,970 E | 1/2003 | Costello, Jr. |
| 6,511,426 B1 | 1/2003 | Hossack et al. |
| 6,512,938 B2 | 1/2003 | Claure et al. |
| 6,515,683 B1 | 2/2003 | Wright |
| 6,517,497 B2 | 2/2003 | Rymut et al. |
| 6,533,723 B1 | 3/2003 | Lockery et al. |
| 6,533,730 B2 | 3/2003 | Strom |
| 6,543,449 B1 | 4/2003 | Woodring et al. |
| 6,543,701 B1 | 4/2003 | Ho |
| 6,544,192 B2 | 4/2003 | Starr et al. |
| 6,547,728 B1 | 4/2003 | Cornuejols |
| 6,551,252 B2 | 4/2003 | Sackner et al. |
| 6,553,992 B1 | 4/2003 | Berthon-Jones et al. |
| 6,557,554 B1 | 5/2003 | Sugiura |
| 6,566,875 B1 | 5/2003 | Hasson et al. |
| 6,571,122 B2 | 5/2003 | Schroeppel et al. |
| 6,571,796 B2 | 6/2003 | Banner et al. |
| 6,578,575 B1 | 6/2003 | Jonson |
| 6,581,117 B1 | 6/2003 | Klein et al. |

(56) References Cited

U.S. PATENT DOCUMENTS

| | | |
|---|---|---|
| 6,581,592 B1 | 6/2003 | Bathe et al. |
| 6,584,973 B1 | 7/2003 | Biondi et al. |
| 6,597,939 B1 | 7/2003 | Lampotang et al. |
| 6,599,252 B2 | 7/2003 | Starr |
| 6,603,494 B1 | 8/2003 | Banks et al. |
| 6,606,993 B1 | 8/2003 | Wiesmann et al. |
| 6,620,106 B2 | 9/2003 | Mault |
| 6,621,917 B1 | 9/2003 | Vilser |
| 6,629,934 B2 | 10/2003 | Mault et al. |
| 6,630,176 B2 | 10/2003 | Li et al. |
| 6,644,312 B2 | 11/2003 | Berthon-Jones et al. |
| 6,645,158 B2 | 11/2003 | Mault |
| 6,650,346 B1 | 11/2003 | Jaeger et al. |
| 6,651,653 B1 | 11/2003 | Honkonen et al. |
| 6,656,129 B2 | 12/2003 | Niles et al. |
| 6,665,385 B2 | 12/2003 | Rogers et al. |
| 6,668,829 B2 | 12/2003 | Biondi et al. |
| 6,671,529 B2 | 12/2003 | Claure et al. |
| 6,673,018 B2 | 1/2004 | Friedman |
| 6,675,801 B2 | 1/2004 | Wallace et al. |
| 6,679,258 B1 | 1/2004 | Strom |
| 6,681,764 B1 | 1/2004 | Honkonen et al. |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,975 B2 | 4/2004 | Blomberg |
| 6,725,077 B1 | 4/2004 | Balloni et al. |
| 6,725,860 B2 | 4/2004 | Wallroth et al. |
| 6,733,449 B1 | 5/2004 | Krishnamurthy et al. |
| 6,738,079 B1 | 5/2004 | Kellerman et al. |
| 6,740,046 B2 | 5/2004 | Knapp, II et al. |
| 6,743,172 B1 | 6/2004 | Blike |
| 6,744,374 B1 | 6/2004 | Kuenzner |
| 6,745,764 B2 | 6/2004 | Hickle |
| 6,755,193 B2 | 6/2004 | Berthon-Jones et al. |
| 6,755,787 B2 | 6/2004 | Hossack et al. |
| 6,760,610 B2 | 7/2004 | Tschupp et al. |
| 6,776,159 B2 | 8/2004 | Pelerossi et al. |
| 6,782,888 B1 | 8/2004 | Friberg et al. |
| 6,790,178 B1 | 9/2004 | Mault et al. |
| 6,792,066 B1 | 9/2004 | Harder et al. |
| 6,796,305 B1 | 9/2004 | Banner et al. |
| 6,801,227 B2 | 10/2004 | Bocionek et al. |
| 6,801,802 B2 | 10/2004 | Sitzman et al. |
| 6,804,656 B1 | 10/2004 | Rosenfeld et al. |
| 6,805,118 B2 | 10/2004 | Brooker et al. |
| 6,807,965 B1 | 10/2004 | Hickle |
| 6,820,614 B2 | 11/2004 | Bonutti |
| 6,820,618 B2 | 11/2004 | Banner et al. |
| 6,822,223 B2 | 11/2004 | Davis |
| 6,824,520 B2 | 11/2004 | Orr et al. |
| 6,828,910 B2 | 12/2004 | VanRyzin et al. |
| 6,830,046 B2 | 12/2004 | Blakley et al. |
| 6,834,647 B2 | 12/2004 | Blair et al. |
| 6,837,242 B2 | 1/2005 | Younes |
| 6,839,753 B2 | 1/2005 | Biondi et al. |
| 6,845,773 B2 | 1/2005 | Berthon-Jones et al. |
| 6,858,006 B2 | 2/2005 | MacCarter et al. |
| 6,860,266 B2 | 3/2005 | Blike |
| 6,866,629 B2 | 3/2005 | Bardy |
| 6,893,397 B2 | 5/2005 | Bardy |
| 6,895,963 B1 | 5/2005 | Martin |
| 6,899,103 B1 | 5/2005 | Hood et al. |
| 6,899,683 B2 | 5/2005 | Mault et al. |
| 6,899,684 B2 | 5/2005 | Mault et al. |
| 6,910,481 B2 | 6/2005 | Kimmel et al. |
| 6,921,369 B1 | 7/2005 | Gehrke et al. |
| 6,923,079 B1 | 8/2005 | Snibbe |
| 6,931,269 B2 | 8/2005 | Terry |
| 6,932,083 B2 | 8/2005 | Jones et al. |
| 6,932,767 B2 | 8/2005 | Landry et al. |
| 6,947,780 B2 | 9/2005 | Scharf |
| 6,951,541 B2 | 10/2005 | Desmarais |
| 6,954,702 B2 | 10/2005 | Pierry et al. |
| 6,956,572 B2 | 10/2005 | Zaleski |
| 6,970,919 B1 | 11/2005 | Doi et al. |
| 6,976,958 B2 | 12/2005 | Quy |
| 6,986,347 B2 | 1/2006 | Hickle |
| 6,997,185 B2 | 2/2006 | Han et al. |
| 6,997,880 B2 | 2/2006 | Carlebach et al. |
| 7,002,468 B2 | 2/2006 | Eveland et al. |
| 7,008,380 B1 | 3/2006 | Rees et al. |
| 7,017,574 B2 | 3/2006 | Biondi et al. |
| 7,019,652 B2 | 3/2006 | Richardson |
| 7,033,323 B2 | 4/2006 | Botbol et al. |
| 7,036,504 B2 | 5/2006 | Wallace et al. |
| 7,039,878 B2 | 5/2006 | Auer et al. |
| 7,040,315 B1 | 5/2006 | Strömberg |
| 7,040,318 B2 | 5/2006 | Däscher et al. |
| 7,040,321 B2 | 5/2006 | Göbel |
| 7,046,254 B2 | 5/2006 | Brown et al. |
| 7,047,092 B2 | 5/2006 | Wimsatt |
| 7,051,088 B2 | 5/2006 | Sesek |
| 7,051,736 B2 | 5/2006 | Banner et al. |
| 7,062,251 B2 | 6/2006 | Birkett et al. |
| 7,066,173 B2 | 6/2006 | Banner et al. |
| 7,077,125 B2 | 7/2006 | Scheuch |
| 7,081,091 B2 | 7/2006 | Merrett et al. |
| 7,081,095 B2 | 7/2006 | Lynn et al. |
| 7,083,574 B2 | 8/2006 | Kline |
| 7,089,927 B2 | 8/2006 | John et al. |
| 7,089,932 B2 | 8/2006 | Dodds |
| 7,089,937 B2 | 8/2006 | Berthon-Jones et al. |
| 7,094,208 B2 | 8/2006 | Williams et al. |
| 7,099,801 B1 | 8/2006 | McBride et al. |
| 7,116,810 B2 | 10/2006 | Miller et al. |
| 7,117,438 B2 | 10/2006 | Wallace et al. |
| 7,128,578 B2 | 10/2006 | Lampotang et al. |
| 7,147,600 B2 | 12/2006 | Bardy |
| 7,154,397 B2 | 12/2006 | Zerhusen et al. |
| 7,154,398 B2 | 12/2006 | Chen et al. |
| 7,156,808 B2 | 1/2007 | Quy |
| 7,162,296 B2 | 1/2007 | Leonhardt et al. |
| 7,164,972 B2 | 1/2007 | Imhof et al. |
| 7,165,221 B2 | 1/2007 | Monteleone et al. |
| 7,169,112 B2 | 1/2007 | Caldwell |
| 7,171,606 B2 | 1/2007 | Blackburn et al. |
| 7,172,557 B1 | 2/2007 | Parker |
| 7,182,083 B2 | 2/2007 | Yanof et al. |
| 7,187,790 B2 | 3/2007 | Sabol et al. |
| 7,188,621 B2 | 3/2007 | DeVries et al. |
| 7,201,734 B2 | 4/2007 | Hickle |
| 7,203,353 B2 | 4/2007 | Klotz et al. |
| 7,210,478 B2 | 5/2007 | Banner et al. |
| 7,211,049 B2 | 5/2007 | Bradley et al. |
| 7,219,666 B2 | 5/2007 | Friberg et al. |
| 7,220,230 B2 | 5/2007 | Roteliuk et al. |
| 7,222,054 B2 | 5/2007 | Geva |
| 7,223,965 B2 | 5/2007 | Davis |
| 7,225,809 B1 | 6/2007 | Bowen |
| 7,228,323 B2 | 6/2007 | Angerer et al. |
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,256,708 B2 | 8/2007 | Rosenfeld et al. |
| 7,258,670 B2 | 8/2007 | Bardy |
| 7,261,690 B2 | 8/2007 | Teller et al. |
| 7,264,730 B2 | 9/2007 | Connell et al. |
| 7,270,126 B2 | 9/2007 | Wallace et al. |
| 7,275,540 B2 | 10/2007 | Bolam et al. |
| 7,278,579 B2 | 10/2007 | Loffredo et al. |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell et al. |
| 7,307,543 B2 | 12/2007 | Rosenfeld et al. |
| 7,308,550 B2 | 12/2007 | Cornett |
| 7,310,551 B1 | 12/2007 | Koh et al. |

(56) References Cited

U.S. PATENT DOCUMENTS

| | | |
|---|---|---|
| 7,310,720 B2 | 12/2007 | Cornett |
| 7,311,665 B2 | 12/2007 | Hawthorne et al. |
| 7,314,451 B2 | 1/2008 | Halperin et al. |
| 7,315,825 B2 | 1/2008 | Rosenfeld et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,321,862 B2 | 1/2008 | Rosenfeld et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,337,778 B2 | 3/2008 | Martin |
| 7,343,916 B2 | 3/2008 | Biondo et al. |
| 7,343,917 B2 | 3/2008 | Jones |
| 7,347,200 B2 | 3/2008 | Jones et al. |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,374,535 B2 | 5/2008 | Schoenberg et al. |
| 7,377,276 B2 | 5/2008 | Roy et al. |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,395,216 B2 | 7/2008 | Rosenfeld et al. |
| 7,413,546 B2 | 8/2008 | Agutter et al. |
| 7,422,562 B2 | 9/2008 | Hatib et al. |
| 7,425,201 B2 | 9/2008 | Euliano et al. |
| 7,433,827 B2 | 10/2008 | Rosenfeld et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,448,383 B2 | 11/2008 | Delache et al. |
| 7,452,333 B2 | 11/2008 | Roteliuk |
| 7,454,359 B2 | 11/2008 | Rosenfeld et al. |
| 7,454,360 B2 | 11/2008 | Rosenfeld et al. |
| 7,464,339 B2 | 12/2008 | Keenan, Jr. et al. |
| 7,467,094 B2 | 12/2008 | Rosenfeld et al. |
| 7,469,698 B1 | 12/2008 | Childers et al. |
| 7,475,019 B2 | 1/2009 | Rosenfeld et al. |
| 7,487,774 B2 | 2/2009 | Acker |
| 7,490,085 B2 | 2/2009 | Walker et al. |
| 7,496,400 B2 | 2/2009 | Hoskonen et al. |
| 7,500,481 B2 | 3/2009 | Delache et al. |
| 7,504,954 B2 | 3/2009 | Spaeder |
| 7,512,450 B2 | 3/2009 | Ahmed |
| 7,512,593 B2 | 3/2009 | Karklins et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,574,368 B2 | 8/2009 | Pawlikowski |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,650,291 B2 | 1/2010 | Rosenfeld et al. |
| 7,652,571 B2 | 1/2010 | Parkulo et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,698,156 B2 | 4/2010 | Martucci et al. |
| 7,708,015 B2 | 5/2010 | Seeger et al. |
| 7,717,112 B2 | 5/2010 | Sun et al. |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,844,657 B2 | 11/2010 | Novak |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| 7,874,290 B2 | 1/2011 | Chalvignac |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,981,042 B2 | 7/2011 | Stahmann |
| 8,015,972 B2 | 9/2011 | Pirzada |
| 8,105,282 B2 | 1/2012 | Susi |
| 8,151,792 B2 | 4/2012 | Ishizaki |
| 8,214,231 B2 | 7/2012 | Martucci |
| 8,276,585 B2 | 10/2012 | Buckley |
| 8,381,724 B2 | 2/2013 | Bowen |
| 8,500,694 B2 | 8/2013 | Susi |
| 8,545,416 B1 | 10/2013 | Kayyali |
| 8,596,269 B2 | 12/2013 | Chalvignac |
| 8,627,819 B2 | 1/2014 | DeVries |
| 8,679,012 B1 | 3/2014 | Kayyali |
| 8,747,329 B2 | 6/2014 | Bardy |
| 8,795,168 B2 | 8/2014 | Goh |
| 8,844,522 B2 | 9/2014 | Huby |
| 8,881,724 B2 | 11/2014 | Choncholas |
| 8,882,747 B2 | 11/2014 | Hood |
| 8,938,753 B2 | 1/2015 | Tang |
| 8,939,147 B2 | 1/2015 | Henry |

(56) References Cited

U.S. PATENT DOCUMENTS

| | | | |
|---|---|---|---|
| 8,968,195 B2 | 3/2015 | Tran | |
| 9,058,741 B2 | 6/2015 | Steinhauer | |
| 9,098,114 B2 | 8/2015 | Potter | |
| 9,155,919 B2 | 10/2015 | Huh | |
| 9,177,109 B2 | 11/2015 | Steinhauer | |
| 9,202,008 B1 | 12/2015 | Frederick | |
| 9,210,359 B2 | 12/2015 | Kim | |
| 9,327,090 B2 | 3/2016 | Steinhauer | |
| 9,330,497 B2 | 5/2016 | Byrd | |
| 9,364,625 B2 | 6/2016 | Silver | |
| 9,426,607 B2 | 8/2016 | Shelly | |
| 9,436,645 B2 | 9/2016 | Al-Ali | |
| 9,463,294 B2 * | 10/2016 | Laura Lapoint | A61M 16/024 |
| 9,533,114 B1 | 1/2017 | Kayyali | |
| 9,550,037 B2 * | 1/2017 | Seiver | G16H 20/40 |
| 9,600,304 B2 * | 3/2017 | DiVincent | G06F 21/32 |
| 9,621,433 B2 * | 4/2017 | Yoshida | G06F 3/04847 |
| 9,662,464 B2 | 5/2017 | Shelly | |
| 9,671,928 B2 * | 6/2017 | Kreiner | G08C 17/00 |
| 9,734,293 B2 * | 8/2017 | Collins, Jr. | A61B 5/002 |
| 9,736,546 B2 * | 8/2017 | Ferren | H04N 21/43615 |
| 9,737,675 B2 * | 8/2017 | Frame | G16H 20/40 |
| 9,737,676 B2 * | 8/2017 | Steinhauer | G16H 20/40 |
| 9,743,890 B2 * | 8/2017 | Lord | A61B 5/746 |
| 9,769,413 B2 | 9/2017 | Kim | |
| 9,775,566 B2 * | 10/2017 | Sullivan | A61M 16/0069 |
| 9,820,658 B2 * | 11/2017 | Tran | A61B 5/7225 |
| 9,821,129 B2 * | 11/2017 | Steinhauer | A61M 16/0057 |
| 9,833,584 B2 * | 12/2017 | Ahmad | A61M 16/0051 |
| 9,839,058 B2 * | 12/2017 | Shelly | H02J 7/02 |
| 9,839,398 B2 * | 12/2017 | Yamamori | A61B 5/742 |
| 9,861,743 B2 | 1/2018 | Susi | |
| 9,876,652 B2 * | 1/2018 | Tatzel | H04L 41/22 |
| 9,888,881 B2 * | 2/2018 | Hulvershorn | A61B 5/4896 |
| 9,895,066 B2 | 2/2018 | Krauss | |
| 9,913,617 B2 | 3/2018 | Al-Ali | |
| 9,956,365 B2 * | 5/2018 | Bonassa | A61M 16/0666 |
| 9,993,207 B2 | 6/2018 | Al-Ali | |
| 9,998,580 B2 * | 6/2018 | Brogan | G06F 1/1633 |
| 10,076,269 B1 * | 9/2018 | Kayyali | A61M 16/0069 |
| 10,098,594 B2 * | 10/2018 | Shtalryd | A61B 5/113 |
| 10,117,975 B2 * | 11/2018 | Wall | A61M 1/96 |
| 10,159,811 B2 | 12/2018 | Silver | |
| 10,179,217 B2 | 1/2019 | Steinhauer | |
| 10,245,437 B2 * | 4/2019 | Kantor | A61M 16/0003 |
| 10,255,647 B2 * | 4/2019 | Rodman | G16H 40/63 |
| 10,334,888 B2 * | 7/2019 | Cameron | A24F 40/50 |
| 10,335,031 B1 * | 7/2019 | Kundu | G16H 40/67 |
| 10,448,885 B2 * | 10/2019 | Schmid | A61B 5/0022 |
| 10,478,118 B1 | 11/2019 | Frederick | |
| 10,569,036 B2 * | 2/2020 | Delangre | A61M 16/0069 |
| 10,576,226 B2 | 3/2020 | Kwok | |
| 10,638,999 B2 * | 5/2020 | Shah | A61M 16/1005 |
| 10,646,673 B2 | 5/2020 | Steinhauer | |
| 10,646,674 B2 | 5/2020 | Steinhauer | |
| 10,668,234 B2 * | 6/2020 | Paul | A61M 16/06 |
| 10,678,400 B2 | 6/2020 | Kreiner | |
| 10,679,748 B2 * | 6/2020 | Durlach | G16H 40/67 |
| 10,734,112 B2 * | 8/2020 | Bychkov | G16H 40/40 |
| 10,744,284 B2 | 8/2020 | Paul | |
| 10,814,082 B2 * | 10/2020 | Birnkrant | G16H 20/40 |
| 10,828,438 B2 * | 11/2020 | Thompson | A61M 21/02 |
| 10,835,700 B2 * | 11/2020 | Lunz | A63B 21/023 |
| 10,843,014 B2 * | 11/2020 | Dobbing | G16H 40/67 |
| 10,905,611 B2 * | 2/2021 | Sidhu | A61G 7/015 |
| 2001/0056358 A1 | 12/2001 | Dulong et al. | |
| 2002/0026941 A1 | 3/2002 | Biondi et al. | |
| 2002/0044059 A1 | 4/2002 | Reeder et al. | |
| 2002/0077863 A1 | 6/2002 | Rutledge et al. | |
| 2002/0091548 A1 | 7/2002 | Auer et al. | |
| 2002/0133061 A1 | 9/2002 | Manetta | |
| 2002/0177758 A1 | 11/2002 | Schoenberg et al. | |
| 2003/0028226 A1 | 2/2003 | Thompson et al. | |
| 2003/0060723 A1 | 3/2003 | Joo et al. | |
| 2003/0062045 A1 | 4/2003 | Woodring et al. | |
| 2003/0106553 A1 | 6/2003 | Vanderveen | |
| 2003/0130567 A1 | 7/2003 | Mault et al. | |
| 2003/0130595 A1 | 7/2003 | Mault | |
| 2003/0140928 A1 | 7/2003 | Bui et al. | |
| 2003/0140929 A1 | 7/2003 | Wilkes et al. | |
| 2003/0141368 A1 | 7/2003 | Pascual et al. | |
| 2003/0141981 A1 | 7/2003 | Bui et al. | |
| 2003/0144878 A1 | 7/2003 | Wilkes et al. | |
| 2003/0144880 A1 | 7/2003 | Talachian et al. | |
| 2003/0144881 A1 | 7/2003 | Talachian et al. | |
| 2003/0144882 A1 | 7/2003 | Talachian et al. | |
| 2003/0201697 A1 | 10/2003 | Richardson | |
| 2003/0204414 A1 | 10/2003 | Wilkes et al. | |
| 2003/0204416 A1 | 10/2003 | Radpay et al. | |
| 2003/0204419 A1 | 10/2003 | Wilkes et al. | |
| 2003/0204420 A1 | 10/2003 | Wilkes et al. | |
| 2003/0208152 A1 | 11/2003 | Avrahami et al. | |
| 2003/0208465 A1 | 11/2003 | Yurko et al. | |
| 2003/0222548 A1 | 12/2003 | Richardson et al. | |
| 2003/0230308 A1 | 12/2003 | Linden | |
| 2004/0010425 A1 | 1/2004 | Wilkes et al. | |
| 2004/0034289 A1 | 2/2004 | Teller et al. | |
| 2004/0059604 A1 | 3/2004 | Zaleski | |
| 2004/0073453 A1 | 4/2004 | Nenov et al. | |
| 2004/0078231 A1 | 4/2004 | Wilkes et al. | |
| 2004/0121767 A1 | 6/2004 | Simpson et al. | |
| 2004/0122294 A1 | 6/2004 | Hatlestad et al. | |
| 2004/0143677 A1 | 7/2004 | Novak | |
| 2004/0150525 A1 | 8/2004 | Wilson et al. | |
| 2004/0167465 A1 | 8/2004 | Mihai et al. | |
| 2004/0167804 A1 | 8/2004 | Simpson et al. | |
| 2004/0172222 A1 | 9/2004 | Simpson et al. | |
| 2004/0172300 A1 | 9/2004 | Mihai et al. | |
| 2004/0172301 A1 | 9/2004 | Mihai et al. | |
| 2004/0172302 A1 | 9/2004 | Martucci et al. | |
| 2004/0176667 A1 | 9/2004 | Mihai et al. | |
| 2004/0224293 A1 | 11/2004 | Penning et al. | |
| 2004/0236240 A1 | 11/2004 | Kraus et al. | |
| 2004/0249673 A1 | 12/2004 | Smith | |
| 2005/0016534 A1 | 1/2005 | Ost | |
| 2005/0033198 A1 | 2/2005 | Kehyayan et al. | |
| 2005/0054910 A1 | 3/2005 | Tremblay et al. | |
| 2005/0055242 A1 | 3/2005 | Bello et al. | |
| 2005/0055244 A1 | 3/2005 | Mullan et al. | |
| 2005/0065817 A1 | 3/2005 | Mihai et al. | |
| 2005/0075542 A1 | 4/2005 | Goldreich | |
| 2005/0075904 A1 | 4/2005 | Wager et al. | |
| 2005/0085869 A1 | 4/2005 | Tehrani et al. | |
| 2005/0108057 A1 | 5/2005 | Cohen et al. | |
| 2005/0112013 A1 | 5/2005 | DeVries et al. | |
| 2005/0112325 A1 | 5/2005 | Hickle | |
| 2005/0124866 A1 | 6/2005 | Elaz et al. | |
| 2005/0133027 A1 | 6/2005 | Elaz et al. | |
| 2005/0137480 A1 | 6/2005 | Alt et al. | |
| 2005/0139213 A1 | 6/2005 | Blike | |
| 2005/0143632 A1 | 6/2005 | Elaz et al. | |
| 2005/0156933 A1 | 7/2005 | Lee et al. | |
| 2005/0171876 A1 | 8/2005 | Golden | |
| 2005/0177096 A1 | 8/2005 | Bollish et al. | |
| 2005/0177400 A1 | 8/2005 | Rosenfeld et al. | |
| 2005/0188083 A1 | 8/2005 | Biondi et al. | |
| 2005/0192488 A1 | 9/2005 | Bryenton et al. | |
| 2005/0204310 A1 | 9/2005 | De Zwart et al. | |
| 2005/0215904 A1 | 9/2005 | Sumanaweera et al. | |
| 2005/0217674 A1 | 10/2005 | Burton et al. | |
| 2005/0251040 A1 | 11/2005 | Relkuntwar et al. | |
| 2005/0288571 A1 | 12/2005 | Perkins et al. | |
| 2006/0025657 A1 | 2/2006 | Rosenfeld et al. | |
| 2006/0047202 A1 | 3/2006 | Elliott | |
| 2006/0078867 A1 | 4/2006 | Penny et al. | |
| 2006/0080140 A1 | 4/2006 | Buttner et al. | |
| 2006/0080343 A1 | 4/2006 | Carter et al. | |
| 2006/0085229 A9 | 4/2006 | Rosenfeld et al. | |
| 2006/0102171 A1 | 5/2006 | Gavish | |
| 2006/0122474 A1 | 6/2006 | Teller et al. | |
| 2006/0129055 A1 | 6/2006 | Orr et al. | |
| 2006/0144396 A1 | 7/2006 | DeVries et al. | |
| 2006/0149144 A1 | 7/2006 | Lynn et al. | |
| 2006/0149589 A1 | 7/2006 | Wager | |

(56) References Cited

U.S. PATENT DOCUMENTS

| | | |
|---|---|---|
| 2006/0150982 A1 | 7/2006 | Wood |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn et al. |
| 2006/0196507 A1 | 9/2006 | Bradley |
| 2006/0200009 A1 | 9/2006 | Wekell et al. |
| 2006/0213518 A1 | 9/2006 | DeVries et al. |
| 2006/0229822 A1 | 10/2006 | Theobald et al. |
| 2006/0235324 A1 | 10/2006 | Lynn |
| 2006/0237015 A1 | 10/2006 | Berthon-Jones et al. |
| 2006/0249151 A1 | 11/2006 | Gambone |
| 2006/0249153 A1 | 11/2006 | DeVries et al. |
| 2006/0264762 A1 | 11/2006 | Starr |
| 2006/0271409 A1 | 11/2006 | Rosenfeld et al. |
| 2006/0278221 A1 | 12/2006 | Schermeier et al. |
| 2006/0278222 A1 | 12/2006 | Schermeier et al. |
| 2006/0293609 A1 | 12/2006 | Stahmann et al. |
| 2006/0294464 A1 | 12/2006 | Tokimoto et al. |
| 2007/0000490 A1 | 1/2007 | DeVries et al. |
| 2007/0000494 A1 | 1/2007 | Banner et al. |
| 2007/0016441 A1 | 1/2007 | Stroup |
| 2007/0017515 A1 | 1/2007 | Wallace et al. |
| 2007/0021673 A1 | 1/2007 | Arbel et al. |
| 2007/0028921 A1 | 2/2007 | Banner et al. |
| 2007/0038081 A1 | 2/2007 | Eck et al. |
| 2007/0060812 A1 | 3/2007 | Harel et al. |
| 2007/0062532 A1 | 3/2007 | Choncholas |
| 2007/0062533 A1 | 3/2007 | Choncholas et al. |
| 2007/0073181 A1 | 3/2007 | Pu et al. |
| 2007/0113849 A1 | 5/2007 | Matthews et al. |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0149860 A1 | 6/2007 | Lynn et al. |
| 2007/0155208 A1 | 7/2007 | Pirzada |
| 2007/0156060 A1 | 7/2007 | Cervantes |
| 2007/0156456 A1 | 7/2007 | McGillin et al. |
| 2007/0157931 A1 | 7/2007 | Parker et al. |
| 2007/0163589 A1 | 7/2007 | DeVries et al. |
| 2007/0179357 A1 | 8/2007 | Bardy |
| 2007/0185390 A1 | 8/2007 | Perkins et al. |
| 2007/0191697 A1 | 8/2007 | Lynn et al. |
| 2007/0199566 A1 | 8/2007 | Be'eri |
| 2007/0208438 A1 | 9/2007 | El-Mankabady et al. |
| 2007/0215155 A1 | 9/2007 | Marx et al. |
| 2007/0225574 A1 | 9/2007 | Ueda |
| 2007/0241884 A1 | 10/2007 | Yamazaki et al. |
| 2007/0265510 A1 | 11/2007 | Bardy |
| 2007/0265877 A1 | 11/2007 | Rice et al. |
| 2007/0271122 A1 | 11/2007 | Zaleski |
| 2007/0272241 A1 | 11/2007 | Sanborn et al. |
| 2007/0272242 A1 | 11/2007 | Sanborn et al. |
| 2007/0273216 A1 | 11/2007 | Farbarik |
| 2007/0276439 A1 | 11/2007 | Miesel et al. |
| 2007/0293741 A1 | 12/2007 | Bardy |
| 2008/0000477 A1 | 1/2008 | Huster et al. |
| 2008/0000479 A1 | 1/2008 | Elaz et al. |
| 2008/0033661 A1 | 2/2008 | Syroid et al. |
| 2008/0039735 A1 | 2/2008 | Hickerson |
| 2008/0041380 A1 | 2/2008 | Wallace et al. |
| 2008/0045844 A1 | 2/2008 | Arbel et al. |
| 2008/0047554 A1 | 2/2008 | Roy et al. |
| 2008/0053438 A1 | 3/2008 | DeVries et al. |
| 2008/0064963 A1 | 3/2008 | Schwaibold et al. |
| 2008/0065420 A1 | 3/2008 | Tirinato et al. |
| 2008/0066753 A1 | 3/2008 | Martin et al. |
| 2008/0072896 A1 | 3/2008 | Setzer et al. |
| 2008/0072900 A1 | 3/2008 | Kenyon et al. |
| 2008/0072901 A1 | 3/2008 | Habashi |
| 2008/0072902 A1 | 3/2008 | Setzer et al. |
| 2008/0076970 A1 | 3/2008 | Foulis et al. |
| 2008/0077038 A1 | 3/2008 | McDonough et al. |
| 2008/0078390 A1 | 4/2008 | Milne et al. |
| 2008/0092043 A1 | 4/2008 | Trethewey |
| 2008/0103368 A1 | 5/2008 | Craine et al. |
| 2008/0110460 A1 | 5/2008 | Elaz et al. |
| 2008/0125873 A1 | 5/2008 | Payne et al. |
| 2008/0143515 A1 | 6/2008 | Wood et al. |
| 2008/0161653 A1 | 7/2008 | Lin et al. |
| 2008/0178880 A1 | 7/2008 | Christopher et al. |
| 2008/0178882 A1 | 7/2008 | Christopher et al. |
| 2008/0183057 A1 | 7/2008 | Taube |
| 2008/0185009 A1 | 8/2008 | Choncholas et al. |
| 2008/0208012 A1 | 8/2008 | Ali |
| 2008/0214947 A1 | 9/2008 | Hunt et al. |
| 2008/0230057 A1 | 9/2008 | Sutherland |
| 2008/0236582 A1 | 10/2008 | Tehrani |
| 2008/0236585 A1 | 10/2008 | Parker et al. |
| 2008/0243016 A1 | 10/2008 | Liao et al. |
| 2008/0251070 A1 | 10/2008 | Pinskiy et al. |
| 2008/0255880 A1 | 10/2008 | Beller et al. |
| 2008/0270912 A1 | 10/2008 | Booth |
| 2008/0281219 A1 | 11/2008 | Glickman et al. |
| 2008/0293025 A1 | 11/2008 | Zamierowsi et al. |
| 2008/0295830 A1 | 12/2008 | Martonen et al. |
| 2008/0295839 A1 | 12/2008 | Habashi |
| 2008/0306351 A1 | 12/2008 | Izumi |
| 2008/0308109 A1 | 12/2008 | Brain |
| 2008/0312954 A1 | 12/2008 | Ullrich et al. |
| 2008/0319513 A1 | 12/2008 | Pu et al. |
| 2009/0005651 A1 | 1/2009 | Ward et al. |
| 2009/0007909 A1 | 1/2009 | Carrico |
| 2009/0038921 A1 | 2/2009 | Kaps et al. |
| 2009/0054743 A1 | 2/2009 | Stewart |
| 2009/0062725 A1 | 3/2009 | Goebel |
| 2009/0063181 A1 | 3/2009 | Nho et al. |
| 2009/0065004 A1 | 3/2009 | Childers et al. |
| 2009/0076342 A1 | 3/2009 | Amurthur et al. |
| 2009/0124917 A1 | 5/2009 | Hatlestad et al. |
| 2009/0125333 A1 | 5/2009 | Heywood et al. |
| 2009/0126734 A1 | 5/2009 | Dunsmore et al. |
| 2009/0131758 A1 | 5/2009 | Heywood et al. |
| 2009/0133701 A1 | 5/2009 | Brain |
| 2009/0143694 A1 | 6/2009 | Krauss et al. |
| 2009/0145438 A1 | 6/2009 | Brain |
| 2009/0149200 A1 | 6/2009 | Jayasinghe et al. |
| 2009/0149723 A1 | 6/2009 | Krauss et al. |
| 2009/0149927 A1 | 6/2009 | Kneuer et al. |
| 2009/0150184 A1 | 6/2009 | Spahn |
| 2009/0171167 A1 | 7/2009 | Baker, Jr. |
| 2009/0192421 A1 | 7/2009 | Huster et al. |
| 2009/0209828 A1 | 8/2009 | Musin |
| 2009/0209849 A1 | 8/2009 | Rowe et al. |
| 2009/0216145 A1 | 8/2009 | Skerl et al. |
| 2009/0221926 A1 | 9/2009 | Younes |
| 2009/0240523 A1 | 9/2009 | Friedlander et al. |
| 2009/0241952 A1 | 10/2009 | Nicolazzi et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0244003 A1 | 10/2009 | Bonnat |
| 2009/0250054 A1 | 10/2009 | Loncar et al. |
| 2010/0004517 A1 | 1/2010 | Bryenton et al. |
| 2010/0022904 A1 | 1/2010 | Centen |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |

(56) References Cited

U.S. PATENT DOCUMENTS

| | | | |
|---|---|---|---|
| 2010/0059061 | A1 | 3/2010 | Brain |
| 2010/0063348 | A1 | 3/2010 | Henke et al. |
| 2010/0063350 | A1 | 3/2010 | Henke et al. |
| 2010/0063365 | A1 | 3/2010 | Pisani et al. |
| 2010/0069774 | A1 | 3/2010 | Bingham et al. |
| 2010/0072055 | A1 | 3/2010 | Tanaka et al. |
| 2010/0076278 | A1 | 3/2010 | van der Zande et al. |
| 2010/0081890 | A1 | 4/2010 | Li et al. |
| 2010/0083968 | A1 | 4/2010 | Wondka et al. |
| 2010/0095961 | A1 | 4/2010 | Tornesel et al. |
| 2010/0130873 | A1 | 5/2010 | Yuen et al. |
| 2010/0160839 | A1 | 6/2010 | Freeman et al. |
| 2010/0274100 | A1 | 10/2010 | Behar et al. |
| 2010/0298718 | A1 | 11/2010 | Gilham et al. |
| 2010/0312132 | A1 | 12/2010 | Wood et al. |
| 2010/0317980 | A1 | 12/2010 | Guglielmino |
| 2011/0004489 | A1 | 1/2011 | Schoenberg et al. |
| 2011/0009746 | A1 | 1/2011 | Tran et al. |
| 2011/0015493 | A1 | 1/2011 | Koschek |
| 2011/0041849 | A1 | 2/2011 | Chen et al. |
| 2011/0054289 | A1 | 3/2011 | Derchak et al. |
| 2012/0185268 | A1 | 7/2012 | Wiesner |
| 2015/0070187 | A1 | 3/2015 | Wiesner |
| 2015/0099458 | A1 | 4/2015 | Wiesner |
| 2017/0372600 | A1* | 12/2017 | Palin .............. H04W 4/80 |
| 2018/0181091 | A1* | 6/2018 | Funk .............. G08G 1/133 |

FOREIGN PATENT DOCUMENTS

| | | |
|---|---|---|
| EP | 1464357 | 10/2004 |
| GB | 2319967 | 6/1998 |
| WO | WO 9014852 | 12/1990 |
| WO | WO 9308534 | 4/1993 |
| WO | WO 9312823 | 7/1993 |
| WO | WO 9314696 | 8/1993 |
| WO | WO 9414374 | 7/1994 |
| WO | WO 9508471 | 3/1995 |
| WO | WO 9532480 | 11/1995 |
| WO | WO 9624285 | 8/1996 |
| WO | WO 9720592 | 6/1997 |
| WO | WO 9811840 | 3/1998 |
| WO | WO 9814116 | 4/1998 |
| WO | WO 9829790 | 7/1998 |
| WO | WO 9833554 | 8/1998 |
| WO | WO 9840014 | 9/1998 |
| WO | WO 9841267 A1 | 9/1998 |
| WO | WO 9841267 C1 | 9/1998 |
| WO | WO 9841269 | 9/1998 |
| WO | WO 9841270 | 9/1998 |
| WO | WO 9841271 | 9/1998 |
| WO | WO 9858219 | 12/1998 |
| WO | WO 9903524 | 1/1999 |
| WO | WO 9952431 | 10/1999 |
| WO | WO 9952437 | 10/1999 |
| WO | WO 9959460 | 11/1999 |
| WO | WO 9962403 | 12/1999 |
| WO | WO 0018293 | 4/2000 |
| WO | WO 0019886 | 4/2000 |
| WO | WO 0062664 | 10/2000 |
| WO | WO 200079466 | 12/2000 |
| WO | WO 0100264 | 1/2001 |
| WO | WO 0100265 | 1/2001 |
| WO | WO 0128416 | 4/2001 |
| WO | WO 0134022 | 5/2001 |
| WO | WO 0245566 | 6/2002 |
| WO | WO 02082967 | 10/2002 |
| WO | WO 03015005 | 2/2003 |
| WO | WO 03024317 | 3/2003 |
| WO | WO 03045493 | 6/2003 |
| WO | WO 03053503 | 7/2003 |
| WO | WO 03060650 | 7/2003 |
| WO | WO 03060651 | 7/2003 |
| WO | WO 03075989 | 9/2003 |
| WO | WO 03075990 | 9/2003 |
| WO | WO 03075991 | 9/2003 |
| WO | WO 03084405 | 10/2003 |
| WO | WO 04014216 | 2/2004 |
| WO | WO 04014226 | 2/2004 |
| WO | WO 04032719 | 4/2004 |
| WO | WO 04043254 | 5/2004 |
| WO | WO 2005010796 | 2/2005 |
| WO | WO 05024729 | 3/2005 |
| WO | WO 05055825 | 6/2005 |
| WO | WO 05056087 | 6/2005 |
| WO | WO 05069740 | 8/2005 |
| WO | WO 05077260 | 8/2005 |
| WO | WO 05112739 | 12/2005 |
| WO | WO 06008745 | 1/2006 |
| WO | WO 06009830 | 1/2006 |
| WO | WO 06037184 | 4/2006 |
| WO | WO 06050388 | 5/2006 |
| WO | WO 06051466 | 5/2006 |
| WO | WO 06078432 | 7/2006 |
| WO | WO 06094055 | 9/2006 |
| WO | WO 06096080 | 9/2006 |
| WO | WO 06109072 | 10/2006 |
| WO | WO 06123956 | 11/2006 |
| WO | WO 06125986 | 11/2006 |
| WO | WO 06125987 | 11/2006 |
| WO | WO 06125989 | 11/2006 |
| WO | WO 06125990 | 11/2006 |
| WO | WO 06137067 | 12/2006 |
| WO | WO 2007033050 | 3/2007 |
| WO | WO 2007106804 | 9/2007 |
| WO | WO 07145948 | 12/2007 |
| WO | WO 2008030091 | 3/2008 |
| WO | WO 2008042699 | 4/2008 |
| WO | WO 2008058997 | 5/2008 |
| WO | WO 2008062554 | 5/2008 |
| WO | WO 2008113410 | 9/2008 |
| WO | WO 2008118951 | 10/2008 |
| WO | WO 2008140528 | 11/2008 |
| WO | WO 2008146264 | 12/2008 |
| WO | WO 2008148134 | 12/2008 |
| WO | WO 2009024967 | 2/2009 |
| WO | WO 2009027864 | 3/2009 |
| WO | WO 2009036334 | 3/2009 |
| WO | WO 2009124297 | 10/2009 |
| WO | WO 2010009531 | 1/2010 |
| WO | WO 2010020980 | 2/2010 |
| WO | WO 2010021730 | 2/2010 |
| WO | WO 2010039989 | 4/2010 |
| WO | WO 2010126916 | 11/2010 |
| WO | WO 2010141415 | 12/2010 |
| WO | WO 2011005953 | 1/2011 |
| WO | WO 2011022242 | 2/2011 |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Puritan Bennett 980 Series Ventilator Operator's Manual, Covidien, Jan. 29, 2014, Part. No. 10077893 A Jan. 2014, 506 pages.
International Written Opinion for International Application No. PCT/US2021/030117 mailed Jul. 15, 2021 (11 pages).
International Search Report for International Application No. PCT/US2021/030117 mailed Jul. 15, 2021 (4 pages).
Anonymous "Mobile High-Definition Link—Wikipedia" retrieved from the internet Jan. 16, 2020—hllps://en.wikipedia.org/w/index.php?lille=Mobile_High-Definition_Link&oldid=936134359.
Patel. "Apr. 7, 2021 Overview of Mechanical Ventilation—Critical Care Medicine—MSD Manual Professional Edition Overview of Mechanical Ventilation." Retrieved from the Internet: Mar. 13, 2020

(56) References Cited

OTHER PUBLICATIONS https://www.msdmanuals.com/professional/critical-care-medicine/respiratory-failure-and-mechanical-venlilalion/overview--0f-mechanical-venlilalion#.

* cited by examiner

REMOTE VENTILATOR ADJUSTMENT

CROSS-REFERENCE TO RELATED APPLICATIONS

This application is a continuation of U.S. patent application Ser. No. 17/241,638, filed Apr. 27, 2021, which claims the benefit of U.S. Provisional Application No. 63/023,343, filed May 12, 2020, and U.S. Provisional Application No. 63/050,214, filed Jul. 10, 2020, the complete disclosures of which are hereby incorporated herein by reference in their entireties.

INTRODUCTION

Medical ventilator systems have long been used to provide ventilatory and supplemental oxygen support to patients. These ventilators typically comprise a connection for pressurized gas (air, oxygen) that is delivered to the patient through a conduit or tubing. As each patient may require a different ventilation strategy, modern ventilators can be customized for the particular needs of an individual patient. For example, several different ventilator modes or settings have been created to provide better ventilation for patients in different scenarios, such as mandatory ventilation modes, spontaneous ventilation modes, and assist-control ventilation modes. Ventilators monitor a variety of patient parameters and are well equipped to provide reports and other information regarding a patient's condition. To change modes and the settings therein, medical care professionals must interact directly with the ventilator.

SUMMARY

Aspects of the present disclosure relate to remotely adjusting a ventilator. A remote device (e.g., located outside of a room of a ventilator which the remote device is controlling) may receive an input at a remote user interface of the remote device to cause a settings change at the ventilator. The input may vary based on what is displayed on the remote user interface. In an example, the remote user interface may be a trackpad with an adjustment element. In this instance, the input may correlate a remote position indicator with a local ventilator position indicator. In another example, the remote user interface may replicate a portion of the ventilator GUI. In this instance, selectable elements at the remote user interface may be associated with an overlay to correlate with a selection at the ventilator.

The remote device and the ventilator may be connected via a relay transceiver. The relay transceiver may be movable between two or more ventilators. The relay transceiver may have a wired connection with a ventilator and a wireless connection with a remote device. Multiple remote devices may be capable of connecting with a single relay transceiver. Inputs at the remote device may effectuate settings changes at the ventilator using the relay transceiver.

Additionally, the remote user interface may include user interface elements associated with physical user interface element of the ventilator (e.g., a physical bezel key or a physical dial). For example, the remote user interface may include a virtual bezel key or an adjustment element. The remote user interface may be subdivided into sections or panels, such as a changeable section (e.g., changeable based on a view mode), a selection section, or an adjustment section.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Figure 1A:
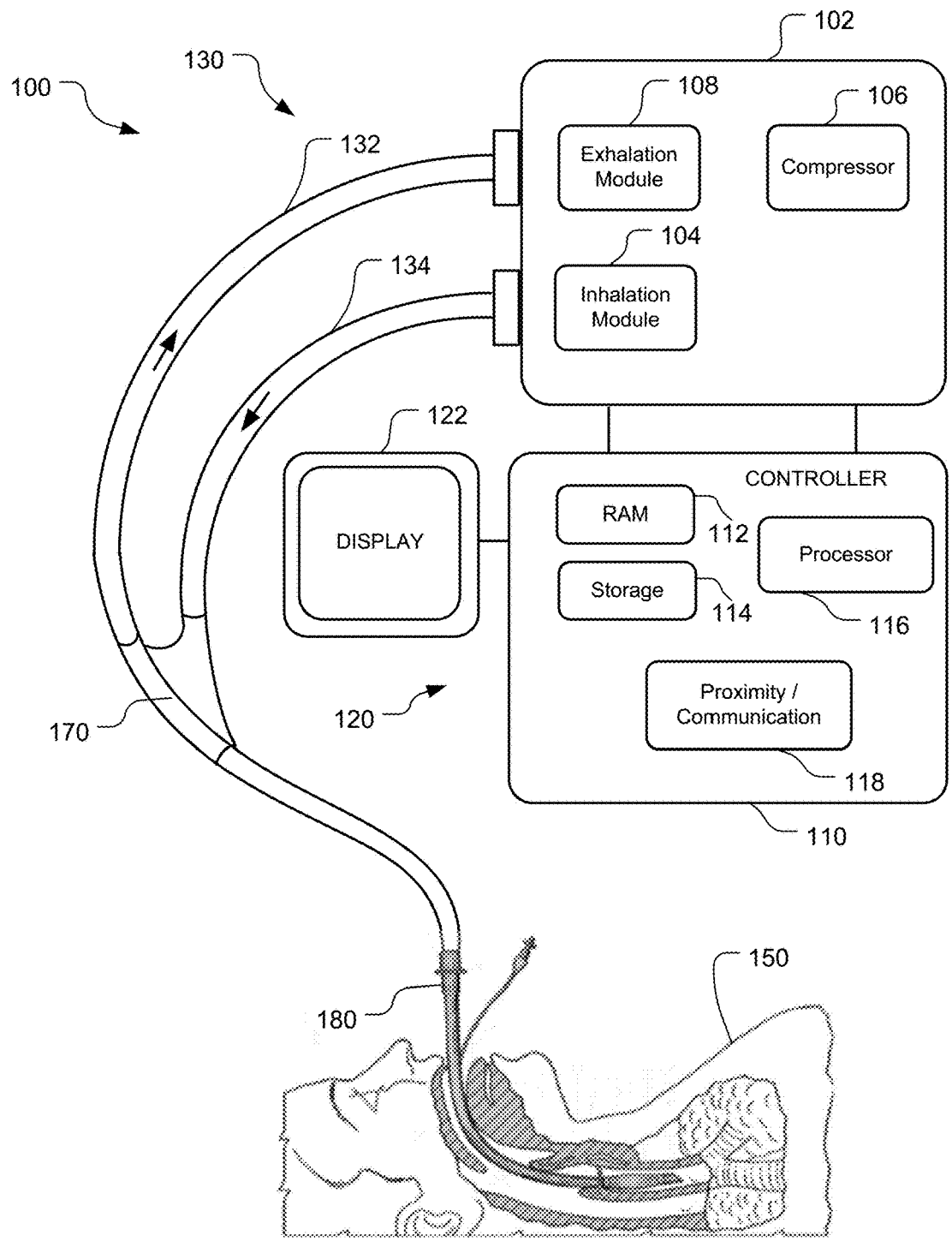
FIG. 1A depicts a diagram illustrating an example of a ventilator connected to a human patient.

While examples of the disclosure are amenable to various modifications and alternative forms, specific aspects have been shown by way of example in the drawings and are described in detail below. The intention is not to limit the scope of the disclosure to the particular aspects described. On the contrary, the disclosure is intended to cover all modifications, equivalents, and alternatives falling within the scope of the disclosure and the appended claims.

DETAILED DESCRIPTION

Ventilation provided to patients via a ventilator is controlled based, at least in part, on settings and inputs provided by a medical professional. To provide those inputs and settings, however, the medical professional must directly interact with the ventilator, such as by pressing buttons, providing touch inputs, rotating knobs or dials, etc. Directly interacting with the ventilator may present risks to the medical professional as well as the patient. For example, physically touching different ventilators increases the risk of cross-contamination and the potential spread of diseases. In addition, direct interaction with a ventilator requires physical access to the ventilator, which can be a challenge particularly in the case of patients with highly contagious diseases that may be quarantined.

The present technology looks to alleviate some of those problems by providing remote control or remote adjustment of the ventilator by a remote device. In an embodiment, the remote device receives an input at a remote user interface that is correlated or associated with a ventilator user interface displayed on the ventilator. The input may be a time-varying user input received over time. Additionally, aspects of the remote user interface on the remote device are associated with physical input components (e.g., buttons, knobs, dials, switches, etc.) on the ventilator, such that an adjustment at the remote user interface causes the same change on the ventilator user interface as a physical input. Accordingly, the ventilator may be remotely controlled by a medical professional from the remote device. By being remote from the ventilator, the medical professional does not have to physically interact with the ventilator itself.

The present technology is directly applicable to treatment of patients having highly contagious respiratory diseases, such as a coronavirus disease (COVID-19) caused by the severe acute respiratory syndrome coronavirus 2 (SARS-CoV-2). Remotely controlling a ventilator allows for the enhancement of COVID-19 patient care by: (1) increasing patient and clinician safety, (2) reducing usage of personal protective equipment (PPE), (3) providing easily accessible patient status and wellbeing information, and (4) allowing remote consultations with global experts.

First, patient and clinician safety are improved by the present technology. Clinician safety is improved by allowing a clinician to provide care to a contagious patient (e.g., a patient that contracted COVID-19) from outside of the patient's room. The clinician may therefore provide care with less exposure to contagion. Additionally, patient safety is also improved by the present technology by reducing the patient's exposure to the clinician. A clinician may interact with multiple ventilators and multiple patients throughout a hospital and may thus spread infection even when asymptomatic. Limiting the clinician's entry into a patient room reduces the risk of cross-contamination of COVID-19, or other contagious diseases, spread by a clinician.

Second, the present technology reduces usage of PPE. During a global pandemic, such as COVID-19, there can be a shortage of PPE. This is, in part, due to an increase in usage of PPE by all people (e.g., not just patient care providers) and an increase in global purchases of PPE by treatment facilities, businesses, and everyday consumers. Additionally, PPE is expensive, time-consuming to don correctly, may cause discomfort or even injury to the wearer, may impede wearer focus, and increases waste build-up due to limited reuse. Thus, reducing usage of PPE improves quality and speed of care, reduces cost, and protects the environment. Specifically, conserving PPE helps a clinician by increasing comfort and preventing lack of focus or impatience caused by uncomfortable or painful PPE, preserves the availability of PPE when needed, and reduces the risk of a clinician wearing PPE incorrectly and resulting in accidental exposure to contagious diseases. Conserving PPE helps patients by reducing delays in patient care caused by the time needed to correctly don PPE. This delay accumulates throughout the day as clinicians reposition or replace PPE, thus reducing overall time otherwise spent with patients. By allowing access to patients without requiring PPE, clinicians may be able to provide quicker patient care.

Third, the present technology reduces stress of clinicians and loved ones by providing easily accessible patient status and wellbeing information. By allowing remote viewing and control of a ventilator, clinician stress may be reduced by easily viewing ventilator settings remotely. For example, a clinician may check on multiple patients while saving time otherwise spent walking from room to room. Additionally, a view of the ventilator screen and the patient's status may be available for friends and family of a contagious patient who otherwise could not be in the room with the patient (e.g., to prevent spread).

Fourth, the present technology allows remote consultation with global experts. During a global pandemic, such as COVID-19, experts around the globe are working together to combat spread of a contagious disease. This includes experts such as COVID-19 recovery experts, ventilator diagnostic experts, vaccination and antibody experts, other clinical or medical experts (e.g., a clinical hotline), service experts (e.g., a manufacturer consult for if a ventilator appears to be malfunctioning), and product training experts (e.g., to consult with a manufacturer for training or use cases of a ventilator), etc. These experts are not located in a single treatment facility, nor are these experts located in each treatment facility. To provide the best care to COVID-19 patients world-wide, the present technology allows for remote ventilator view sharing for consultation with a variety of experts located around the world. Thus, the present technology provides a variety of advantages specific to treating COVID-19.

Beyond the pandemic scenario and COVID-19 specifically, the present technology has a variety of other practical applications for patient care. For example, the present technology may be used for patient isolation rooms, such as when a patient has or might have a communicable disease, when PPE is required to enter a room, or if the patient or equipment inside a room presents any danger to anyone entering the room. Additionally, the present technology may be used to limit direct interaction with a patient that is immunocompromised or otherwise susceptible to infection, such as a patient recovering from an organ transplant. The present technology may also be implemented when access is limited for safety, such as when a sterile procedure is being performed (e.g., limiting entry into a room while changing a wound dressing or a catheter), or when radiation is utilized (e.g., limiting exposure to a clinician in imaging rooms for computerized tomography (CT), magnetic resonance imaging (MRI), x-ray imaging, etc). Moreover, use of the present technology may also apply to areas of a hospital that have limited access due to security, such as the maternity ward or neonatal care areas (e.g., neonatal intensive care unit, NICU).

The present technology may also be implemented to limit movement in and out of a patient room and limit visible interactions with the ventilator. This may significantly reduce the stress of patients and visitors. For example, visitors may experience stress when watching a clinician adjust ventilator settings in person. By allowing the clinician to perform minor adjustments just outside of the room, stress of visiting family members and friends may be reduced. Additionally, remote ventilator viewing and adjustment allows visitors to have longer periods of uninterrupted time with the patient. This may be particularly impactful for certain patient populations, such as fragile NICU patients, or terminal patients.

The present technology can also increase the speed or daily rounds by a pulmonologist, clinician, or other assigned caregiver by reducing the amount of time otherwise required to walk from bedside-to-bedside. Additionally, the present technology may provide viewing of live data for teaching opportunities, such as for study by residents, students, ongoing clinical trials, etc. Further, the present technology provides a gateway for remote collaboration and consultation by medical teams or experts located outside of a treatment facility or far away, including longer-term care facilities, home care patients, transportation of patients between facilities (e.g., a patient being transferred or travelling via plane, helicopter, or ambulance), military care locations (e.g., temporary facilities, field hospitals, aircrafts, naval vessels, etc.), or rural care facilities (e.g., rural ICUs).

FIG. 1A depicts a diagram illustrating an example of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive (e.g., endotracheal tube, as shown) or a non-invasive (e.g., nasal mask) patient interface 180.

Ventilation tubing system 130 may be a two-limb (shown) or a one-limb circuit for carrying gases to and from the patient 150. In a two-limb example, a fitting, typically referred to as a "wye-fitting" 170, may be provided to couple the patient interface 180 to an inhalation limb 134 and an exhalation limb 132 of the ventilation tubing system 130.

Pneumatic system 102 may have a variety of configurations. In the present example, system 102 includes an exhalation module 108 coupled with the exhalation limb 132 and an inhalation module 104 coupled with the inhalation limb 134. Compressor 106 or other source(s) of pressurized gases (e.g., air, oxygen, and/or helium) is coupled with inhalation module 104 to provide a gas source for ventilatory support via inhalation limb 134. The pneumatic system 102 may include a variety of other components, including mixing modules, valves, sensors, tubing, accumulators, filters, etc.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type found in command and control computing devices. In the depicted example, operator interface 120 includes a display 122 that may be touch-sensitive and/or voice-activated, enabling the display 122 to serve both as an input and output device.

The memory 112 includes non-transitory, computer-readable hardware storage media that stores software that is executed by the processor 116 and which controls the operation of the ventilator 100. In an example, the memory 112 includes one or more solid-state storage devices such as flash memory chips. In an alternative example, the memory 112 may be mass storage connected to the processor 116 through a mass storage controller (not shown) and a communications bus (not shown).

Figure 1B:
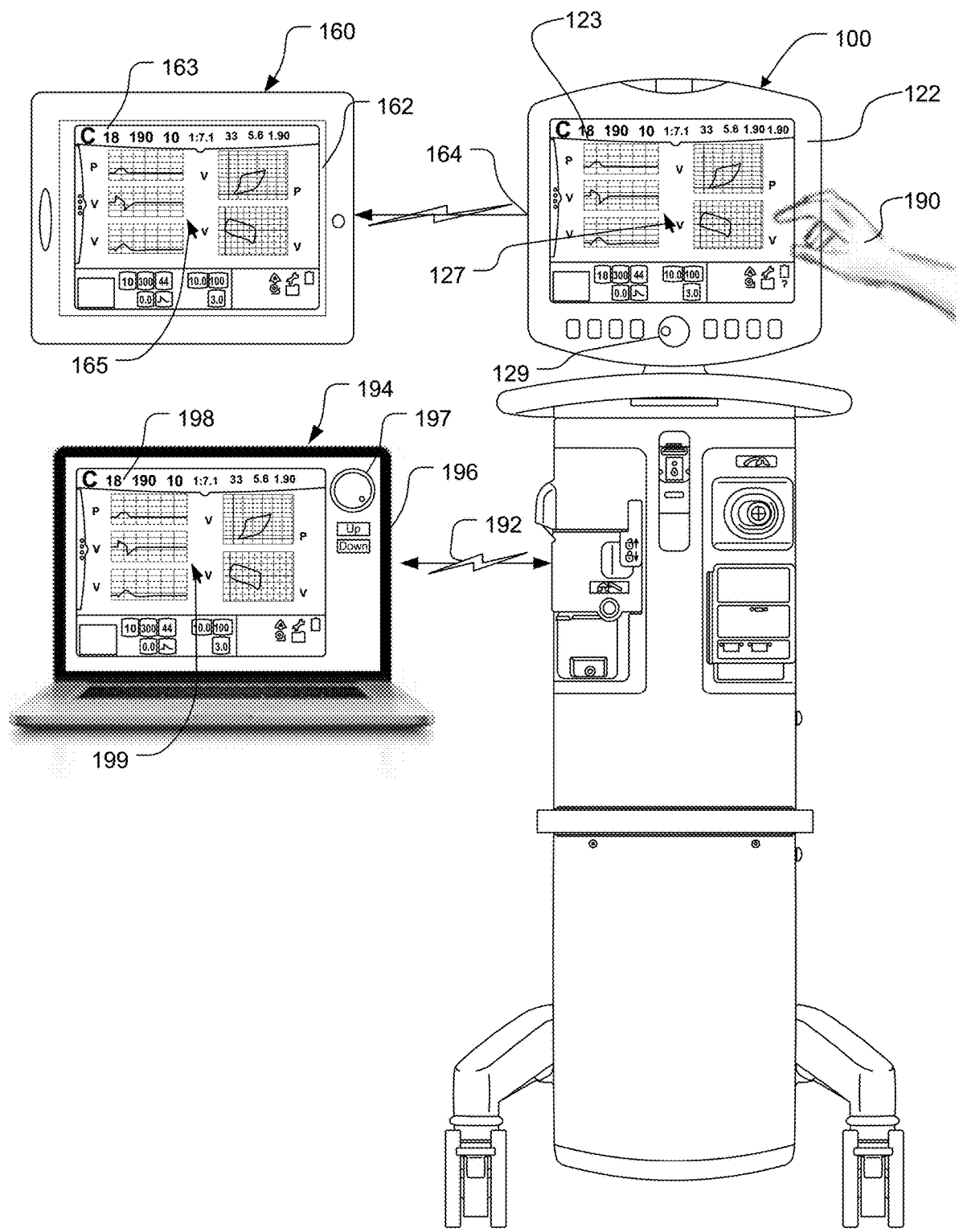
FIG. 1B depicts a diagram illustrating the ventilator of FIG. 1A, a remote display, and a remote device for adjusting the ventilator and/or viewing data from the ventilator.

FIG. 1B depicts a diagram illustrating the ventilator 100 of FIG. 1A, a first remote device 160, and a second remote device 194. The first remote device 160 and the second remote device 194 may be capable of adjusting the ventilator 100 and/or viewing data from the ventilator 100. The display 122 of the ventilator is communicatively coupled to the remainder of the ventilator components, such as memory, processors, sensors, etc. The display 122 is configured to display the ventilator graphical user interface (GUI) 123. The ventilator GUI 123 may be an interactive display, e.g., a touch-sensitive screen or otherwise, and may provide various windows (i.e., visual areas) comprising elements for receiving user input and interface command operations and for displaying ventilatory information (e.g., ventilatory data, alerts, patient information, parameter settings, etc.). The elements may include controls, graphics, charts, tool bars, input fields, icons, etc. Alternatively, other suitable means for providing input may be provided on the ventilator 100, for instance by a wheel, dial, knob, keyboard, mouse, bezel key, or other suitable interactive device. Thus, ventilator user interface 123 on the display may accept commands and input through display 122 as touch input or through other input devices. Inputs may be received by the ventilator 100 from a clinician 190.

The ventilator user interface 123 may also provide useful information in the form of various ventilatory data regarding ventilation of the patient, the physical condition of a patient, and/or a prescribed respiratory treatment. The useful information may be derived by the ventilator 100, based on data collected by sensors, and the useful information may be displayed in the form of graphs, wave representations (e.g., a waveform), pie graphs, numbers, or other suitable forms of graphic display. Additionally, the ventilator user interface 123 may provide selectable and/or adjustable ventilator control elements to select or adjust associated ventilatory settings. In an example, the ventilator control element may be an icon on the ventilator user interface 123. In another example, the ventilator control element may be a physical input at the ventilator 100.

The ventilator controls ventilation of a patient 150 according to the ventilatory settings. Ventilatory settings (or ventilation settings) may include any appropriate input for configuring the ventilator to deliver breathable gases to a particular patient, including measurements and settings associated with exhalation flow of the breathing circuit. Ventilatory settings may be entered or adjusted, e.g., by a clinician based on a prescribed treatment protocol for the particular patient, or automatically generated by the ventilator, e.g., based on attributes (i.e., age, diagnosis, ideal body weight, gender, etc.) of the particular patient according to any appropriate standard protocol or otherwise. Ventilatory settings may include inhalation flow, frequency of delivered breaths (e.g., respiratory rate), tidal volume, positive end-expiratory pressure (PEEP), etc.

The first remote device 160 may include a first remote display 162 that is capable of displaying a first remote GUI 163. Similarly, the second remote device 194 may include a second remote display 196 that is capable of displaying a second remote GUI 198. In an example, the first remote device 160 may be a tablet computer and the second remote device 194 may be a laptop computer. Other types of devices are also possible. The first remote GUI 163 and the second remote GUI 198 may replicate the ventilator GUI 123, or a portion thereof. In other examples, the first remote GUI 163 or the second remote GUI 198 may display alternate views or perspectives of the ventilator GUI 123. In some examples, the first remote GUI 163 may be different from the second remote GUI 168. The first remote display 162 and/or the second remote display 196 may be a touchscreen for receiving inputs and interactions with the first remote GUI 163 and the second remote GUI 198, respectively. In other examples, the first remote device 160 and/or the second remote device 194 may also include other input means, including voice input or other input elements such as keyboards, buttons, wheels, mouse, trackpad, bezel key, etc. for inputting data into the first remote device 160 and the second remote device 194, respectively. The first remote device 160 may establish a first wired or wireless connection 164 with the ventilator 100. Similarly, the second remote device 194 may also establish a second wired or wireless connection 192 with the ventilator 100. The first wired or wireless connection 164 and the second wired or wireless connection 192 may be any type of connection capable of transmitting data between two devices, such as radio-frequency wireless connections, cables, etc. For example, the first wired or wireless connection 164 and/or the second wired or wireless connection 192 may be a WIFI-based connection, a BLUETOOTH-based connection, an RF-LITE-based connection, a ZIG-BEE-based connection, an ultra-wideband-based connection, an Ethernet connection, a network-based connection (e.g., local area network (LAN), wide area network (WAN), etc.), an Internet-based connection, and/or an optical connection, such as an infrared-based connection.

The first wired or wireless connection 164 and the second wired or wireless connection 192 may be used to transmit data to the ventilator 100 and/or receive data from the ventilator 100 via a data signal. For example, data may be transmitted, via the first wired or wireless connection 164 and/or the second wired or wireless connection 192, from the ventilator 100 to the first remote device 160 and/or the second remote device 194. The transmitted data or data signal may be used to populate one or more of the first remote GUI 163 and the second remote GUI 198. In addition, data may be transmitted, via the first wired or wireless connection 164 and/or second wired or wireless connection 192, from the first remote device 160 and/or second remote device 194 to the ventilator 100. The transmitted data may be indicative of an input or change in a value associated with a ventilatory setting for the ventilator 100, as received as an input at the first remote device 160 or the second remote device 194. The input may be received over a period of time, or alternatively may be associated with one point in time. Accordingly, settings for the ventilator 100 may be changed remotely via the first remote device 160 and/or second remote device 194.

As an example, the first remote device 160 may display a first remote GUI 163 that is interactive, or available to receive a time-varying user input at the first remote device 160. Alternatively, the first remote device 160 may be non-interactive (e.g., the first remote GUI 163 may be limited to remote viewing of the ventilator GUI 123 without accepting any inputs or adjustments). The first remote GUI 163 may be the same (e.g., replicated) or different from the ventilator GUI 123. In an example, the first remote GUI 163 may be a virtual trackpad. In another example, the first remote GUI 163 may be a user interface that is specific to attributes of the first remote device 160. For example, the first remote GUI 163 may manipulate UI elements of the ventilator GUI 123 (e.g., change all or a portion of element size or orientation, reorganize, show a subset of elements, etc.) based on screen size, application real estate, type of device (e.g., mobile device, tablet, laptop, etc.). As another example, the first remote GUI 163 may fill all or a portion of the first remote display 162 of the first remote device 160. The second remote device 194 may display a second remote GUI 198 that may be the same or different from the first remote GUI 163. In an example, the first remote device 160 may be interactive, while the second remote device 194 may non-interactive, or display-only. In a further example, the first remote device 160 may be a tablet with a first screen size and manipulated UI elements, while the second remote device 194 may be a laptop with a second screen size replicating the ventilator GUI 123.

In an example where the first remote GUI 163 or second remote GUI 198 is capable of receiving user interaction (e.g., interactive), a time-varying user input may be received at the first remote device 160 or second remote device 194 at a first remote position indicator 165 or second remote position indicator 199, such as registered touch on a touchscreen, hovering over a touchscreen, a mouse cursor position, a trackpad cursor position, selected UI elements, etc. The first remote position indicator 165 and/or second remote position indicator 199 may be correlated with, or correspond to, a local ventilator position indicator 127 on the ventilator GUI 123. In some examples, the local ventilator position indicator 127 may be a cursor or other visual element that indicates a current selection position. The ventilator 100 may send data via a data signal to the interactive first remote device 160 and/or second remote device 194 to allow replication of portions of the ventilator GUI 123, including the local ventilator position indicator 127.

The ventilator 100 may include at least one physical input component 129. For example, the physical input component 129 may be a button, wheel, dial, slide, switch, key, etc. The physical input component 129 may be positioned or located on the ventilator 100 outside of the ventilator GUI 123. Additionally, a physical input, from a clinician, at the physical input component 129 may be associated with an adjustment of a selected ventilator control element on the ventilator GUI 123. In an example, the second remote GUI 198 may include one or more remote adjustment elements 197 correlated with or associated with a physical input at the physical input component 129. The remote adjustment elements 197 may be virtual elements that are displayed on the second remote GUI 198. The remote adjustment elements 197 may also be displayed in a format that is based on the corresponding physical input component. For instance, in the example depicted, the remote adjustment element 197 appears as a virtual dial, and the remote adjustment element may be manipulated in the same manner as a dial (e.g., a touch input to rotate the virtual dial, as may be received over time). An adjustment input associated with the remote adjustment element 197 on the second remote GUI 198, as may be a time-varying user input or alternatively associated with one point in time, may be transmitted through a data signal over the second wired or wireless connection 192 to the ventilator 100. Based on the adjustment input transmitted through an adjustment data signal, the ventilator may determine a change in a selected ventilator setting as if the physical input component 129 was physically adjusted. The remote adjustment element may be overlaid or outside of user interface elements displayed on the second remote GUI 198.

A clinician may perform an input action at the remote device (e.g., first remote device 160 and/or second remote device 194) to effectuate a change at the ventilator 100. A user action received at the remote device may be a user input (as may be a time-varying) or other user interaction, as otherwise described herein. In examples, an input action may be received at a wheel, dial, knob, keyboard, mouse, bezel key, touchpad, microphone, or other suitable interactive device associated with the remote device. Physical buttons and/or keys on a keyboard may include up or down arrows, numerical keys, mouse buttons, a mouse wheel, etc. The input action received at a suitable interactive device communicatively coupled with a remote device may then be associated with an input at the ventilator 100. For instance, an input action of selecting an up arrow on a keyboard communicatively coupled to the remote device may increase a value at the ventilator 100.

Scrolling a mouse wheel associated with the remote device may also effectuate a change at the ventilator 100. In an example, scrolling a mouse wheel associated with the remote device may increase or decrease a value at the ventilator 100. For instance, after a selection at the remote device (e.g., received at any suitable interactive device) that is associated with a selection at the ventilator 100 (e.g., selection of any user interface element on the ventilator GUI 123 and/or selection of a physical input 129 at the ventilator 100), a scroll of a mouse wheel at the remote device may change a value associated with the selection at the ventilator 100. Alternatively, a scroll of a mouse wheel associated with the remote device may change an associated value at the ventilator 100 without a prior selection at the remote device (e.g., a value associated with a current position indicator or cursor without a selection). Although a mouse wheel is described, it should be appreciated that these examples may be applied to any rotatable element, such as a physical wheel, dial, or any other variable, physical input associated with the remote device.

An input action at the remote device may also be a gesture. A gesture received at the remote device may be associated with a change at the ventilator 100. For example, the change at the ventilator 100 may be the same result as if the gesture were directly received at the ventilator GUI 123. A gesture at the remote device may be received at any of the interactive devices described herein (e.g., mouse, touchpad, touchscreen, etc.). A variety of gestures may be supported by the remote device, including a swipe, double-tap, drag, touch and hold, drag and drop, etc. One or more controls on the ventilator GUI 123 may be configurable to change in response to one or more gestures at the remote device. Gestures at the remote device may cause visual changes (or visually change) of one or more portions of the ventilator GUI 123, such as maximizing, minimizing, enlarging, shrinking, expanding, collapsing, scrolling, condensing, or otherwise augmenting the view of a portion of the ventilator GUI 123. One or more gestures at the remote device may effectuate the same or similar visual changes on one or more portions of the ventilator GUI 123. Examples of a portion of the ventilator GUI 123 that may be visually changed include a dialog, panel, waveform, tooltip, list, alarm, alarm banner, patient data, patient data panel, graph axis scale, waveform cursor, scrollbar, etc., on the ventilator GUI 123.

As an example gesture, a swipe gesture may include substantially linear movement in a specific direction. Thus, a swipe gesture includes a line with a start position and an end position. In an example, the movement associated with the swipe is rapid. A swipe at the remote device, or a swipe at the remote GUI of the remote device (e.g., first remote GUI 163 of first remote device 160 or at a second remote GUI 198 at second remote device 194), may visually change a portion of the ventilator GUI 123. In an example, a swipe toward the center of the remote GUI may open a dialog and/or panel on the ventilator GUI 123, and a swipe toward a side (e.g., right side, left side, top side, bottom side) of the remote GUI may close a dialog and/or panel on the ventilator GUI 123. The dialogs and/or panels may slide in or out from one or more sides of the ventilator GUI 123 and/or remote GUI. In another example, a paused waveform on the ventilator GUI 123 may be moved in a desired direction on the ventilator GUI 123 by a swipe at the remote device in the desired direction.

If a portion of the swipe gesture received at the remote device (i.e., a portion of the line which may include the start position and/or end position) is associated with at least a portion of a control on the ventilator GUI 123 (e.g., overlaps a control on the ventilator GUI 123), then a visual aspect of the control on the ventilator GUI 123 may change. For example, a swipe at the remote GUI, for which at least a portion of the swipe is associated with a portion of a waveform on the ventilator GUI 123, may cause a visual change of the waveform on the ventilator GUI 123. For instance, an upward swipe at the remote device that is associated with an overlap of a waveform on a ventilation GUI 123 may maximize or enlarge the waveform, while a downward swipe may minimize or shrink the waveform.

In another example, a swipe at the remote GUI, for which at least a portion of the swipe is associated with a portion of a tooltip on the ventilator GUI 123, may cause a change in the displayed description associated with the tooltip. As referred to herein, a tooltip is information related to providing assistance or help related to the ventilator 100 and/or user interface elements displayed on the ventilator GUI 123. For instance, an upward swipe at the remote device that is associated with an overlap of a tooltip on the ventilator GUI 123 may expand the tooltip description (e.g., display a longer description or open the description), while a downward swipe may collapse the tooltip description (e.g., display a shorter description or close the description).

In a further example, a swipe at the remote GUI, for which at least a portion of the swipe is associated with a portion of a patient panel on the ventilator GUI 123, may cause a change in the display of the patient panel. For instance, an upward swipe at the remote device that is associated with an overlap of a patient panel on the ventilator GUI 123 may display additional information (e.g., open the patient panel or open an additional patient panel or otherwise display additional information associated with the patient) on the ventilator GUI 123, while a downward swipe may enlarge aspects of the patient panel (e.g., display larger font).

A double-tap gesture may include two selection inputs (e.g., mouse clicks, touches, button presses, etc.) associated with a substantially same position within a shortened time or in rapid succession. A double-tap at the remote device may visually change a portion of the ventilator GUI 123 (e.g., at a position on the ventilator GUI 123 associated with the position at which the double-tap is received at the remote device). For example, a double-tap received at the remote device may maximize or minimize a portion of a waveform on the ventilator GUI 123, expand or collapse a tooltip description (e.g., as may be similar to swiping over a tooltip) on the ventilation GUI 123, display a pop-up menu on the ventilator GUI 123, etc.

A drag gesture may include an uninterrupted selection and movement. For example, a drag may include movement of a touch interaction across a touch surface without losing contact with the touch surface. The drag gesture may be similar to a swipe gesture over a longer time and/or at a slower speed. A drag gesture at the remote device may visually change a portion of the ventilator GUI 123 (e.g., at one or more positions on the ventilator GUI 123 associated with one or more positions at which the drag gesture was received at the remote device).

For example, a drag at the remote device may scroll through a list on the ventilator GUI 123 (e.g., drag upward, drag downward, drag to the right, or drag to the left, or any combination of directions). The scroll on the ventilator GUI 123 may be in the same or opposite direction of that of the drag at the remote device. The scroll speed may be based on a distance of the associated drag outside of a boundary of the list. For instance, a drag at the remote device associated with a position at the ventilator GUI 123 that is further outside the boundary of a list may cause faster scrolling of the list at the ventilator GUI 123. Scrolling on the ventilator GUI 123 may be automatic when the drag at the remote device begins at a position associated inside the list and ends at a position associated outside the list.

In another example, a drag at the remote device that is associated with an axis of a graph on the ventilator GUI 123 may change a scale of the graph axis. For instance, a drag to the right at the remote device may increase the scale of the axis of a graph on the ventilator GUI 123, a drag to the left may decrease the scale of the axis, an upward drag may increase a scale of a y-axis of the graph, a downward drag may decrease the scale of the y-axis of the graph, etc. As a further example, when a waveform is paused on the ventilator GUI 123, a drag at the remote device may move a cursor on the waveform and/or the graph of the waveform on the ventilator GUI 123.

A touch and hold gesture may include a continuous selection lapsing at least a threshold of time. For example, a touch and hold gesture may include a selection continuously received for at least 0.5 seconds. A touch and hold at the remote device may visually change a portion of the ventilator GUI 123 (e.g., at the position on the ventilator GUI 123 associated with the position at which the touch and hold is received at the remote device). For example, a touch and hold received at the remote device may display a tooltip dialog for a user interface element on the ventilator GUI 123. A tooltip dialog appearing on the ventilator GUI 123 as a result of a touch and hold at a remote device may be visually emphasized (e.g., highlighting, tinting, blinking, glowing, etc.) to indicate an association with a touch and hold gesture.

A drag and drop gesture may include an uninterrupted selection and movement (i.e., drag gesture) accompanied by a de-selection. For example, a drag and drop gesture may include receiving a touch selection, drag, and touch release at the remote device, associated with a portion of the ventilator GUI 123. A drag and drop gesture at the remote device may visually change a portion of the ventilator GUI 123 (e.g., at a position on the ventilator GUI 123 associated with a start position and/or end position at which the drag and drop is received at the remote device). For example, a drag and drop received at the remote device may visually display a help icon on the ventilator GUI 123 (e.g., dragging and dropping) onto a displayed user interface element on the ventilator GUI 123. If the help icon is "dropped" onto a user interface element on the ventilation GUI 123, a help description may be displayed (e.g., a help description associated with the user interface element onto which the help icon was dropped). Prior to "dropping" the help icon, a visual indication of whether additional information is available for the overlaid element may be displayed (e.g., the overlaid element and/or the dragged help icon may be glowing, highlighted, display a symbol or other icon, etc.).

The remote device may have a variety of configurations or may have limited components. For example, the remote device may not include a display or may not include a computer. Alternatively, the remote device may be a peripheral device for receiving a clinician's input at the remote device (e.g., mouse, keyboard, touchpad, microphone, number pads, etc.). For example, the remote device may be a peripheral device for receiving input from a clinician that sends information associated with the input to the ventilator 100.

Figure 2A:
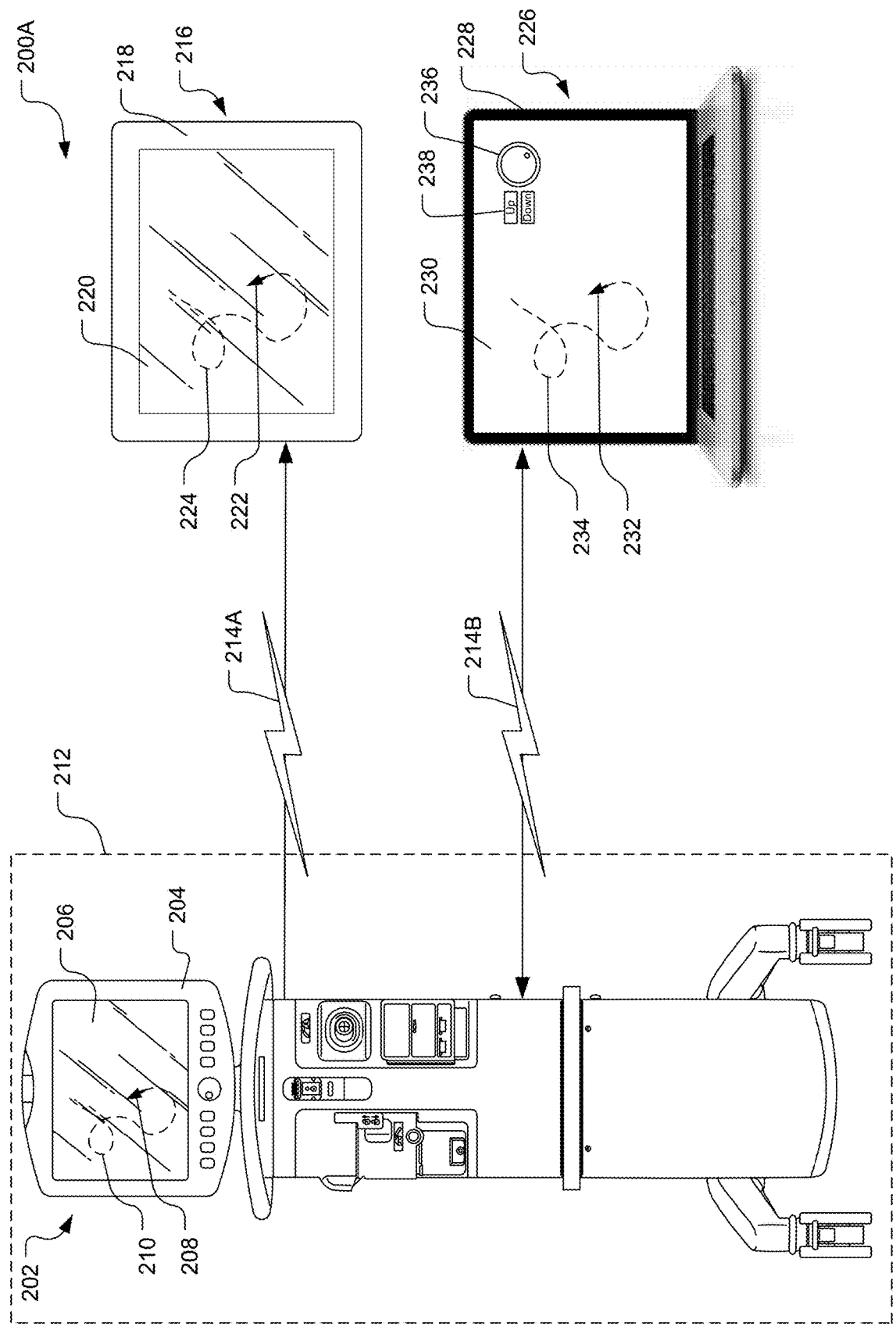
FIGS. 2A-2C depict example systems for remotely adjusting a ventilator with a remote device.

In another example, the ventilator 100 may be "headless" (e.g., have no display or GUI) and may send display information to a display device, such as replicate display device 216 in FIG. 2A. For instance, the ventilator 100 may receive information from a peripheral device (i.e., the remote device) and then send display information to a third device that may be positioned remotely from the ventilator 100 (e.g., outside of a room in which the ventilator 100 is located and/or in a different room from which the ventilator 100 is located).

Figure 1C:
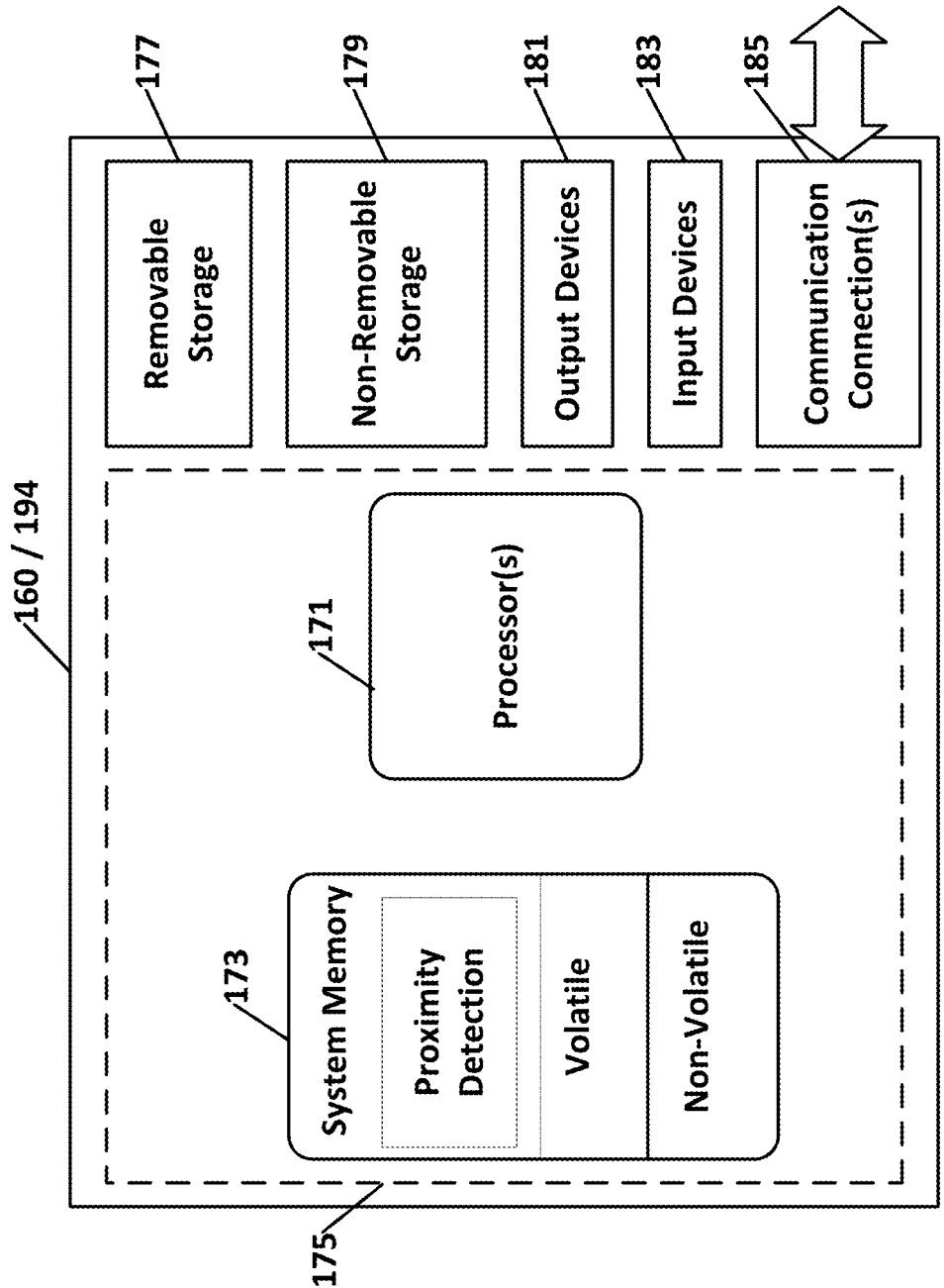
FIG. 1C depicts a schematic diagram illustrating features of the remote device.

FIG. 1C depicts a schematic diagram illustrating features of the first remote device 160 and second remote device 194. In some examples, first remote device 160 and/or the second remote device 194 may be a tablet, smartphone, laptop, or other type of computing device. The first remote device 160 may be different from the second remote device 194. In its most basic configuration, the first remote device 160 and second remote device 194 typically include at least one processor 171 and hardware memory 173. Depending on the exact configuration and type of computing device, memory 173 (storing, among other things, instructions to perform the proximity, control, and display methods disclosed herein) can be volatile (such as RAM), non-volatile (such as ROM, flash memory, etc.), or some combination of the two. This most basic configuration is illustrated in FIG. 1C is indicated by dashed line 175. Further, first remote device 160 and second remote device 194 may also include storage devices (removable, 177, and/or non-removable, 179) including, but not limited to, solid-state devices, magnetic or optical disks, or tape. Similarly, first remote device 160 and second remote device 194 can also have input device(s) 183 such as touch screens, keyboard, mouse, pen, voice input, etc., and/or output device(s) 181 such as a display, speakers, printer, etc. Also included in the environment can be one or more communication connections 185, such as LAN, WAN, point to point, Bluetooth, RF, etc.

The first remote device 160 and second remote device 194 may each be a single computing device operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments may be commonplace in hospitals, offices, enterprise-wide computer networks, intranets, and the Internet.

Figure 2B:
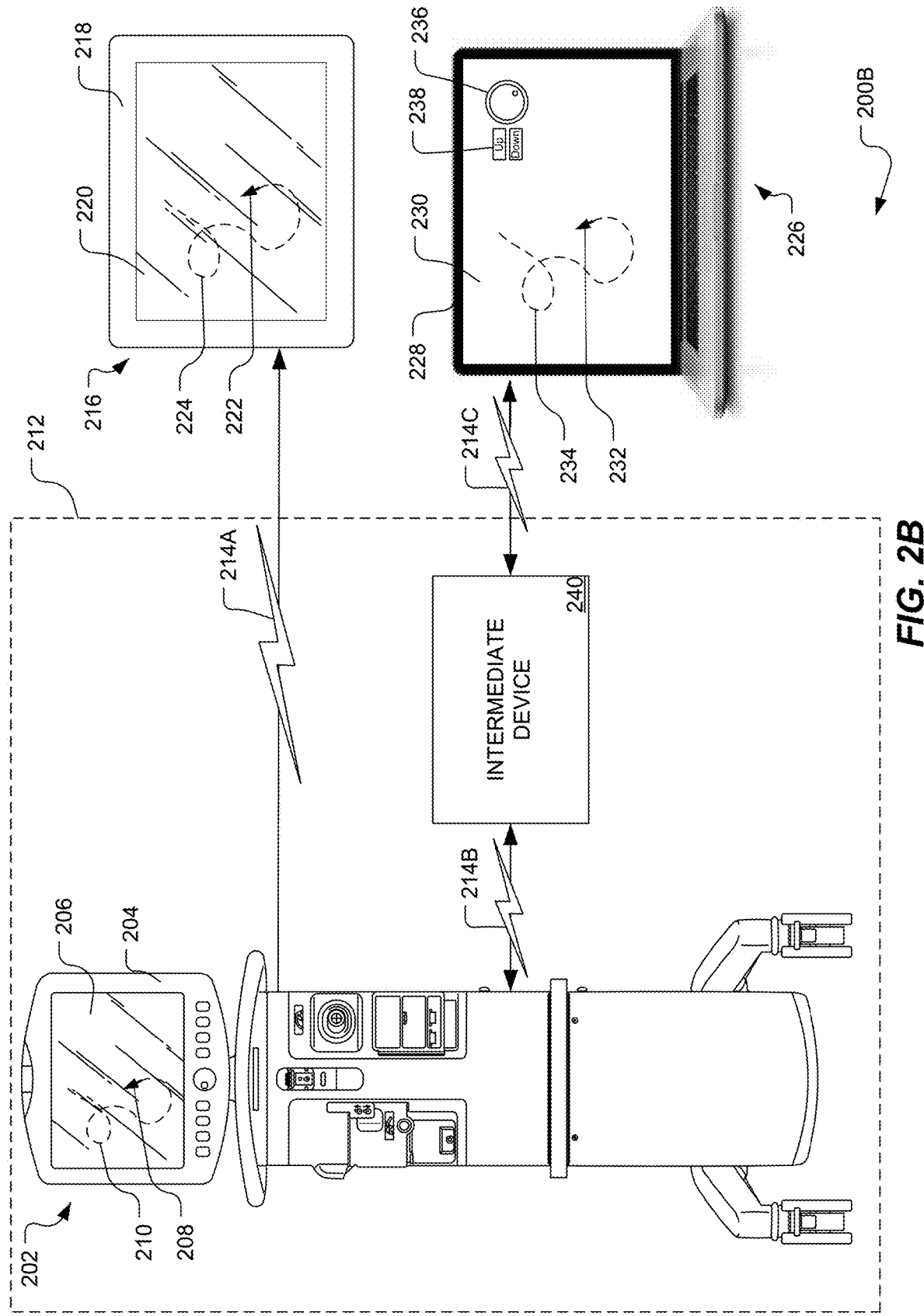
Figure 2C:
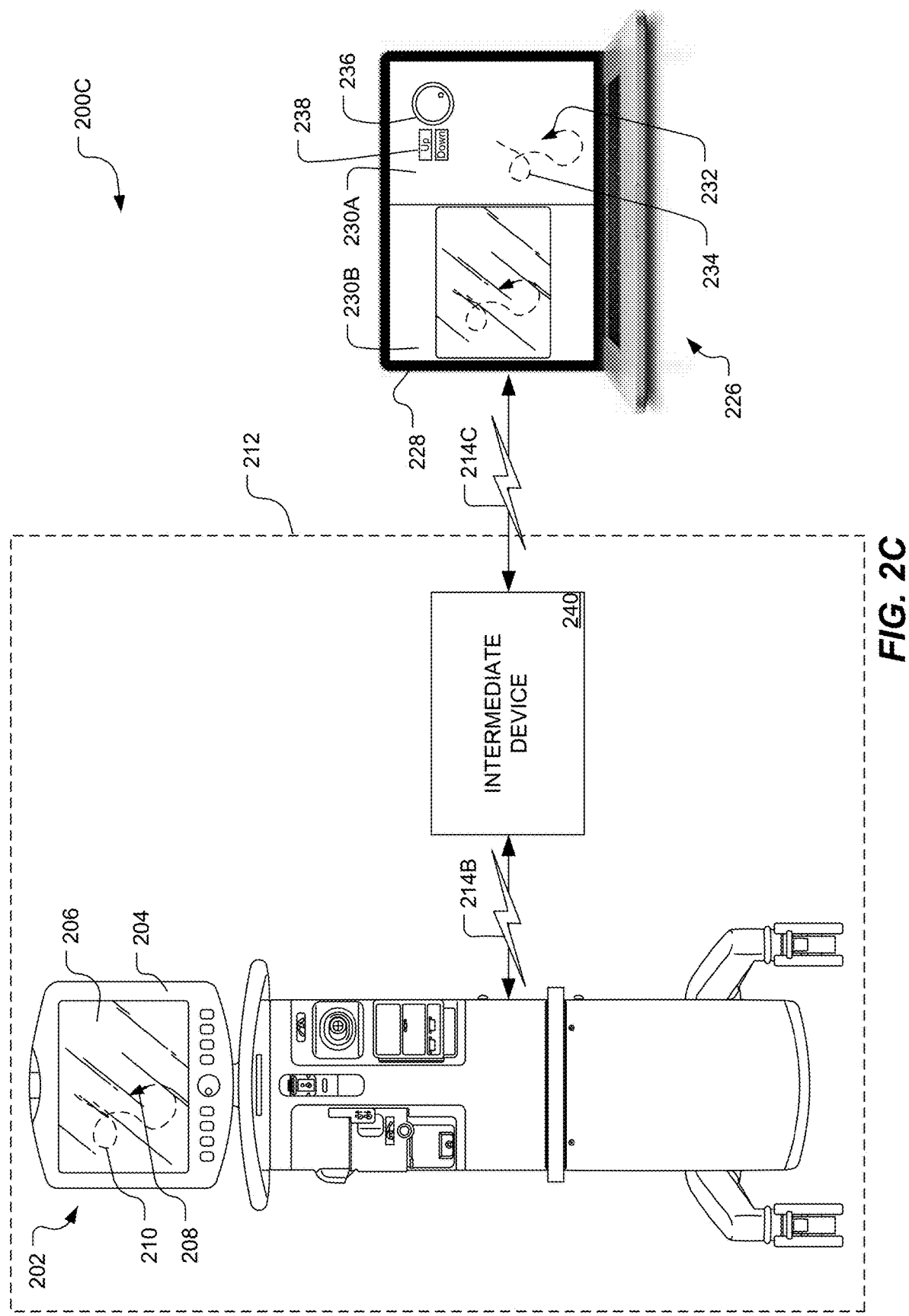

FIGS. 2A-2C depict example systems for remotely adjusting a ventilator 202 with a remote device 226. More specifically, FIG. 2A depicts an example system 200A for remote adjustment of a ventilator 202 based on an input, as may be time-varying, received at a remote device 226. The system 200A includes a ventilator 202, a replicate display device 216, and a remote device 226. The ventilator 202 may be similar to ventilator 100 described herein. For example, the ventilator 202 may include a display 204 (similar to display 122) and a ventilator GUI 206 (similar to ventilator GUI 123). The ventilator GUI 206 may include a local ventilator position indicator 208 (similar to local ventilator position indicator 127). The local ventilator position indicator 208 may also include past movement data 210. The past movement data 210 may indicate the prior position of the local ventilator position indicator 208 or a vector of prior positions of the local ventilator position indicator 208. In some sense, the past movement data 210 may effectively be a trail of the local ventilator position indicator 208. All, or a portion of, the past movement data 210 may be displayed as an indicator on the ventilator GUI 206 and/or remote GUI 230.

The ventilator 202 may be physically separated or distanced from the replicate display device 216 and/or the remote device 226 by a physical separation 212, such as a distance, a room, a wall or separator, a door, a window, a screen, etc. In an example, the ventilator GUI 123 may not be visible from the location of the remote device 226. The replicate display device 216 and the remote device 226 may be communicatively coupled to the ventilator via a first wired or wireless connection 214A and a second wired or wireless connection 214B, respectively, which may be similar to wired or wireless connections 164, 192. The first wired or wireless connection 214A and the second wired or wireless connection 214B may be different.

The replicate display device 216 includes a replicate display 218 with a replicate GUI 220. The replicate display device 216 receives data via the wired or wireless connection 214A to replicate the ventilator GUI 206, which may include a replicate position indicator 222 (replicating the ventilator position indicator 208). The replicate position indicator 222 and the ventilator position indicator 208 may be based on past movement data 210, 224. The replicate GUI 220 may replicate all or a portion of the ventilator GUI 206. Additionally or alternatively, the replicate GUI 220 may display a different view or perspective of the ventilator GUI 206 and/or display 204. In an example, the wired or wireless connection 214A between the ventilator 202 and the replicate display device 216 may be one-way such that data is transmitted from the ventilator 202 to the replicate display device 216. The replicate display device 216 may be non-interactive. As an example, the replicate display device 216 may be a television or a monitor.

The replicate display device 216 may be located outside of separation 212 or, alternatively, located proximate to the ventilator 100. In an example where the replicate display device 216 is located proximate to the ventilator 100, the replicate display device 216 may be positioned to allow visibility of the replicate display 218 from outside of the separation 212. For example, the replicate display device 216 may be mounted inside of a room of a hospital, facing outward, or alternatively mounted outside of the room. In either of these examples, the replicate GUI 220 of the replicate display device 216 may be viewable from outside of the room by a clinician using a remote device 226. In a further example, the replicate display device 216 and the remote device 226 may be proximate one another, such that a user of the remote device 226 may track the replicate position indicator 222 on the replicate GUI 220 (replicated from the local ventilator position indicator 208 on the ventilator GUI 206) as the user moves the trackpad (also moving the remote position indicator 232).

The remote device 226 may include a remote display 228 with a remote GUI 230. The remote device 226 may be similar to the remote devices 160, 194 described in FIGS. 1B and 1C. For example, the remote GUI 230 may include a remote position indicator 232 based on remote past movement data 234. The remote GUI 230 may also include a first remote adjustment element 236 and a second remote adjustment element 238, which may allow a virtual adjustment of a physical input component 129 of the ventilator 100. For example, first remote adjustment element 236 and the second remote adjustment element 238 may be a variety of inputs, including a virtual numerical input, a slider bar, a dial, a wheel, an arrow, an up/down control, a voice input, a haptic input, etc. While the remote adjustment element 236 and the second remote adjustment element 238 are generally virtual elements displayed in a GUI, in some examples, the remote adjustment element 236 and/or the second remote adjustment element 238 may be a physical element (such as a physical dial) that is incorporated on the remote device 226. In an example, the first remote adjustment element 236 and the second remote adjustment element 238 may be different. For example, the first remote adjustment element 236 may be a dial and the second remote adjustment element 238 may be up/down controls.

In use, the remote device receives position and selection input from a user which corresponding to a ventilator setting. That position and selection input is sent to the ventilator, which causes the ventilator setting to be selected. Once that setting is selected, the user can interact with the remote adjustment elements 236, 238 to adjust the setting. The interactions with the remote adjustment elements are transmitted as adjustment data to the ventilator to change the setting.

Additionally or alternatively to the first remote GUI 163 or the second remote GUI 198 described in FIG. 1B, the remote GUI 230 of the remote device 226 may include a virtual trackpad. In an example where the remote GUI 230 is, or includes, a virtual trackpad, the remote GUI 230 may include a portion of the remote GUI 230 to appear blank or otherwise lack any user interface elements. As an example, all or a portion of the elements displayed on the replicate GUI 220 may be displayed on a portion of the remote GUI 230. In an example, a portion of the replicate GUI 220 may be displayed on the remote GUI 230 adjacent to a trackpad. The virtual trackpad may allow for a remote position indicator 232 on the remote device 226 to be correlated with the local ventilator position indicator 208 on the ventilator 202. The correlated position information, based on a position input, may be sent to the ventilator 202 over the wired or wireless connection 214B. The position input may be a time-varying user input.

Correlation of the remote position indicator 232 with the local ventilator position indicator 208 may be determined based on a one-to-one overlay and/or may be movement-based. In an example where the direct correlation is an overlay, there may be a one-to-one mapping of x-y coordinates on the remote GUI 230 with x-y coordinates on the ventilator GUI 206. As a further example, a one-to-one overlay may occur where the ventilator GUI 206 is replicated on the remote GUI 230 of the remote device 226. Accordingly, an input at a remote position indicator 232 on the remote GUI 230 may have a direct correspondence with a local ventilator position indicator 208 on the ventilator GUI 206. In an example where the direct correlation is movement based, remote past movement data 234 on the remote GUI 230 may be associated with a local ventilator past movement data 210. For example, the local ventilator position indicator 208 may change location or position on the ventilator GUI 206 based on the remote past movement data 234, irrespective of an x-y coordinate of the remote past movement data 234. For instance, the starting position of the remote past movement data 234 may be zeroed for the local ventilator position indicator 208. As an example, dragging the remote position indicator 232 on the virtual trackpad causes a corresponding movement of the local ventilator position indicator 208.

The features of the remote GUI 230 may have various advantages. For example, the use of a virtual trackpad allows for the transmission of position and click (or gesture) information, rather than commands for specific setting types and values for those settings. Additionally, correlation of inputs to a virtual trackpad may reduce translation requirements and errors in data signals sent from the remote device 226 to the ventilator 202, because the remote device is responsible only for the trackpad data (positions, clicks, gestures) and not specific ventilator settings such as breath modes, etc. (for which the ventilator remains responsible). As another example, a virtual trackpad may not need to be device-specific and may have a faster learning curve for users. Alternatively, a remote GUI with user interface elements (such as the remote GUI 198 described in FIG. 1B) may also have advantages. For example, a remote GUI with user interface elements may not require a replicate display device 216 and may lower the amount of time and/or energy of a user comparing an input with a replicate display 218 to understand what is happening on the ventilator 202. Thus, aspects of the present technology may include one or more features of each example of the remote GUI 230, 163.

In the system 200A shown in FIG. 2A, the remote device 226 may receive an input associated with the remote GUI 230. The input may be a movement of the remote position indicator 232 over time, a selection input at the remote position indicator 232 at a position, an adjustment input of a remote adjustment element 236, 238 at the remote position indicator 232 over time or at one point in time, or any other user input at the remote GUI 230. The remote position indicator 232 may be displayed on the remote GUI 230. The remote device 226 may determine input information to send to the ventilator 202 over the connection 214B. The input information may include remote position and/or coordinate information, movement information, selection information, or adjustment information, based on the input received at the remote device 226. The ventilator 202 may receive the input information and determine an associated ventilator input. For example, the ventilator input associated with movement information may be moving a local ventilator position indicator 208 displayed on the ventilator GUI 206. As another example, the ventilator input associated with selection information may be selecting a ventilator control element displayed on the ventilator GUI 206. As a further example, the ventilator input associated with adjustment information may be adjusting a value or values associated with a selected ventilator control element.

The ventilator may update one or more ventilation settings associated with the ventilator input, and/or update the ventilator GUI 206 based on the ventilator input (e.g., moving a local ventilator position indicator 208, selecting a ventilator control element on the ventilator GUI 206, or adjusting a selected ventilator control element). As the ventilator 202 updates the ventilator GUI 206, the ventilator 202 may send update information to the replicate display device 216 and/or the remote device 226 over the wired or wireless connections 214A, 214B. The update information may include display information used to replicate all or a portion of the ventilator GUI 206 and/or value information associated with a change in a value of a selected ventilator control element. The display information may include local ventilator position indicator 208. The local ventilator position indicator 208 may be displayed on the ventilator GUI 206 and/or the replicate GUI 220. In an example, the local ventilator position indicator 208 may be displayed on the replicate GUI 220, but not the ventilator GUI 206.

In an example, the remote device 226 and/or replicate display device 216 may be dedicated to, or specific to, one ventilator 202, or may be capable of communicating with a plurality of ventilators 202 over one or more separations 212. In this example, the remote device 226 may be portable. The remote device 226 and/or replicate display device 216 may also be a part of a central monitoring system communicatively coupled with a plurality of ventilators in one or more facilities. In another example, the replicate display device 216 may be specific to one ventilator 202 while the remote device 226 may be capable of communicating with multiple ventilators. As a further example, the remote device 226 may be specific to one ventilator 202 while the replicate display device 216 may be capable of receiving display information from multiple ventilators. In a further example, both the replicate display device 216 and the remote device 226 are specific to one ventilator 202.

FIG. 2B depicts another example system 200B for remote adjustment of a ventilator 202 based on a time-varying user input received at a remote device 226. System 200B is similar to system 200A, with the exception of an intermediate device 240, such as a relay transceiver or remote-control accessory, which may be located communicatively between the ventilator 202 and the remote device 226 to relay communications. The intermediate device 240 may have similar computing components as remote devices 160, 194, 226 described in FIGS. 1B, 1C, and 2A. Intermediate device 240 may be proximate to the ventilator 202, such as located inside the separation 212. Intermediate device 240 may receive data from remote device 226 over wired or wireless connection 214C. The intermediate device 240 may then relay the data to the ventilator 202 over wired or wireless connection 214B. The intermediate device 240 may act as a relay and/or translator to process or translate the data received from the remote device 226 prior to relaying processed data to the ventilator 202. For instance, the intermediate device 240 may translate the selection and position information received from the remote device 226 into a format that can be processed by the ventilator 202. In another example, the intermediate device 240 may be controlled by the remote device 226 similar to how the remote device 226 controls the ventilator 202 in FIGS. 1B and 2A. In an example, the intermediate device 240 may be specific to one ventilator 202 or may be capable of communicating with multiple ventilators 202. In another example, the intermediate device 240 is specific to one ventilator 202 while the remote device 226 may be capable of communicating with multiple ventilators 202 via multiple intermediate devices 240. For example, a first ventilator may have a wired connection with a first intermediate device and a second ventilator may have a wired connection with a second intermediate device and a remote device may be capable of controlling the first intermediate device and the second intermediate device via a wireless connection. In a further example, the intermediate device 240 may have a wired connection 214B with the ventilator 100 to facilitate a wireless connection 214C between the intermediate device 240 and the remote device 226.

FIG. 2C depicts another example system 200C for remote adjustment of a ventilator 202 based on a time-varying user input received at a remote device 226. System 200C is similar to system 200B, with the exception of no replicate display device 216 and the remote GUI 230 including a remote trackpad GUI 230A and remote replicate display GUI 230B side by side on the same display. In this example, the replicate GUI 220 may be displayed on the remote replicate display GUI 230B, thus rendering a replicate display device 216 redundant. In this system 200C, as the ventilator 202 updates the ventilator GUI 206 (concurrently or after updating), the ventilator 202 may send update information (e.g., display information and/or value information) to the intermediate device 240 over the wired or wireless connection 214B, which may relay the update information to the remote device 226 over the wired or wireless connection 214C.

Figure 3:
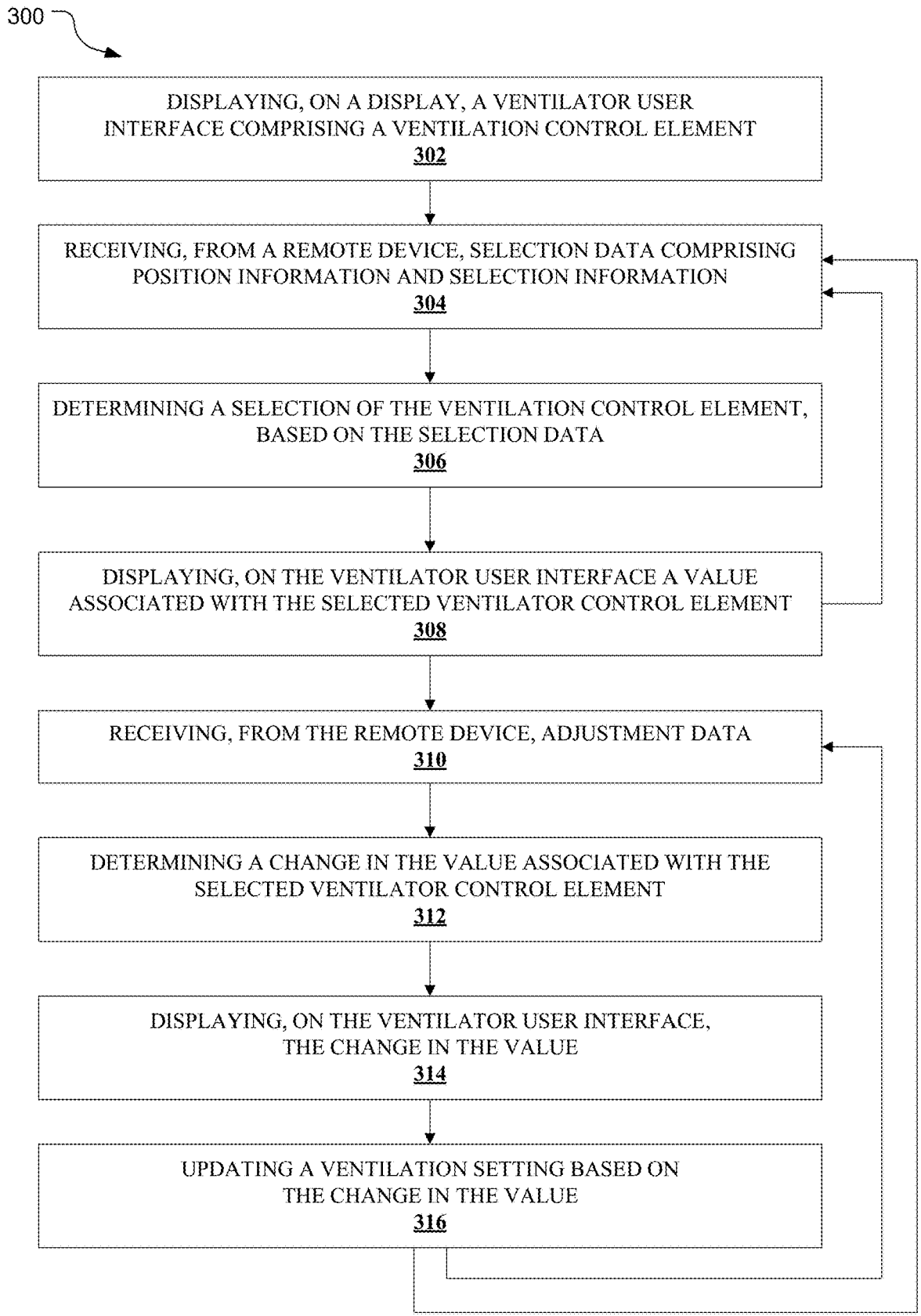
FIG. 3 depicts an example method for remotely adjusting a ventilator based on a time-varying user input received at a remote device.

FIG. 3 depicts an example method 300 for remotely adjusting a ventilator (e.g., ventilator 100, 202) based on a time-varying user input received at a remote device (e.g., remote device 160, 194, 226). The operations of method 300 may be performed by the ventilator and/or other components described in the above systems. At operation 302 the ventilator displays, on a display (e.g., display 122, 204), a ventilator user interface (e.g., ventilator GUI 123, 206) comprising a ventilator control element. There may be a plurality of ventilator control elements each associated with different ventilation settings. For example, a ventilator control element may be a graphical element for adjusting settings or entering data. For example, the settings or data may include a new patient entry, a stored patient entry, setup information (such as predicted body weight, gender, height, or other patient information), ventilation type (e.g., invasive, NIV, $HFO_2T$), mode (e.g., A/C, SIMV, SPONT, BiLevel, CPAP), mandatory type (e.g., PC, VC, VC+), spontaneous type (e.g., PS, TC, VS, PAV+), trigger type (e.g., P-Trig, V-Trig, IE Sync), respiratory rate (f), tidal volume ($V_T$), peak inspiratory flow ($\dot{V}_{MAX}$), flow sensitivity ($\dot{V}_{SENS}$), oxygen concentration ($O_2$%), peak circuit pressure ($P_{PEAK}$), plateau time ($T_{PL}$), positive end-expiratory pressure (PEEP), rise time percent (~P), inspiratory time ($T_I$), inspiratory pressure ($P_1$), start ventilation control, cancel control, alarm settings, menu control, or any other selectable or controllable user interface element that may be display on a ventilator user interface. As a further example, the ventilator control element on the ventilator GUI may be another type of user interface element, such as an icon, a control, a checkbox, a radio button, a dropdown list, a button, a toggle, a text field, a slider, a page tab, a search field, a tag, etc. In an example (as further shown in FIGS. 5A and 5B), the ventilator control element may be an icon representing inspiratory time ($T_I$). The ventilator control element representing inspiratory time may be selectable and include an adjustable value. For example, the value associated with the inspiratory time may be 0.40 seconds.

At operation 304, the ventilator receives, from a remote device, selection data including position information and selection information. In an example, the selection data may be received over a wired or wireless connection (such as connections 164, 192, 214A, 214B, 214C). As an example, the position information may be associated with a remote position indicator (such as remote position indicators 165, 199, 232) and/or a local ventilator position indicator (such as local ventilator position indicators 127, 208). As described herein, the position information may be correlated between coordinates of the remote device user interface and the ventilator user interface. Selection information may be any information associated with a selection (e.g., activation or click) of a ventilator user interface element at the position indicated by the position information. It should also be appreciated that the ventilator may receive separate data for position information and/or selection information. In an example, position data may include position information related to a change in position of a remote position indicator (such as a movement shown by past movement data 210 and/or remote past movement data 234). The position information may or may not be associated with selection information (e.g., when a remote position indicator moves without a selection). In another example, selection data may include selection information without position information (e.g., when a mouse is clicked without moving). In this example, the selection information may be associated with a current position indicator on the ventilator.

At operation 306, the ventilator determines a selection of the ventilator control element based on received selection data. For example, if the position information and the selection information associated with a local ventilator position indicator are associated with (correspond with or are correlated with) coordinates of a ventilator control element on the ventilator user interface, then the associated ventilator control element may be selected by the ventilator. As a further example, a ventilator control element representing inspiratory time ($T_I$) may be associated with a set of coordinates or a region on the ventilator GUI. In this example, the ventilator control element representing inspiratory time is selected when the position information of the selection is associated with the set of coordinates of region on the ventilator GUI associated with the ventilator control element.

At operation 308, the ventilator displays, on the user interface, a value associated with the selected ventilator control element. In a further example, the ventilator may also display an indication of the selected ventilator control element. An indication of the selected ventilator control element may include bolding, highlighting, blinking, resizing, replicating, or any other form of emphasizing the ventilator control element. The value associated with the selected ventilator control element may be a selectable, scalable, adjustable, or otherwise variable. The value may be displayed on, or as a part of, the ventilator control element. Additionally or alternatively, the value may be displayed in another location on the user interface of the ventilator. In another example, a local ventilator position indicator may be displayed. Continuing the above example where the ventilator control element represents inspiratory time ($T_I$), the ventilator control element may be emphasized on the ventilator GUI, for example by bolding, highlighting, etc., and the value of 0.40 seconds associated with the inspiratory time may be adjustable.

At operation 310, the ventilator receives, from the remote device, adjustment data. The adjustment data is generated from interactions with the remote adjustment elements (e.g., dial, up/down buttons). The adjustment data is associated with the selected ventilator control element. The adjustment data may be correlated with an adjustment on the ventilator (via the user interface, or via physical input at a physical input component, such as physical input component 129) and an adjustment on the remote device. For instance, rotation of the virtual dial generates adjustment data that may correspond to the same type of rotation on the physical dial of the ventilator.

At operation 312, based on the adjustment data, the ventilator determines a change in the value associated with the selected ventilator control element. Continuing the example where the ventilator control element represents inspiratory time ($T_I$), the value may be adjustable at the ventilator based on a physical input at a physical input component (such as an angle of rotation of a dial). The adjustment information may be associated with a virtual rotation of a virtual dial (as received at the remote device via a time-varying user input, transmitted through selection data and/or adjustment data), which may correspond with the physical input at the physical input component on the ventilator. Thus, the adjustment data may correspond with a change in the value (e.g., an inspiratory time of 0.40 seconds may be changed to 0.30 seconds).

At operation 314, the ventilator displays, on the user interface, the change in the value. For example, the ventilator may show the change by displaying the updated/ changed value, the previous value, a change or difference in the value, or a combination. Additionally or alternatively, the updated value may be associated with an indication that the value was changed. Continuing the example where the ventilator control element represents inspiratory time ($T_I$), and the value is changing from 0.40 seconds to 0.30 seconds, the ventilator may display the new value (0.30 seconds), an indication that the value recently changed, the prior value (0.40 seconds), and/or the change in the value (0.10 seconds). At operation 316, the ventilator updates a ventilation setting based on the change in the value. Ventilation settings, or ventilatory settings, are described further in FIG. 1A. For example, the ventilator may update the inspiratory time, or the time that flow is commanded into the breathing circuit, from 0.40 seconds to 0.30 seconds. Ventilation of the patient is then provided based on the changed value(s) for the ventilation setting(s).

One or more operations of method 300 may repeat. For example, operations 304-308 may repeat as new selection data is received from the remote device. For example, the ventilator may de-select the ventilator control element associated with inspiratory time ($T_I$) and may instead select a ventilator control element associated with PEEP. As another example, operations 310-216 may repeat as different adjustment data is received from the remote device for a same selected ventilator control element. For example, the ventilator may receive a further adjustment to the inspiratory time value, such as further changing the value from 0.30 seconds to 0.35 seconds, in the above example. In a further example, operations 304-316 may repeat for new selection data and associated adjustment data received from the remote device for a different selected ventilator control element. For example, the ventilator may de-select the ventilator control element associated with inspiratory time ($T_I$) and may instead select a ventilator control element associated with PEEP, thereafter receiving adjustment data to adjust the value associated with the PEEP ventilator control element.

Figure 4:
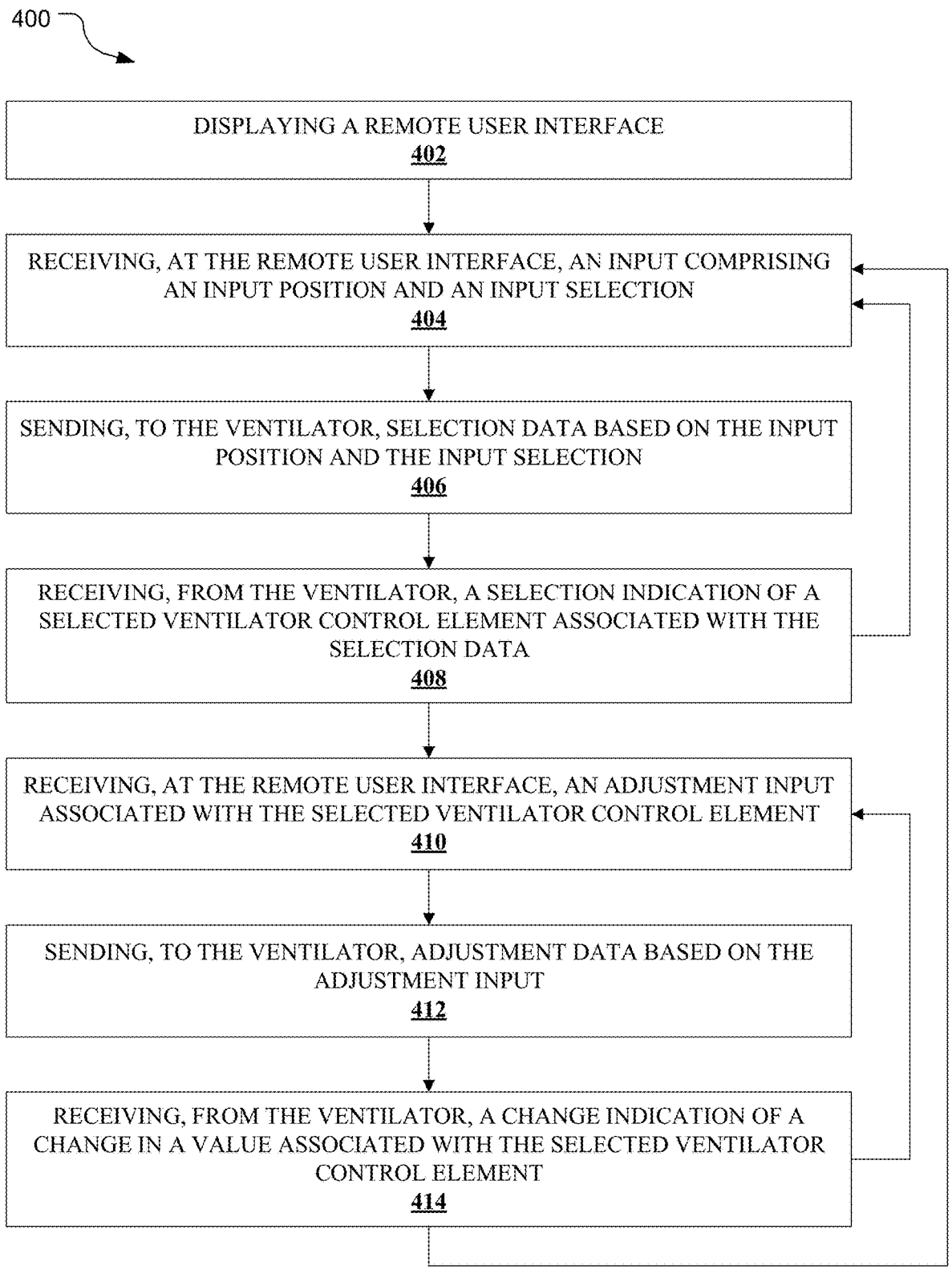
FIG. 4 depicts another example method for remotely adjusting a ventilator based on a time-varying user input received at a remote device.

FIG. 4 depicts a method 400 for remotely adjusting a ventilator (such as ventilators 100, 202) based on an input received at a remote device (e.g., remote devices 160, 194, 226). The operations of method 400 may be performed by the remote device and/or other components described in the above systems. At operation 402, the remote device may display a remote user interface (such as remote GUIs 163, 198, 230). The remote user interface may include a virtual trackpad, a remote replicate display (which may be interactive) which may show one or more features of a ventilator user interface, a remote adjustment element, or any combination thereof, as described herein. In an example, the remote adjustment element may be a virtual dial associated with a physical dial on the ventilator.

At operation 404, the remote device receives, at the remote user interface, an input comprising an input position, with associated position information, and an input selection, with associated selection information. The input may be received at a touchscreen of the remote user interface, or otherwise received via user interaction with the remote device. The input position may be associated with the remote position indicator (such as remote position indicators 165, 199) on the remote user interface of the remote device. At operation 406, the remote device may send to the ventilator, selection data based on the input position and the input selection. In an example (as further shown in FIGS. 5A and 5B), the selection received at the remote device may correspond with a ventilator control element on the ventilator GUI.

At operation 408, the remote device may receive, from the ventilator, a selection indication of a selected ventilator control element associated with the selection data. In an example where the remote user interface includes a replicate display including the ventilator control element, the replicate display may be updated based on the selection indication.

In another example, the selection indication may cause the remote device to allow adjustment to a remote adjustment element (such as remote adjustment element 236, 238). As a further example, the remote adjustment element may (e.g., virtual dial) be disabled when the selection indication indicates that a ventilator control element is not selected (e.g., upon receiving a de-selection indication or prior to receiving a selection indication), and enabled when the selection indication indicates that the ventilator control element is selected.

Continuing the above example where the selected ventilator control element represents inspiratory time ($T_I$), the remote GUI may display an indication that "inspiratory time" is selected and/or display the current value of 0.40 seconds. The virtual dial may be enabled after receiving a selection indication of a selected ventilator control element from the ventilator. The virtual dial may be disabled when there is no ventilator control element selected at the ventilator (as determined from one or more selection indications received from the ventilator).

At operation 410, the remote device receives, at the remote user interface, an adjustment input associated with the selected ventilator control element (e.g., virtual dial). The adjustment input may be received via user interaction with a remote adjustment element (such as remote adjustment elements 236, 238) at one time or over a period of time. Additionally, or alternatively, the adjustment input may be received as a variety of input forms, such as numerical, slide, dial, wheel, arrow, up/down control, voice, haptic, etc. The adjustment input is associated with a change in a value associated with the selected ventilator control element. A greater change in the adjustment input (e.g., larger rotation of the dial) may be associated with a greater change in the value. The adjustment input may also be a scroll of a mouse wheel or a swipe of a screen via touch input.

At operation 412, the remote device sends, to the ventilator, adjustment data based on the adjustment input. Continuing the above example where the ventilator control element represents inspiratory time ($T_I$), the adjustment input may be a rotation of a virtual dial on the remote GUI over time to change the inspiratory time value as if a physical dial were being rotated on the ventilator. In an example, the change in the value may be based on the angle of rotation of the virtual dial, with a positive or negative angle indicating direction. For example, the rotation of the virtual dial may include position and selection information associated with the virtual dial over a period of time. Alternatively, the adjustment input may be a selection of an adjustment icon (e.g., Up/Down icon) at a point in time. In this example, each selection of the adjustment icon may change the value by a predetermined amount, such that more selections of the adjustment icon (or selecting the adjustment icon over a period of time) may result in a greater change in the value.

At operation 414, the remote device may receive, from the ventilator, a change indication of a change in a value associated with the selected ventilator control element. Based on the change indication, the remote device may show, on the remote user interface, the updated/changed value, the previous value, a change or difference in the value, or a combination. Continuing the above example where the ventilator control element represents inspiratory time ($T_I$), the change indication may include information that the value associated with inspiratory time has changed (e.g., from 0.40 seconds to 0.30 seconds). The remote GUI may display the new value (0.30 seconds), an indication that the value recently changed, the prior value (0.40 seconds), and/or the change in the value (0.10 seconds).

One or more operations of method 400 may repeat. For example, operations 404-408 may repeat as a new selection or position input is received at the remote device. For example, the remote device may send a de-selection to de-select the ventilator control element associated with inspiratory time ($T_I$). Alternatively, a selected ventilator control element may be automatically de-selected upon receiving selection data at the ventilator to select a different ventilator control element (e.g., associated with PEEP). As another example, operations 410-414 may repeat as different adjustment inputs are received at the remote device for a same selected ventilator control element. For example, the remote device may receive a further adjustment input to the inspiratory time value, such as further rotating a virtual dial to change the value at the ventilator from 0.30 seconds to 0.35 seconds, in the above example. In a further example, operations 404-414 may repeat for new selection inputs, new position inputs, and new adjustment inputs received at the remote device for a different selected ventilator control element. For example, the remote device may send selection data to de-select the ventilator control element associated with inspiratory time ($T_I$), and instead select a ventilator control element associated with PEEP. The adjustment input may then adjust a value associated with a ventilator control element representing PEEP.

Figure 5A:
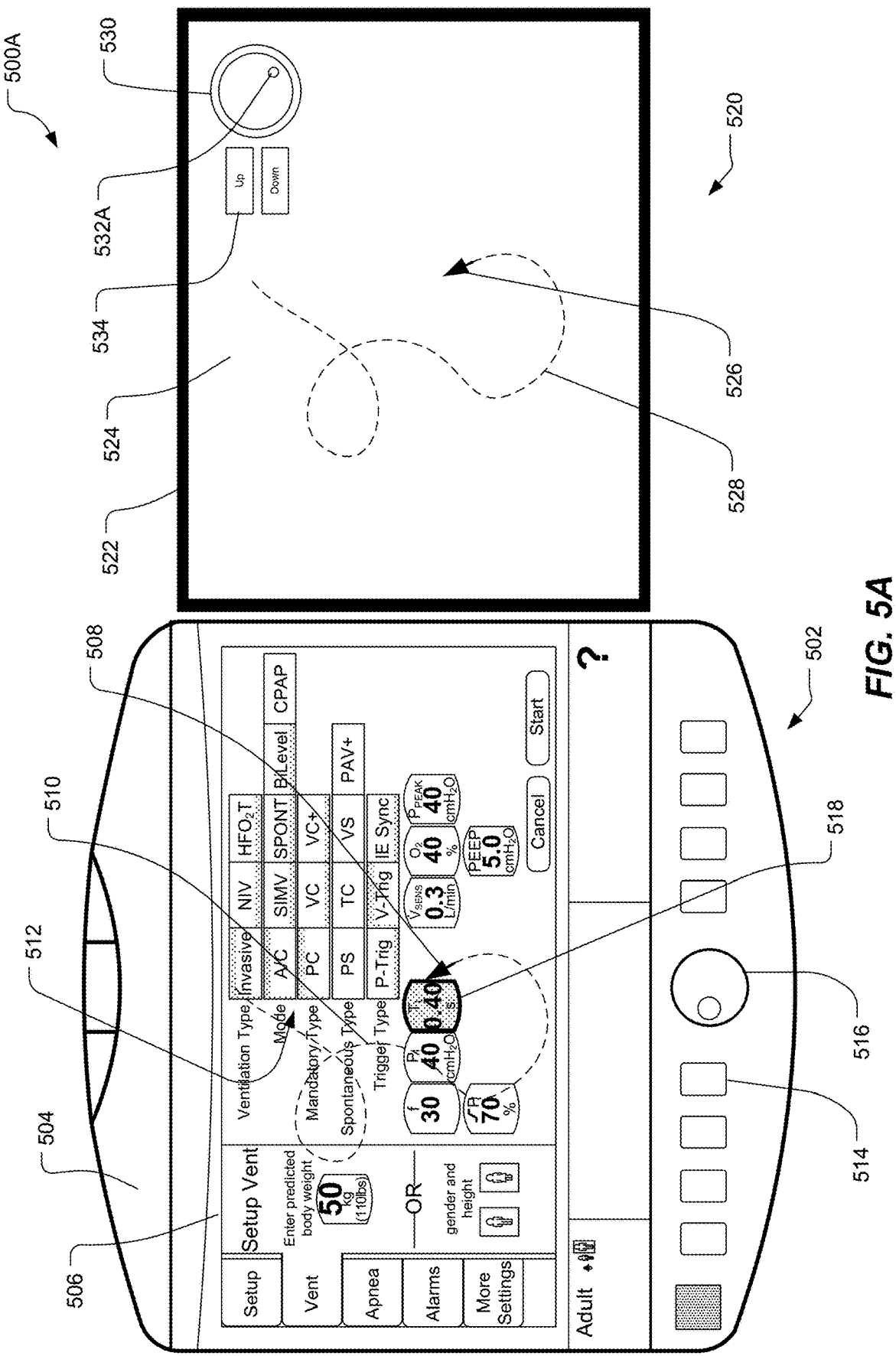
FIGS. 5A and 5B depict example user interfaces of a ventilator and a remote device.
Figure 5B:
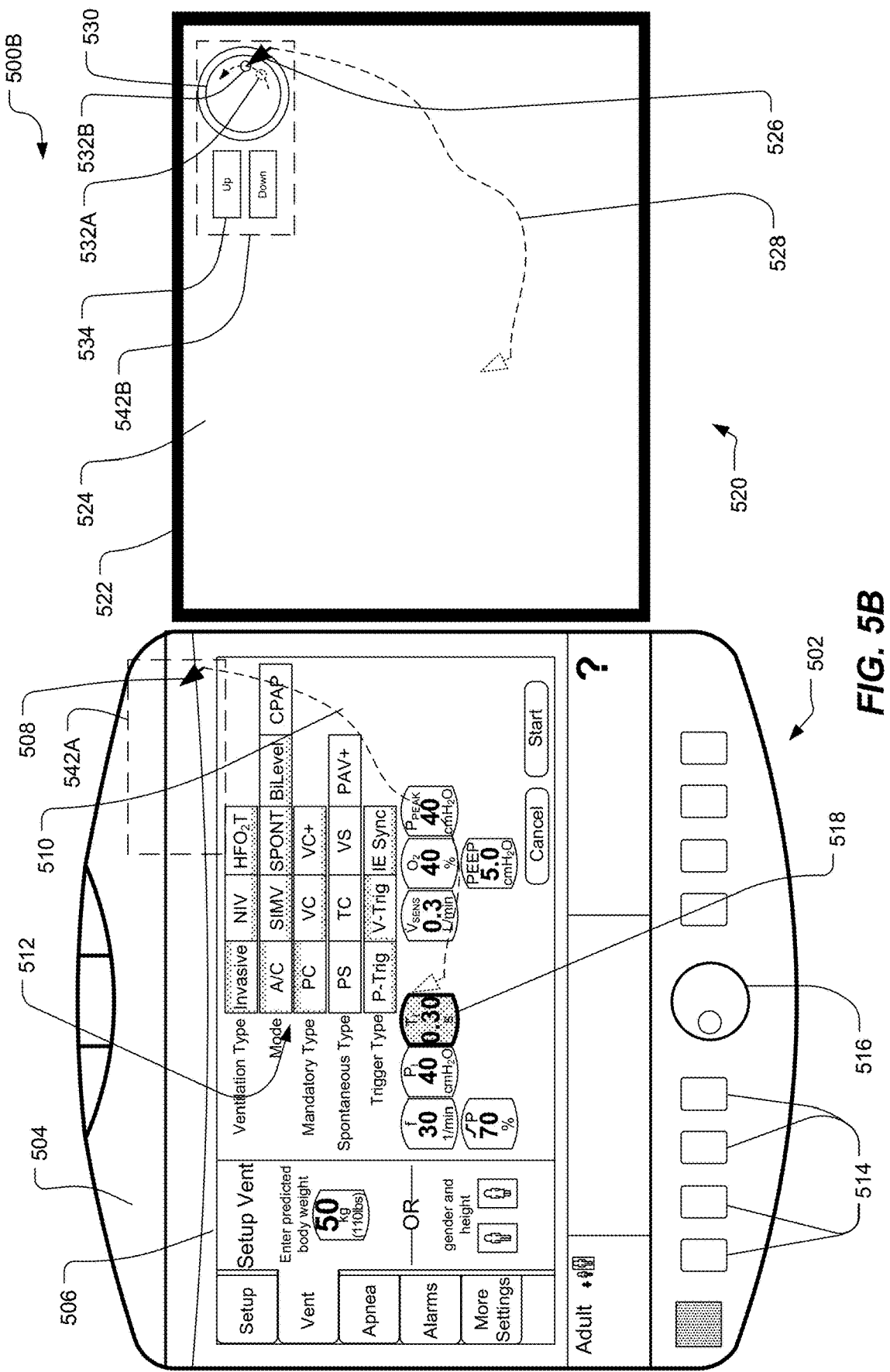

FIGS. 5A and 5B depict an example remote user interface 524 on a remote display 522 of a remote device 520, and a ventilator display 504 of a ventilator 502 showing a ventilator user interface 506. Aspects of FIGS. 5A and 5B show changing a value associated with a selected ventilator control element 518 of available ventilator control elements 512. Specifically, FIGS. 5A and 5B show a remote user interface 524 and ventilator user interface 506. The local ventilator position indicator 508 is associated with the remote position indicator 526, and may have associated past movement data 510, 528. In FIG. 5A, a particular ventilator setting (the control element 518) is selected, and in FIG. 5B it is adjusted.

For example, FIG. 5B shows the remote position indicator 526 rotating a virtual dial 530. The virtual dial 530 may be associated with a physical dial 516 on the ventilator (such as physical input component 129). Although a dial is used in this example, it should be appreciated that other virtual adjustment elements (such as soft key or button 534) may be displayed on the remote user interface 524 to be associated with a variety of physical input components (such as hard keys 514). In this way, a virtual input at the virtual dial 530 or soft key 534 may be associated with a physical input on a ventilator 502. An adjustment of the virtual dial 530 may be equivalent to an adjustment of the physical dial 516. The remote adjustment element 530, 534 may be overlaid or separate from the trackpad or elements of the remote user interface 524. In either example, the remote adjustment element 530, 534 may be positioned on the remote user interface 524 to not overlap with ventilator control elements 512 and/or disable selection of a ventilator control element 512 when receiving an adjustment input.

In this example, the adjustment input is a counterclockwise rotation (a negative angle of rotation) of the virtual dial 530 from a first position 532A to a second position 532B. The difference between the first position 532A and the second position 532B may be proportional to the change in the value associated with the selected ventilator control element 518. For example, the difference between the first position 532A and the second position 532B on virtual dial 530 may be an angle of rotation. The direction of rotation of the virtual dial 530 may represent a positive or negative change in the value. In this example, the selected ventilator control element 518 is adjusted from 0.40 s to 0.30 s, based on the angle of counterclockwise rotation between the first adjustment 532A and the second position 532B. As shown, the local ventilator position indicator 508 may have a past movement data 510 associated with the remote past movement data 528 on the remote user interface 524. In this case, the virtual dial 530 is positioned in an adjustment section 542B of the remote user interface 524 to correlate with a non-selectable region 542A of the ventilator user interface 506 to prevent unintended selection of a different ventilator control element 512 when receiving adjustment input. For example, when a remote position indicator 526 is positioned inside of the adjustment section 542B, the local ventilator position indicator 508 does not overlay with any ventilator control element 512. In this way, a selection of an adjustment element (e.g., the virtual dial 530) inside of the adjustment section 542B is not also associated with a selection of a ventilator control element 512.

In a further example, an adjustment caused by a mouse scroll or other input action at the remote device 520 may be visually indicated at the remote user interface 524. For instance, if a mouse scroll is received at the remote device 520 then a visual indication of a value adjustment may be shown on the remote user interface 524 (e.g., rotation of the virtual dial, varying color, varying brightness, otherwise emphasizing all or a portion of one or more bezel keys 536, a change in a displayed numerical value, etc.). Although examples describe rotation of a mouse wheel, it should be appreciated that any other input at the remote device 520 associated with a control at the ventilator (e.g., a local ventilator position indicator 508 is hovered-over the control or the control is selected) may result in an adjustment of the value associated with the control at the ventilator.

Figure 5C:
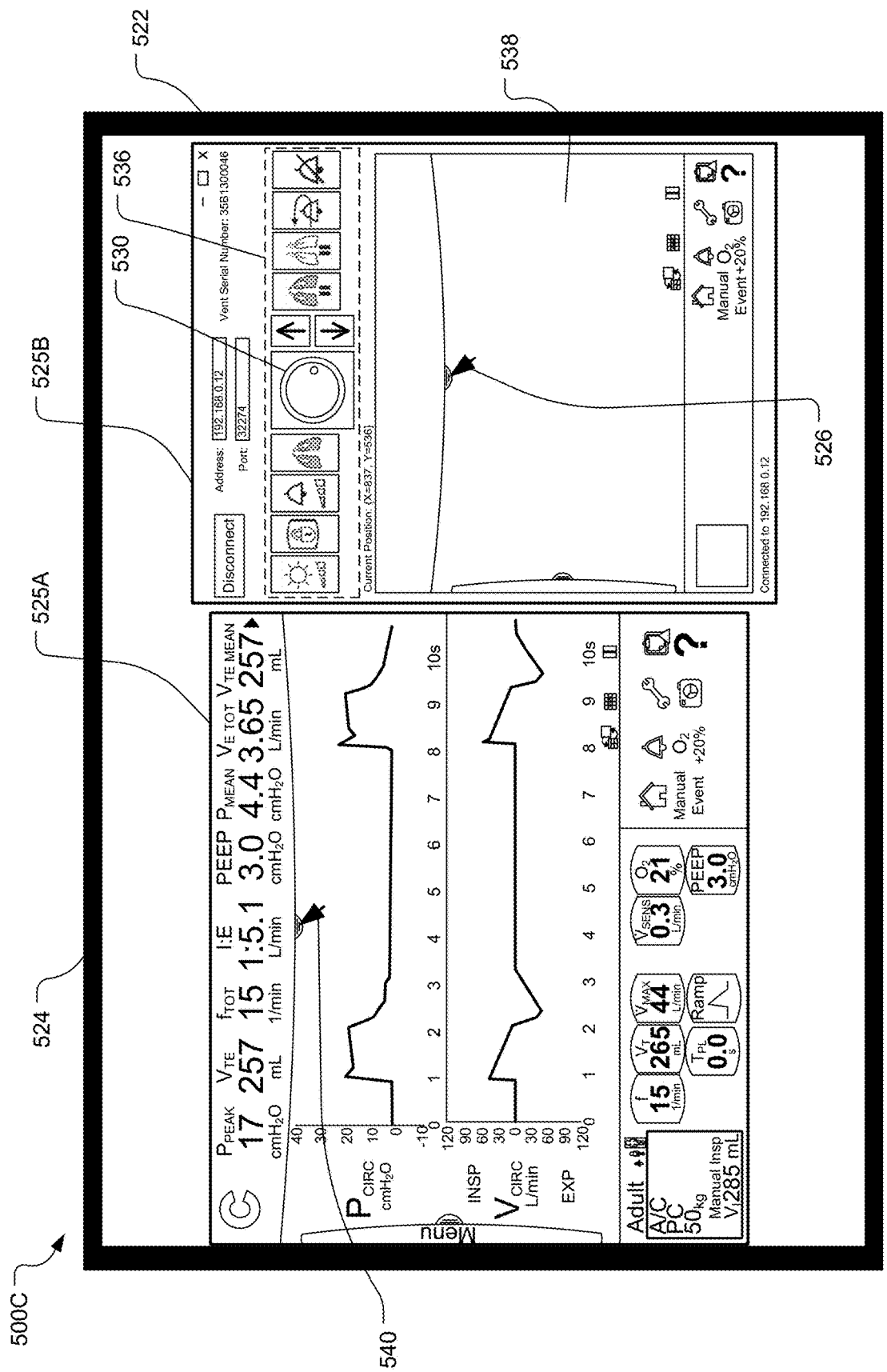
FIG. 5C depicts an example remote user interface on a remote display of a remote device.

FIG. 5C depicts an example remote user interface 524 on a remote display 522 of a remote device 520. As shown, the remote user interface 524 may include a first interface portion 525A and a second interface portion 525B. As shown, the first interface portion 525A and the second interface portion 525B are displayed in separate portions, segments, or windows of the remote user interface 524. The portions, segments, or windows may be resizeable and repositionable about the remote user interface 524. Additionally or alternatively, the remote user interface 524 may split display of the first interface portion 525A and the second interface portion 525B (e.g., in a split screen arrangement), and/or the first interface portion 525A and the second interface portion 525B may be overlaid. Other visual arrangements of the first interface portion 525A and the second interface portion 525B are also possible.

In an example, the first interface portion 525A may replicate a ventilator GUI (e.g., ventilator GUI 123) and user interface elements in the first interface portion 525A may not be selectable. The second interface portion 525B may include selectable and/or interactive user interface elements. For example, the second interface portion 525B may include features or elements similar to remote user interfaces (e.g., remote GUIs 163, 198, 230, 524) described herein. In this example, the second interface portion 525B may include a set of GUI control keys 536, a trackpad 538, and a remote position indicator 526. The set of GUI control keys 536 may include one or more control keys (or virtual bezel keys), such as a display brightness key, a display lock key, an alarm volume key, a manual inspiration key, an inspiratory pause key, an expiratory pause key, an alarm reset key, an audio paused key, etc. Each GUI control key in the set of GUI control keys 536 is associated with a control on the ventilator to which the remote device 520 is connected for remote control. In an example, the GUI control key may be associated with a ventilator GUI element. In another example, the GUI control key may be associated with a physical input at the ventilator. For example, a virtual dial 530 may be included in the set of GUI control keys 536 as associated with a physical input, as further described herein.

In an example, when a GUI control key in the set of GUI control keys 536 is selected at the remote user interface 524, the virtual dial 530 may then be selected and adjusted to adjust a value associated with the selected GUI control key at the ventilator. For example, a display brightness key may be selected. While the display brightness key is selected at the remote user interface 524, the virtual dial 530 may be adjusted and/or up/down adjustment keys may be selected to adjust or change the screen brightness value of the ventilator. In another example, an alarm volume key may be selected at the remote user interface 524 to adjust a volume value associated with the alarm at the ventilator. While the alarm volume key is selected, the volume value may be adjusted via interaction with the virtual dial 530 and/or up/down keys at the remote user interface 524.

In another example, a display lock key may be selected at the remote user interface 524 to prevent inadvertent settings changes to the ventilator (including the knob function) while the display is locked. In a further example, a manual inspiration key may be selected at the remote user interface 524. In examples, the manual inspiration key can be used to deliver mandatory breaths to the patient and/or to run an inspiratory pause maneuver in SPONT mode. In another example, selection of an inspiratory pause key at the remote user interface 524 may initiate an inspiratory pause maneuver at the ventilator. This may close the inspiratory and exhalation valves and extend the inspiratory phase of a mandatory breath for the purposes of measuring end inspiratory pressure for calculation of plateau pressure, static compliance, and static resistance. In a further example, selecting an expiratory pause key at the remote user interface 524 may initiate an expiratory pause maneuver at the ventilator, which may extend the expiratory phase of the current breath to measure total PEEP ($PEEP_{TOT}$). In another example, an alarm reset key may be selected at the remote user interface 524 to clear active alarms and/or reset high-priority alarms and/or cancel an active audio paused interval at the ventilator. In yet another example, selection of an audio paused key at the remote user interface 524 may pause alarms for a predetermined period of time at the ventilator.

In examples, the remote device 520 may replicate the ventilator GUI at the first interface portion 525A. The first interface portion 525A may include a replicate position indicator 540, replicating the local ventilator position indicator at the ventilator GUI. In this example, a clinician may interact with the trackpad 538 of the remote user interface 524 of the remote device 520 to control the ventilator without directly seeing the ventilator GUI. The clinician controlling the ventilator at the trackpad 538 may visually compare a remote position indicator 526 with the replicated display shown in the first interface portion 525A of the remote user interface 524 on the same remote device 520, without requiring a direct view of the ventilator GUI at the ventilator.

The remote user interface 524 may include additional information or controls associated with the remote device 520, connected ventilator, and/or data received or sent by the remote device 520. As shown, this additional information may be displayed at the second interface portion 525B. For example, the remote user interface 524 may include a disconnect key to disconnect for a ventilator and/or switch to control of a different ventilator. As another example, the remote user interface 524 may display additional, non-selectable information including a value associated with a currently selected GUI element and/or bezel key, a determine adjustment or change in the value, position information of a physical input at the ventilator, etc. For example, the remote user interface 524 may include a disconnect control to disconnect the remote device 520 from the ventilator and/or an intermediate device. In another example, the remote user interface 524 may include a serial number of the ventilator, X-Y coordinates of the remote position indicator 526 (e.g., X-Y coordinates at the remote user interface 524, X-Y coordinates at the ventilator GUI, and/or X-Y coordinates at an intermediate device GUI). Additionally or alternatively, the remote user interface 524 may include other system information (e.g., IP address, port, etc.).

Figure 6:
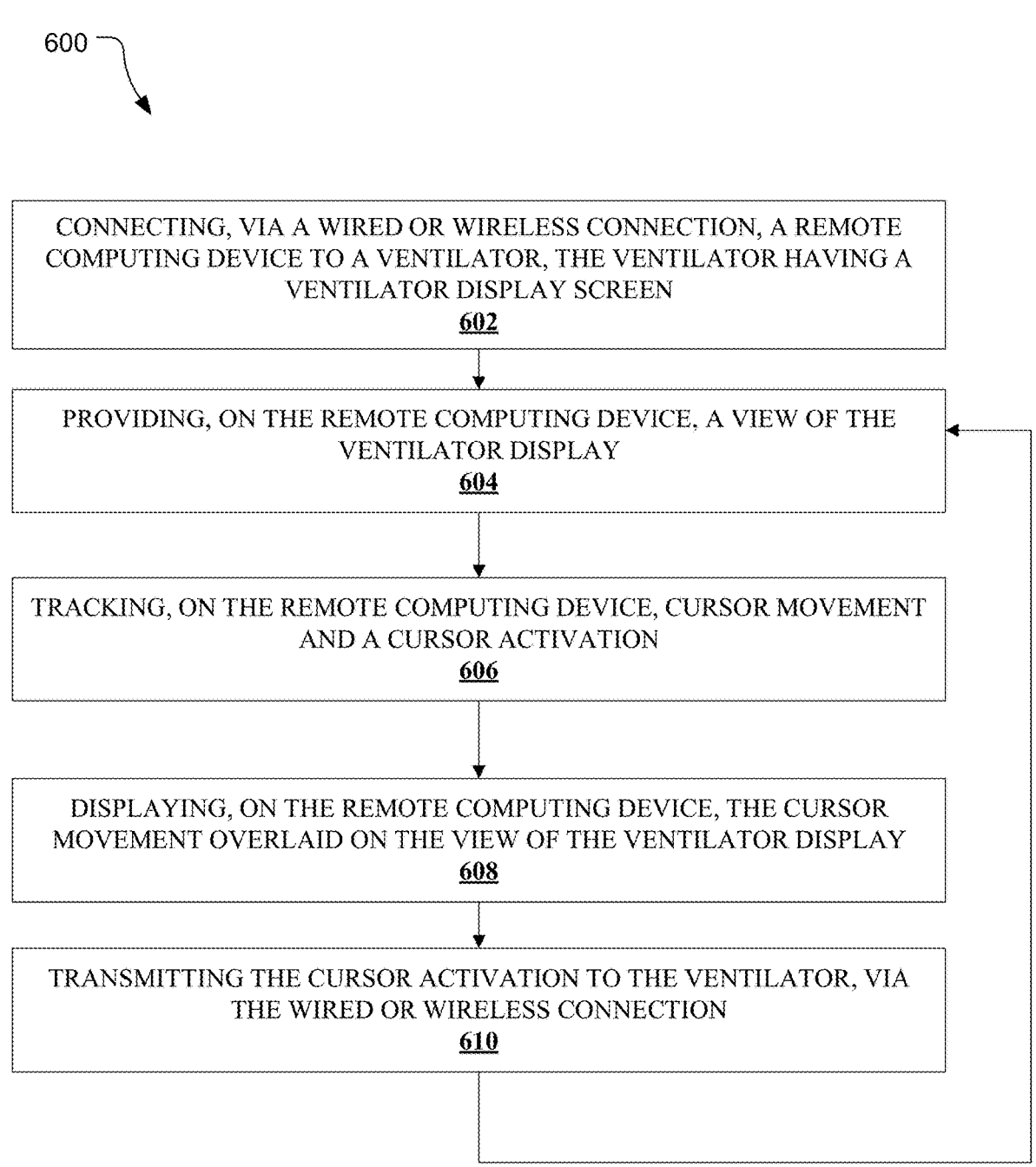
FIG. 6 depicts a method for remotely adjusting and/or accessing a ventilator based on an input received at a remote device.

FIG. 6 depicts a method 600 for remotely adjusting and/or accessing a ventilator (such as ventilators 100, 202, 502) based on an input received at a remote device (e.g., remote devices 160, 194, 226, 520). The operations of method 600 may be performed by the remote device and/or other components described in the above systems. At operation 602, a remote computing device may be connected to a ventilator, via a wired or wireless connection (e.g., wired or wireless connections 164, 192, 185, 214A, 214B, 214C), the ventilator having a ventilator display (e.g., ventilator displays 122, 204, 504). At operation 604, a view of the ventilator display may be provided on the remote computing device. For example, the view may be a replicate or copy of the ventilator display in a remote GUI (e.g., remote GUIs 163, 198, 230), such as described for the first interface portion 525A in remote user interface 524.

At operation 606, cursor movement and activations may be tracked on the remote computing device (e.g., via remote position indicator 165, 199, 232, 526). Cursor movement may be associated with a change in position of the cursor (e.g., as described for remote past movement data 234, 528). An activation may include a variety of interactions at the remote computing device, such as a selection (e.g., described herein at least with respect to selection input, selection information, and selection data) and/or an adjustment (e.g., described herein at least with respect to adjustment input, adjustment element, adjustment information, and adjustment data). The activation may include an interaction that is associated with an interaction at the ventilator.

At operation 608, the cursor movements may be overlaid on the view of the ventilator display and displayed on the remote computing device. In an example, the view of the ventilator display may be updated continually based on display information of the ventilator. In another example, operation 608 may be updated with operation 604, as the view of the ventilator display is provided. In another example, operation 608 may be based on a predetermined correlation of the view of the ventilator display with a cursor position at the remote computing device. Alternatively, cursor movements on the view of the ventilator display may be displayed without receiving information from the ventilator (e.g., the remote device may estimate the cursor position).

At operation 610, the cursor activation may be transmitted to the ventilator, via the wired or wireless connection. As described herein, the cursor activation at the remote device may be associated with a cursor activation at the ventilator at the position indicated on the view of the ventilator screen at the remote device. Thus, interactions at the remote device may control or adjust the ventilator over the wired or wireless connection.

One or more operations of method 600 may repeat. For example, operations 604-610 may repeat as the ventilator display changes or updates. For example, the ventilator display may change or update based on the cursor activations sent to the ventilator.

Figure 7A:
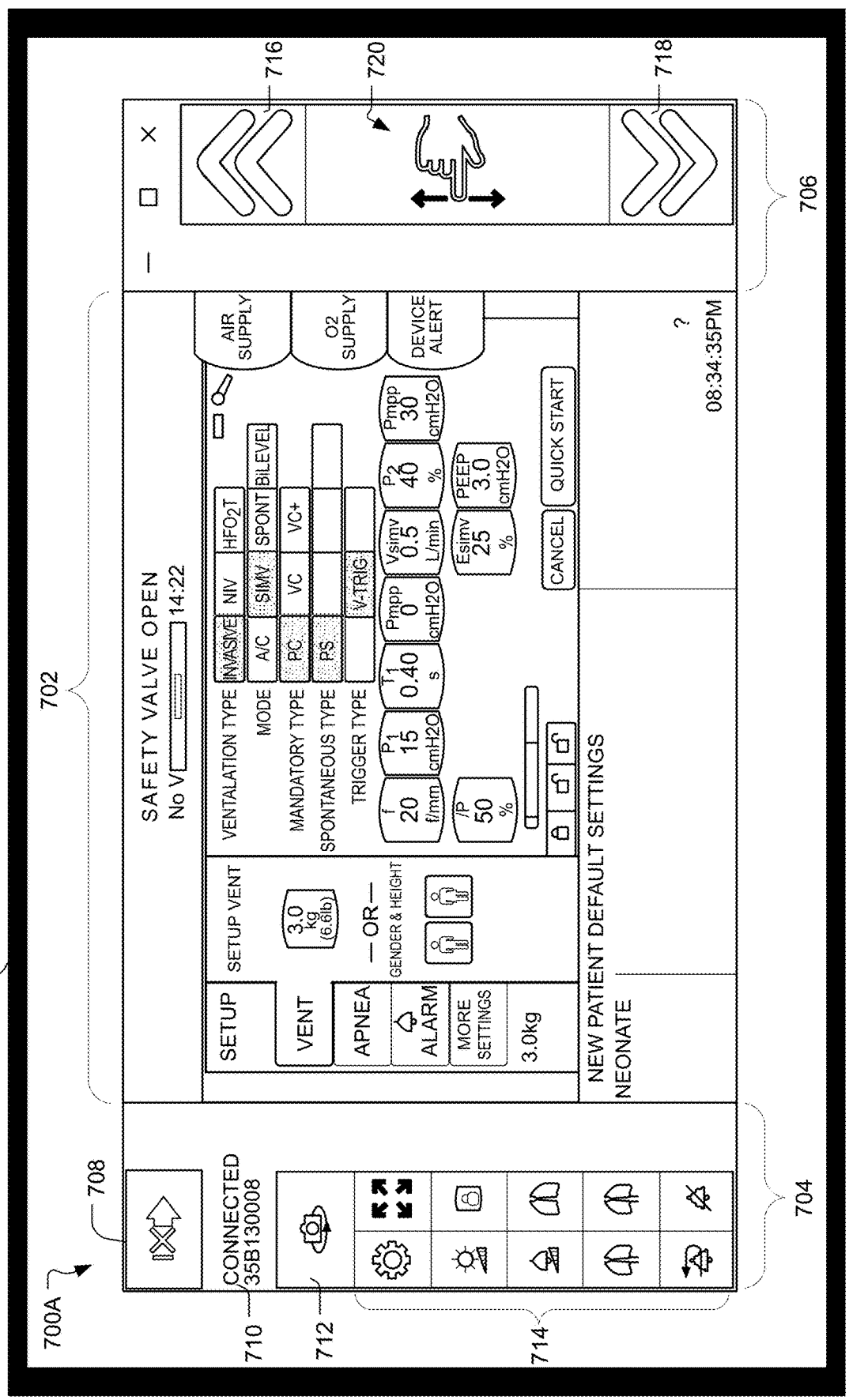
FIGS. 7A, 7B, 7C, and 7D depict examples of a remote user interface.
Figure 7B:
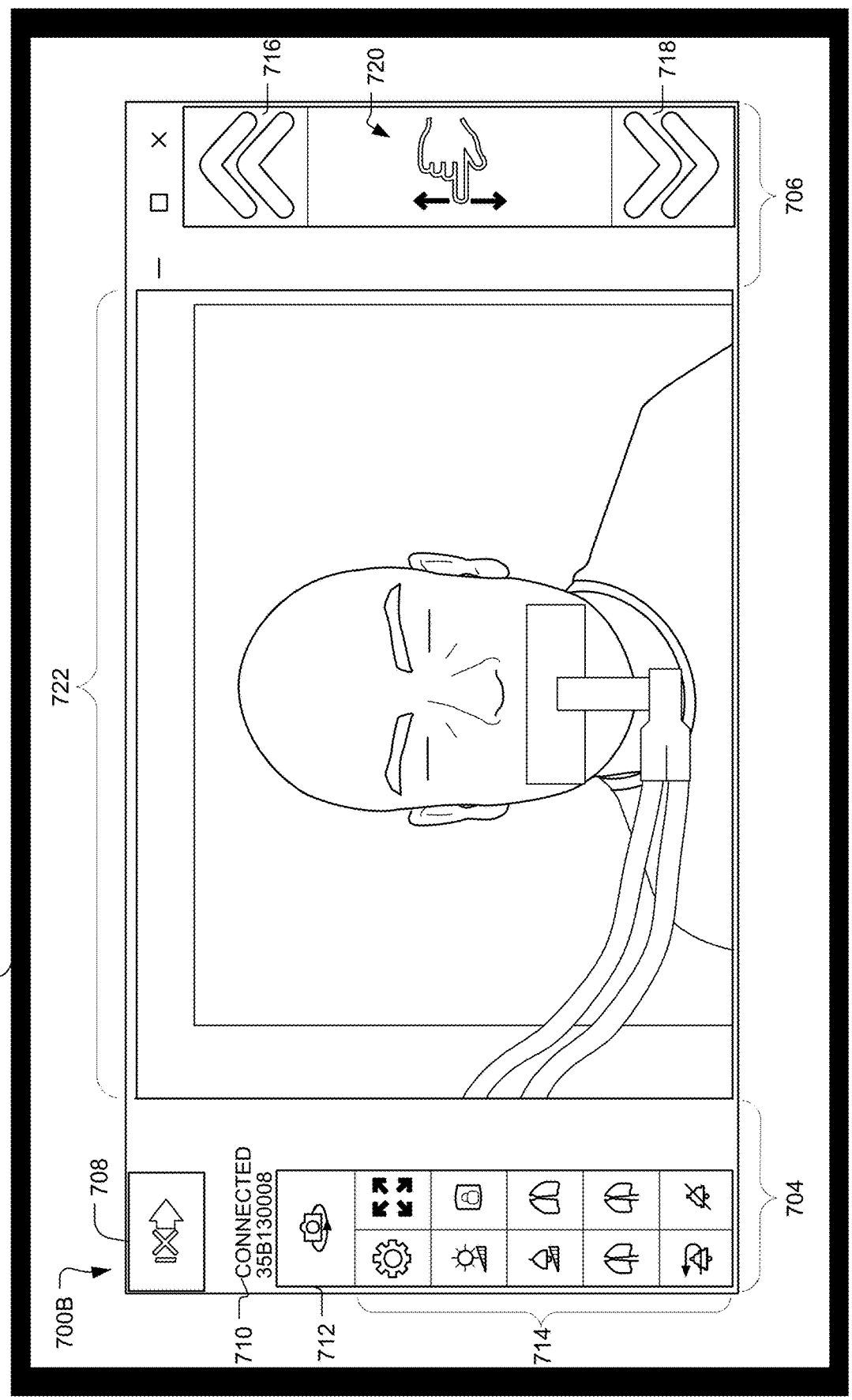
Figure 7C:
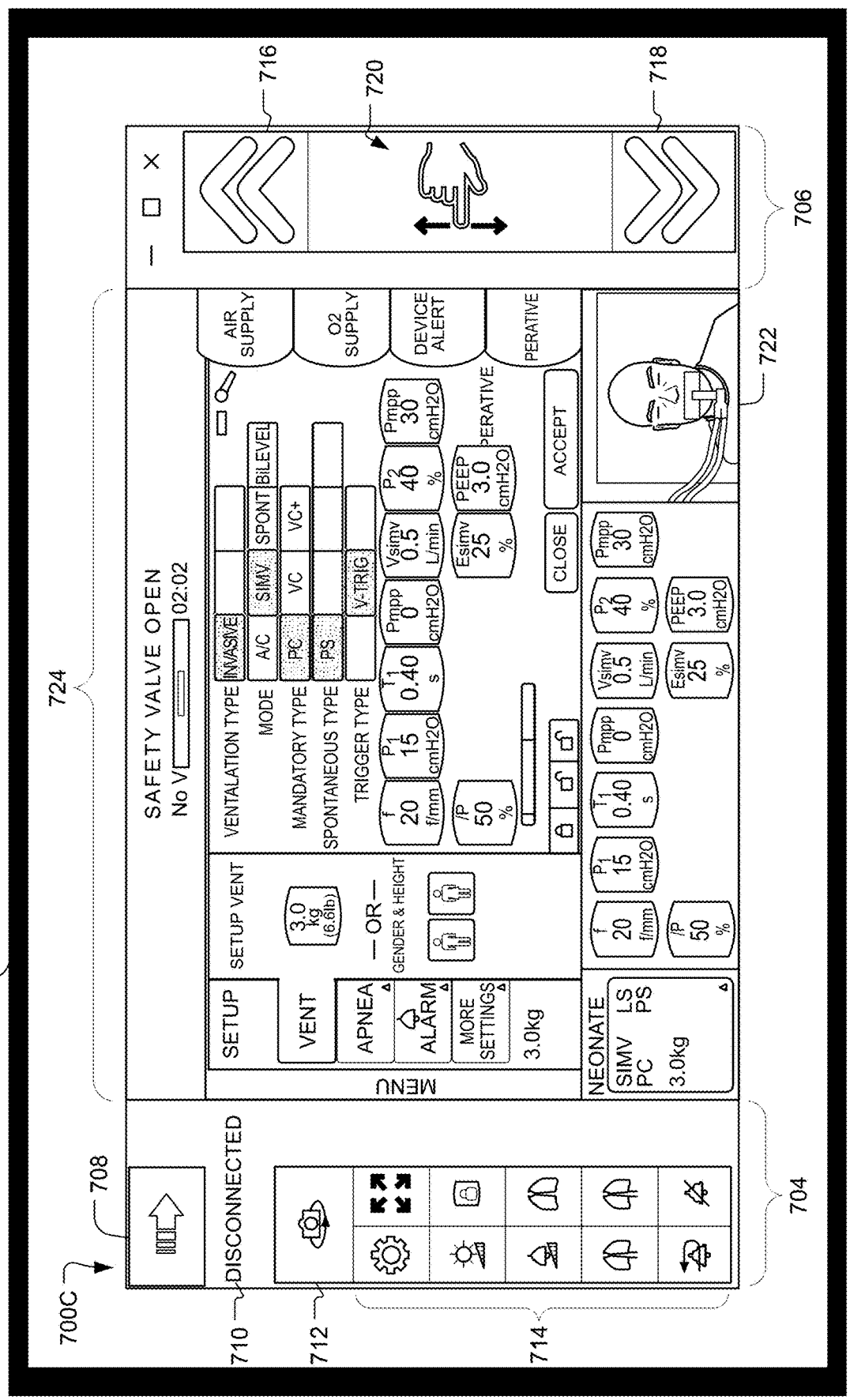
Figure 7D:
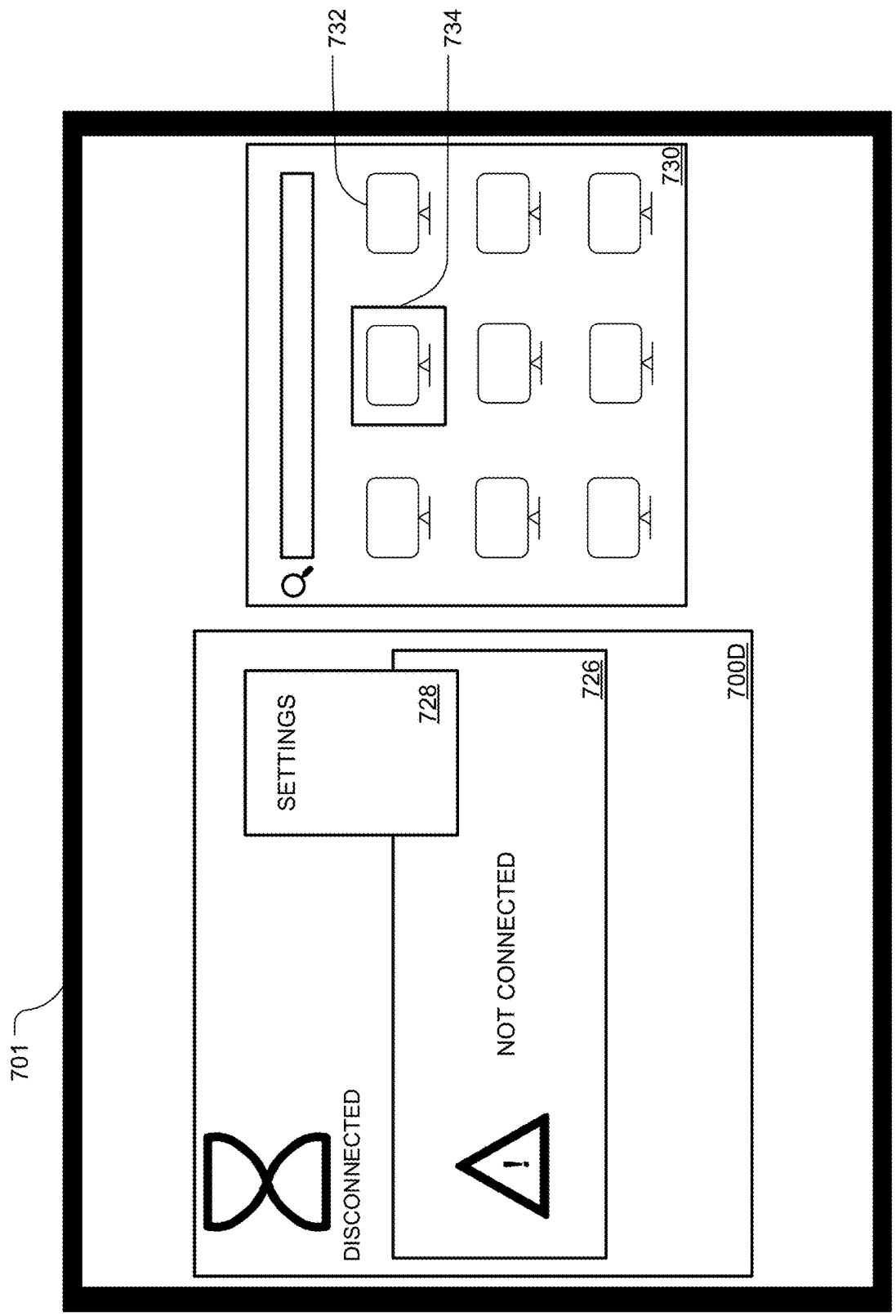

FIGS. 7A, 7B, 7C, and 7D depict example view modes of remote user interfaces 700A, 700B, 700C, 700D on a remote display 701 of a remote device. Specifically, FIGS. 7A, 7B, and 7C show different view modes of a remote user interface 700A, 700B, 700C in a window displayed on a remote device and FIG. 7D shows an example window with a setup view mode of a remote user interface 700D on a display 701 of a remote device. The view modes may be associated with an application running on the remote device in communication with a relay transceiver (e.g., relay transceivers described with respect to FIGS. 8A, 8B, and 9).

Regarding FIGS. 7A, 7B, and 7C, a remote user interface can operate in a ventilator view mode (FIG. 7A), in a patient view mode (FIG. 7B), and in a ventilator and patient inset view mode (FIG. 7C). These views are displayed on a display 701 of a remote device (e.g., a device located remote from the ventilator, such as outside of the room in which a ventilator is located). For example, a remote user interface 700A in a ventilator view mode shows a remote ventilator user interface (UI) 702 replicated from the ventilator GUI. The remote ventilator UI 702 may replicate an entire GUI displayed on a ventilator or may replicate a portion of the ventilator GUI. In some examples, at least 80 or 90 percent of the ventilator GUI (in terms of screen area) is replicated in the remote ventilator UI 702. The remote ventilator UI 702 includes at least one ventilator settings icon that is selectable at the remote ventilator UI 702 and/or the ventilator GUI. As shown in FIG. 7A, ventilator settings icons include respiratory rate (f), inhalation time, exhalation time, volume of synchronized intermittent mandatory ventilation (Vsimv), inhalation-to-exhalation (I:E) ratio, tidal volume, ventilation type, alarm settings, among other settings shown or not shown in FIG. 7A that are selectable on a GUI of a ventilator.

The remote ventilator UI 702 may be rearranged and/or reformatted based on the size of a display 701 of the remote device or a size of the window or panel displaying the remote ventilator UI 702. For example, at least one ventilator settings icon may be rearranged or reformatted (e.g., enlarged). The portion of the ventilator GUI displayed at the remote device may be a cropped portion of the ventilator GUI or one or more ventilator settings icons (including a subset of the ventilator settings icons displayed on the ventilator GUI). In an example, a subset of ventilator settings icons displayed at the remote ventilator UI 702 may change over time, such as being scrolled manually or automatically, or replaced at a time interval. One or more ventilator settings icons may be resized (e.g., enlarge, shrink, change an aspect ratio, change a shape, etc.) compared to other replicated aspects of the ventilator GUI. As an example, ventilator settings icons that are most frequently changed may be enlarged as compared to other ventilator settings icons. In some examples, the least frequently changed settings may be omitted from the remote ventilator GUI 702 or included at the end of a scrollable interface. A format or arrangement of the remote ventilator UI 702 may be based on threshold of the display size. For example, a first format or first arrangement may be displayed if a display size is less than a threshold and a second format or second arrangement may be displayed if the display size is greater than or equal to the threshold.

A patient view mode of a remote user interface 700B shows a patient video feed 722 (or a patient image 722) obtained via a video or camera input (e.g., as received as input into a relay transceiver or the ventilator). A ventilator and patient inset view mode of a remote user interface 700C shows a patient inset remote ventilator UI 724 including a small version of the patient video feed 722.

All three of the example view modes shown on the remote user interface 700A, 700B, 700C (e.g., the ventilator view mode, the patient view mode, and the ventilator and patient inset view mode) may include additional sections, such as a selection section (represented by panel 704) and an adjustment section (represented by panel 706), that may remain unchanged regardless of the view mode. These panels 704, 706 are used to display information or graphical elements that remain available in all view modes.

The panels 704, 706 may be located on any region or section in the remote user interface 700A, 700B, 700C, which may be separate or combined. For example, as shown in FIGS. 7A, 7B, and 7C, the panel 704 is positioned on a left panel of the remote user interface 700A, 700B, 700C and the panel 706 is positioned on a right panel of the remote user interface 700A, 700B, 700C. Panel sizes, positions, formats, or arrangements may be based on a size of the display 701 and/or a size of the window displaying the remote user interface 700A, 700B, 700C, 700D. Panels may be expandable or capable of being minimized and enlarged or expanded.

In an embodiment, the panel 704 is an icon panel that includes a variety of selectable icons not displayed on a ventilator GUI of the actual ventilator itself. For example, the icon panel 704 may include a connect or disconnect button 708 that is selectable (e.g., via touch on a touchscreen display or via a mouse click on a mouse-controlled display). When the remote device is connected to a ventilator, selection of the disconnect button 708 may cause the remote device to disconnect from the ventilator or relay transceiver. When the remote device is not connected to a ventilator or relay transceiver, the connect button 708 may be selected to connect to a ventilator or launch a connection routine to connect to a ventilator or relay transceiver. The connect or disconnect button 708 may indicate if a connection between the remote device and a relay transceiver is stable. For instance, the display of the connect or disconnect button 708 may change based on the connection status.

Information 710 may be displayed in the icon panel 704, or in any other area of the view, to provide status information (e.g., information that indicates whether the remote device is connected to a ventilator or relay transceiver, the remote device is disconnected from a ventilator or relay transceiver, the remote device is connected with view-only access, with view and control access, etc.). Additionally, the information 710 displayed may include ventilator identification information, relay transceiver identification information, patent identification information, and/or remote device identification information. Ventilator identification information may include a ventilator serial number, a room number or site identifier of the ventilator, a name of the ventilator, an IP address of a ventilator, a user to which the ventilator is assigned (e.g., doctor, clinician, medical team, etc.), or any other information specific to a ventilator that is being remotely accessed. Relay transceiver identification information may include a relay transceiver serial number, a room number or site identifier of the relay transceiver, a name of the relay transceiver, an IP address of the relay transceiver, a user to which the relay transceiver is assigned (e.g., doctor, clinician, medical team, etc.), or any other information specific to a relay transceiver for providing remote access to a ventilator by a remote device. Patent identification information may include a patient identifier (e.g., name, initials, bodyweight, gender, etc.), a patient room number or site identifier, a patent infectious code, an anonymized patient identifier, etc. Remote device identification information may include a device serial number, a name of the device, an IP address of the device, a user to which the device is assigned (e.g., doctor, clinician, medical team, etc.), or any other information specific to a remote device remotely accessing a ventilator, or any other remote devices concurrently remotely accessing the ventilator (e.g., via a relay transceiver).

In an embodiment, the icon panel 704 also includes a view selector 712, which allows a user to switch to a different view mode. For example, a selection of the view selector 712 may cause a sequential change in view between the remote user interface 700A in a ventilator view mode, a remote user interface 700B in a patient view mode 700B, and a remote user interface 700C in a ventilator and patient inset view mode. If only two view modes are available, then a selection of the view selector 712 may toggle between the two view modes. Additionally or alternatively, the view selector 712 may allow a user to select which view to show (e.g., via a dropdown menu or other selection menu). The view selector 712 may also allow for camera control where a camera is available. For instance, a camera may be connected to the ventilator and/or the relay transceiver to allow for a view of the patient. The view selector 712 may control the direction of the camera or other camera properties. Selection of the view selector 712 may provide options for rotating the camera and or changing other camera properties (e.g., zoom).

The icon panel 704 may also include one or more virtual bezel keys 714. that correspond with physical bezel keys on the ventilator. Selection of the virtual bezel keys 714 at the remote device represents a physical selection of a bezel key at the ventilator. Descriptions of physical bezel keys and bezel key user interface elements are further discussed with respect to FIG. 5C. The virtual bezel keys 714 may be displayed in any configuration, such as a compact rectangular tile configuration shown in FIGS. 7A, 7B, and 7C.

In an embodiment, the panel 706 is an interactive panel used to accept adjustments of the selected ventilator setting icon (e.g., a selected virtual bezel key 714 or a selected icon). The adjustment section (represented by panel 706) may include one or more adjustment elements (e.g., up icon, down icon, slide bar, rotatable dial, etc.). In FIG. 7A, the panel 706 includes a slide bar 720 with up and down slide icons 716, 718. The slide bar 720 or icons 716, 718 are used to change the selected ventilator setting. For instance, a single selection of the up icon 716 or the down icon 718 may cause a single, stepwise adjustment of the selected ventilator setting in either the upward or downward direction, respectively. Multiple selections of the up icon 716 or the down icon 718 may cause multiple, stepwise adjustments of the selected ventilator setting in either the upward or downward direction, respectively.

The slide bar 720 may adjust a selected ventilator setting based on a select, drag, and drop interaction with the slide bar 720. For example, dragging up on the slide bar 720 may adjust a selected setting upwards and dragging down may adjust a selected setting downwards. This drag action may be performed using a touch interaction or a mouse interaction. The slide bar 720 may vary in incremental adjustments based on an acceleration of a user's drag motion. For example, a setting may be adjusted more quickly (e.g., in larger step increments) for a drag with faster acceleration than a drag with slower acceleration. Alternatively, the slide bar 720 may adjust a setting linearly (e.g., in standardized increments based on distance of a drag motion), regardless of drag acceleration. The slide bar 720 may be a replacement for the functionality described for the virtual dial 530 described in FIGS. 5A, 5B, and 5C. Alternatively, the panel 760 may display the virtual dial 530 instead of or in addition to the slide bar 720. Other types of interactive adjustment UI elements for increasing or decreasing settings may also be utilized.

FIG. 7D shows a display 701 of a remote device in a system view mode of a remote user interface 700D. This view mode includes a settings window 728 (with user settings, access permissions, default views, and preferences) and a selection window 730 showing available relay transceivers and/or ventilators represented by icons 732. The setup view mode of the remote user interface 700D may be displayed when the remote device is not connected to ventilator and/or relay transceiver. For instance, when a clinician or other user first picks up the remote device to interact with a ventilator, the setup view mode of the remote user interface 700D may be displayed to allow for setup and connection to a ventilator. The setup view mode of the remote user interface 700D may also be displayed when a user intends to connect to a different ventilator and/or relay transceiver.

For instance, each icon 732 may correspond to a different ventilator and/or relay transceiver that is available to be controlled or viewed remotely. Each of the icons 732 may be labelled or named with an identifier such as the ventilator identification information, relay transceiver identification information, or patent identification information. A selection indicator (such as box 734) indicates which icon is currently selected.

Additionally or alternatively, a warning message 726 may be displayed prior to allowing selection of a ventilator (via icon 734) for remote access. The warning message 726 may require user action, such as a usage agreement or confirmation.

Figure 8A:
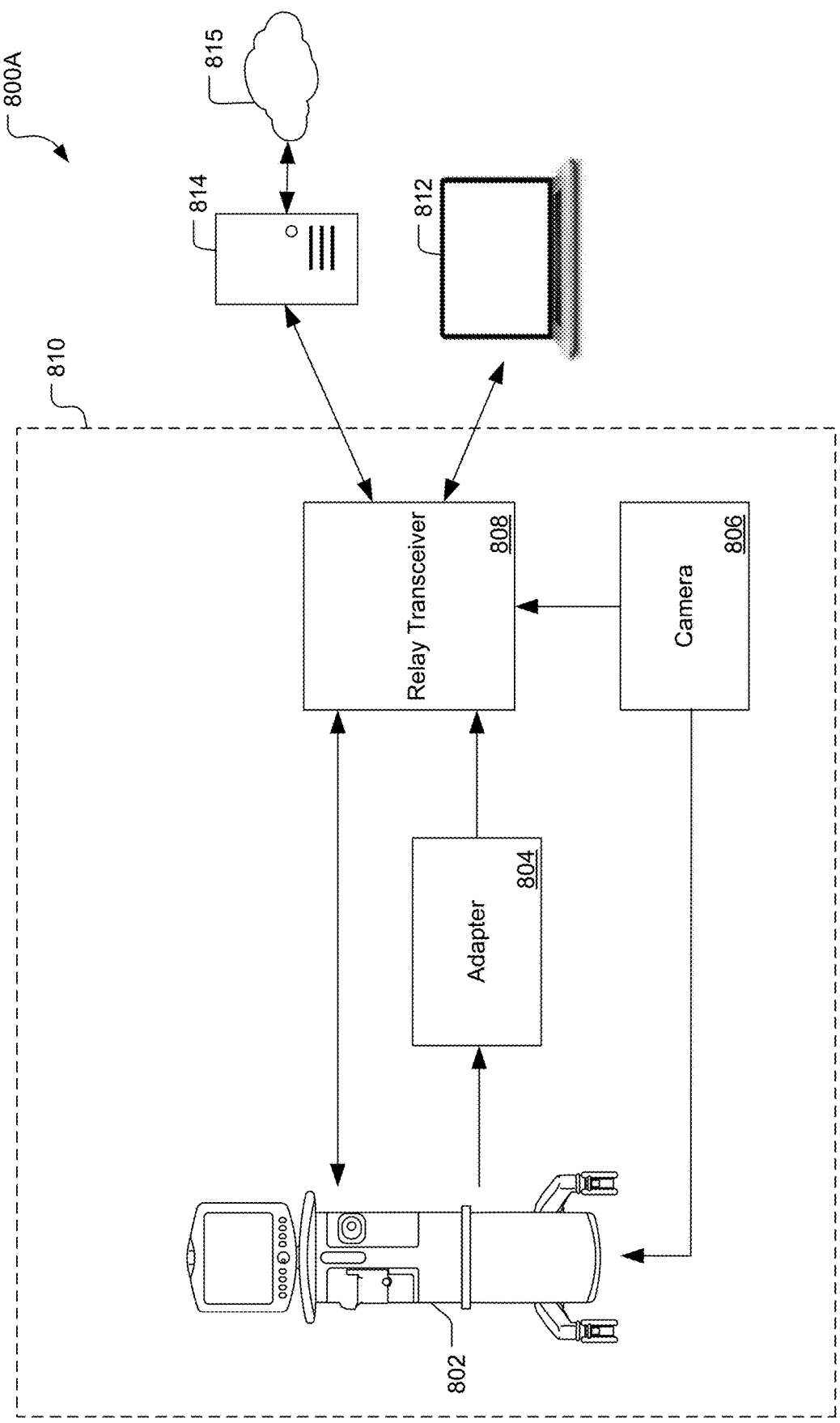
FIGS. 8A and 8B depict example systems for remotely adjusting a ventilator with a remote device.
Figure 8B:
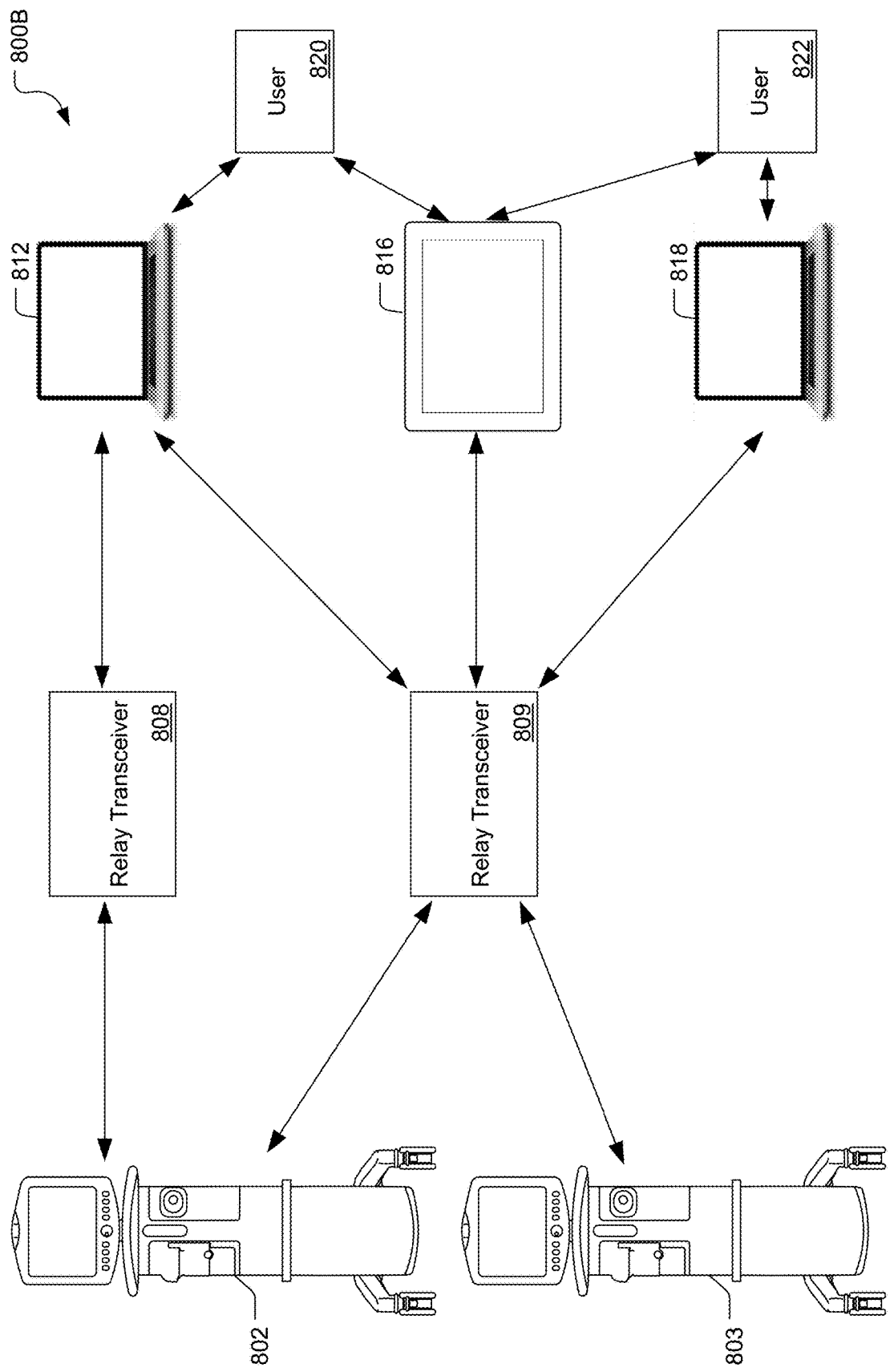

FIGS. 8A and 8B depict example systems for remotely adjusting a ventilator with a remote device. Specifically, FIG. 8A shows an example system 800A with one ventilator 802 paired with one relay transceiver 808, accessed by multiple remote devices (e.g., laptop 812 and remote server 814 or other remote devices such as a tablet, smartphone, laptop computer, desktop computer, or others) to allow for remote-control of the ventilator 802. FIG. 8B shows an example system 800B with a variety of connections between ventilators, relay transceivers, remote devices, and users.

Referring to FIG. 8A, a ventilator 802 may be paired with a relay transceiver 808 in a one-to-one relationship. The relay transceiver 808 allows for connectivity of one or more remote devices 812, 814 with the ventilator 802. The relay transceiver 808 may be attachable to, or removable from, the ventilator 802. For example, the relay transceiver 808 may plug into a data port (such as an HDMI or USB port) of the ventilator 802 (directly or through an adapter 804), or may communicate with the ventilator wirelessly (directly or through an adapter 804).

The relay transceiver 808 is hardware, and can take the form of a laptop, a miniature computer, processing box (such as a headless computer), a dongle, a smart cable, or other small portable processor. One example relay transceiver 808 may include a NUC PC available from the Intel Corporation. In an embodiment, the relay transceiver 808 is external to the ventilator 802 and is portable such that a clinician may easily move the relay transceiver 808 to different rooms or different ventilators. In some examples, the relay transceiver 808 may have a volume of less than 500 cubic centimeters. Alternatively, the relay transceiver 808 may be embedded, internal, and/or integrated into a ventilator 802.

In an embodiment, the relay transceiver provides the connectivity hardware and software needed for the remote devices 812 and 814, such that no changes (e.g., hardware or software changes) need to be made to the ventilator 802 itself. Thus, the relay transceiver 808 adds remote connectivity functionality to a standalone or offline ventilator 802.

As shown in FIG. 8A, a camera 806 may be paired with a relay transceiver 808 and/or a ventilator 802 to allow a patient video or image to be captured for display on a remote device (e.g., laptop 812 or server 814). The camera 806 may be a webcam, standalone camera, portable camera, USB camera, or other device with video or camera capability. Audio may also be captured and transmitted by the camera 806. Thus, a clinician using a remote device may be able to see and hear the patient.

In some examples, another camera may be integrated into one or more of the remote devices, such as a selfie or front-facing camera on a tablet. The camera may be used to capture video of the clinician, to enable two-way video and/or audio communication between the clinician and the patient, transmitted via the relay transceiver 808.

The relay transceiver 808 allows for access (e.g., view and/or control) to a ventilator 802 to be unbounded by geography or distance. In some examples, remote devices in any location may be given access permissions to connect to a ventilator 802 via the relay transceiver 808. Access may be limited by security credentials and authentication protocols based on a facility's security policies and network configurations. For example, the relay transceiver 808 may implement a lockout feature to prevent setting changes from two or more remote device from occurring simultaneously (e.g., changes are received in sequence or changes may be limited to a quantity of devices allowed to access a relay transceiver in a control mode).

The security policies and access controls may be based on, or managed by, the hospital or medical facility in which the ventilators 802 /or relay transceiver 808 are housed. For example, clinicians within, or associated with, the medical facility may be required to log in to the remote devices 812, 814. Logging in to the remote device 812 then provides access to the relay transceiver 808 connected to a particular ventilator 802. For example, once logged into the remote device, the clinician may be able to access the setup view mode of the remote user interface 700D and/or the other remote-control interfaces shown in FIGS. 7A-7D.

The remote server 814 may provide a connection to the Internet 815 to allow for cloud storage or access to the ventilator. Notably, the relay transceiver is not a secondary head or a second UI of the ventilator 802; instead, the relay transceiver 808 provides a path to a laptop, tablet, or other remote device for user interaction.

FIG. 8B shows an example system 800B having a variety of configurations of ventilators (e.g., ventilator 802 and ventilator 803), relay transceivers 808 and 809, remote devices (e.g., laptop 812, tablet 816, laptop 818), and remote users (e.g., user 820 and user 822). As shown, ventilator 802 can be paired with two relay transceivers 808, 809, which each communicate with a subset of the remote devices 812, 816, and 818. The ventilator 803 is paired with a single relay transceiver 809. This figure shows that a single ventilator may be paired with one or more relay transceivers, multiple ventilators may be paired with a single relay transceiver, and multiple ventilators may be paired with multiple relay transceivers.

As also shown in FIG. 8B, the relay transceivers 808, 809 may be configured in a variety of device relationships. Rather than accessibility being limited to one remote device 812, the relay transceivers can authorize or enable connection to multiple remote devices 812, 816, 818. For example, a one-to-many configuration may be permitted for remote devices accessing the ventilator with view-only permissions, while limiting to a one-to-one configuration for remote devices with control or adjustment permissions.

FIG. 8B also depicts a variety of configurations for remote devices and users. For example, a singe remote device (e.g., laptop 812) may be used by a single user (e.g., user 820) in a one-to-one relationship of device-to-user. Additionally, multiple remote devices (e.g., laptop 812 and tablet 816) may be accessed by a single user (e.g., user 820) in a many-to-one relationship. In another configuration, a single remote device (e.g., tablet 816) may be accessed by multiple users (e.g., user 820 and user 822) in a one-to-many relationship. For example, multiple clinicians may share a remote device, such as a tablet assigned to a specific hospital area (wing, ICU, etc.) and/or specific ventilator. The tablet may be passed among users of a medical team, or passed to a different user from shift-to-shift, etc. Further, multiple remote devices may be accessible by multiple users.

The relay transceiver may also store and/or generate usage logs and usage statistics. For example, when a relay transceiver is accessed by a remote device, a remote device identifier (e.g., serial number, IP address, account, etc.) is logged and timestamped in association with a ventilator identifier (e.g., serial number, IP address, name, room number, etc.) of the ventilator(s) being accessed via the relay transceiver. The usage log may also record and store information relating to how many times a remote device accessed the relay transceiver, which virtual bezel keys were selected, which locations in the window were selected (e.g., via touch or mouse-click), etc. Statistics and/or reports may be generated based on a usage log for analysis. For example, statistics and/or reports may provide insight for care givers (e.g., frequency and instances of remote care, use of remote devices, last user to log in, etc.), diagnostics, feature development, security (e.g., cybersecurity considerations), or for any other reason.

Figure 9:
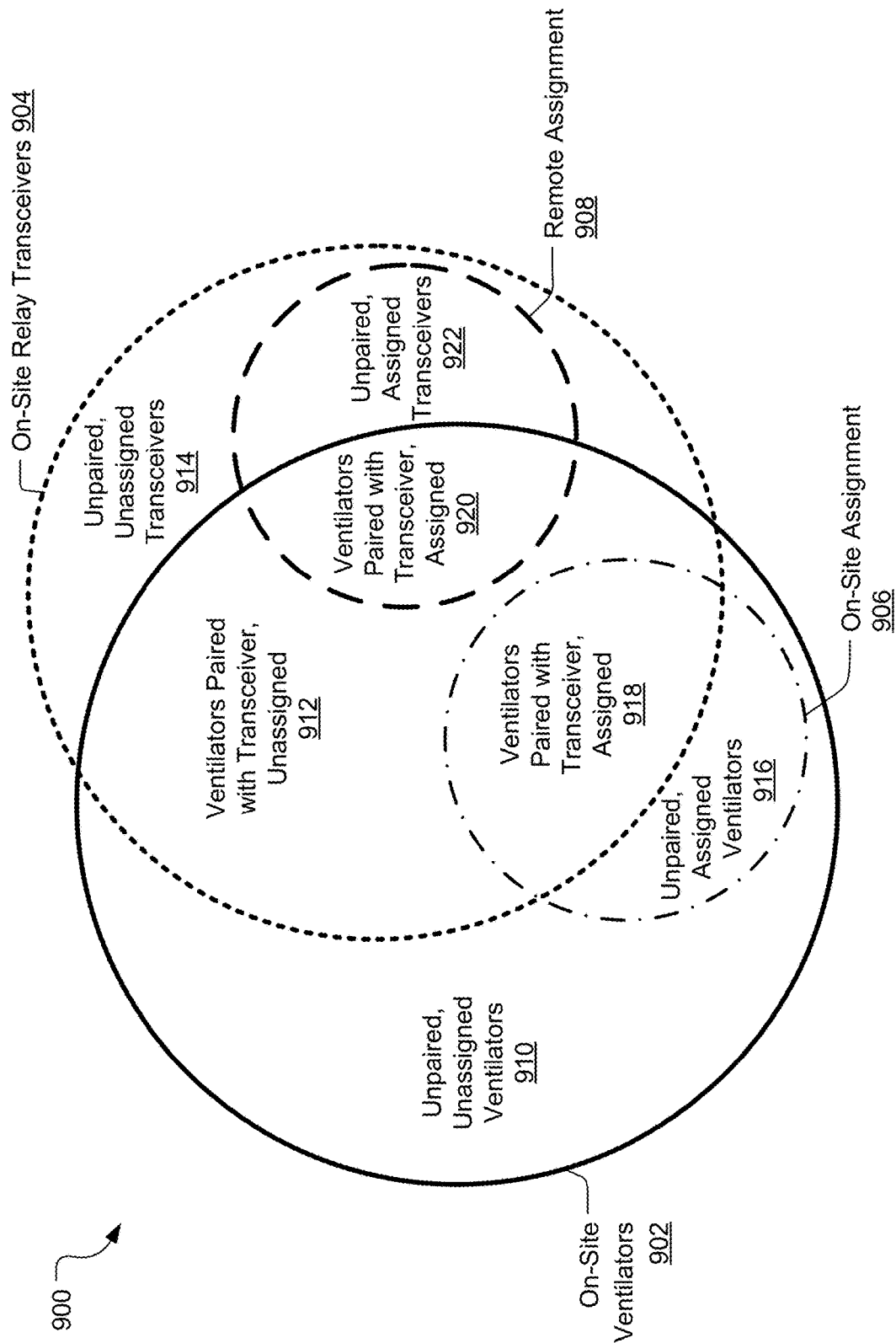
FIG. 9 depicts a diagram showing example allocations of relay transceivers.

FIG. 9 depicts a diagram 900 showing example allocations of relay transceivers (such as relay transceivers 808, 809). As further described herein, relay transceivers may be flexibly paired with ventilators in a care facility (e.g., hospital). The diagram 900 depicted in FIG. 9 shows example relationships between on-site ventilators 902 (e.g., a fleet of ventilators available, maintained, or in use at a care facility or hospital); on-site relay transceivers 904 (e.g., relay transceivers located at the same care facility or hospital as the on-site ventilators 902); on-site assignment 906 (e.g., assignment of an on-site ventilator 902 or on-site relay transceiver 904 to a user located at the same care facility or hospital as the on-site ventilators 902); and remote assignment 908 (e.g., assignment of an on-site relay transceiver 904 to a remote or off-site consultant, transferring patient, etc.). As otherwise used herein, a user may refer to an individual (e.g., a doctor, clinician, etc.) or a team of associated individuals (e.g., multiple users or a team of users, such as a doctor and the doctor's supporting staff/ team). Each region of the diagram 900 shown in FIG. 9 represents a different allocation of resources (e.g., on-site ventilators 902 and/or on-site relay transceivers 904).

As shown, the quantity of on-site ventilators 902 and the quantity of on-site relay transceivers 904 may be different. For example, there may be less on-site relay transceivers 904 than on-site ventilators 902 (e.g., the on-site relay transceivers may be paired with some ventilators on a need-basis), or there may be more on-site relay transceivers 904 than on-site ventilators 902 (e.g., to allow remote access capability to at least every ventilator). Alternatively, the quantity of on-site ventilators 902 and the quantity of on-site relay transceivers 904 may be the same.

Region 910 represents on-site ventilators 902 that are not paired with an on-site relay transceiver 904 and are not assigned (e.g., to a user, function, location, etc.). This region 910 includes on-site ventilators 902 for general use that may not benefit from pairing with an on-site relay transceiver 904. For example, region 910 may include a ventilator supporting a patient that does not have an infectious disease and/or is not immunocompromised, ventilators supporting a patient that is in a fragile state that would benefit from in-person interactions such as neonatal patients, or ventilators that are not in use or reserved.

Region 912 represents on-site ventilators 902 that are paired with relay transceivers 904 and are not assigned. This region 912 may include on-site relay transceivers 904 paired with specific on-site ventilators 902. On-site relay transceivers 904 that are paired with specific on-site ventilators 902 may be used to manage a ventilator fleet, such as providing a remote view of an entire fleet of ventilators, determining which ventilators in a specific fleet are currently running, a status or stage of ventilator associated with each of the ventilators (e.g., how many ventilators are using high-flow oxygen therapy or other ventilator modes, how many are weaning and may soon be available, how many are being serviced/require diagnostics, etc.).

Region 914 represents on-site relay transceivers 904 that are not paired with an on-site ventilator 902 and are unassigned. This region 914 includes on-site relay transceivers 904 that are available for pairing with a ventilator and not otherwise reserved.

Referring to assignment of on-site ventilators 902 and on-site relay transceivers 904, ventilators and/or relay transceivers may be assigned to a specific user (e.g., user or team of users), for a specific function (e.g., for infectious patients, terminal patients, neonatal patients, etc.), or to a specific location (e.g., maternity ward, floor of a hospital, pediatric ward, etc.). Regions 916, 918, 920, and 922 discuss how an assignment may impact allocation of resources. The diagram 900 shown in FIG. 9 shows assignments classified in two ways: on-site assignment 906 (e.g., assignment to a user, team of users, ventilator, patient, function, room, ward, site, etc. internal to the care facility or hospital in which the on-site ventilators 902 are located), and remote assignment 908 (e.g., assignment to a user, team of users, patient, function, remote consult, etc. external to the care facility or hospital in which the on-site ventilators 902 are located). Assignment of resources (e.g., ventilators and/or relay transceivers) may be permanent, semi-permanent, or temporary.

Region 916 represents on-site ventilators 902 that are not paired with an on-site relay transceiver 904 and are assigned. The ventilators in this region 916 may be reserved for use associated with their specific assignment and may be pairable with an on-site relay transceiver that is not yet paired (e.g., regions 914, 922) or pairable with an on-site relay transceiver 904 that is already paired (e.g., regions 912, 918, 920, if the ventilator is pairable with multiple relay transceivers). For example, a set of ventilators may be assigned to a COVID-19 recovery ward where patients may no longer be infectious (e.g., use of an on-site relay transceiver may be more beneficial paired to other ventilators).

Region 922 represents on-site relay transceivers 904 that are not paired with an on-site ventilator 902 and are assigned. The on-site relay transceivers in this region 922 may be reserved for use associated with their specific assignment. For example, an on-site relay transceiver may be assigned to a remote consultant (e.g., diagnostics team, remote doctor, educational team, etc.) for which a consult is not yet needed (e.g., the relay transceiver is available for a time when a consult is required or desired).

Region 918 represents on-site ventilators 902 that are paired with an on-site relay transceiver 904 and have an on-site assignment 906. The ventilators and/or relay transceivers in this region 916 may be reserved for use associated with their specific on-site assignment. For example, an on-site relay transceiver 904 may be assigned to a specific patient any may travel with the patient through a hospital (e.g., pairing with a different ventilator as the patient is paired with a different ventilator). Alternatively, a ventilator and/or relay transceiver may be assigned to a specific room, site, or wing of a hospital (e.g., imaging room or neonatal ward). In another example, a relay transceiver may be assigned to a specific clinician, doctor, or doctor support team, based on which patients or ventilators are currently assigned to the user or user team.

Region 920 represents on-site relay transceivers 904 that are paired with an on-site ventilator 902 and have a remote assignment 908. The ventilators and/or relay transceivers in this region 920 may be reserved for use associated with their specific remote assignment. For example, a relay transceiver may be assigned to a remote consultant and paired to a ventilator for viewing of ventilator data by the remote consultant. Alternatively, a relay transceiver may be assigned to a patient that is going to be transported to a different facility or a patient that was recently transported from a different facility (e.g., the relay transceiver may be paired with different ventilators as the patient is transferred from ventilator to ventilator in transit).

In non-limiting examples, relay transceivers may be assigned in the following ways: to a patient (e.g., as a patient travels or is connected to different ventilators); to a site or room (e.g., assigned to "Room 123", assigned to an MRI room, assigned to a terminal care room, assigned to a neonatal ward, assigned to a floor or region of a facility treating infectious disease, etc.); to a user (e.g., a doctor such as on-site doctor or remote consulting doctor, a clinician or care giver, a doctor support team, an educational facility, a diagnostics team, an expert consultant, etc.); or to a ventilator. In an instance where a relay transceiver is assigned to a remote doctor, the relay transceiver may be one of multiple relay transceivers paired with a single ventilator (e.g., multiple consults, or in addition to an on-site assigned relay transceiver). Additionally, as otherwise described herein, remote viewers may be limited to accessing a ventilator and/or a relay transceiver in a view-only mode.

Figure 10:
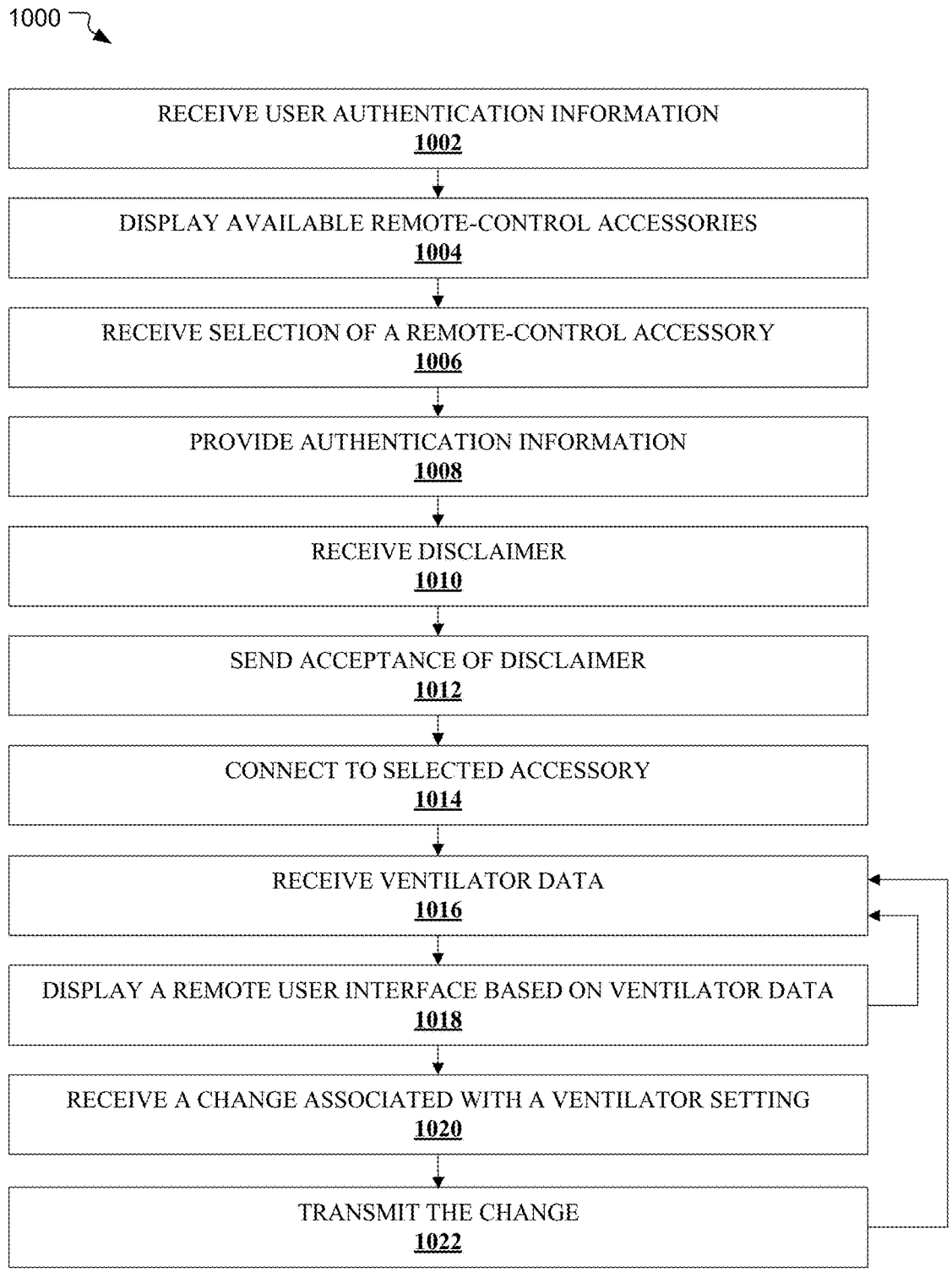
FIG. 10 depicts a method for remotely adjusting a ventilator from a perspective of a remote device.

FIG. 10 depicts a method 1000 for remotely adjusting and/or accessing a ventilator (such as ventilators 100, 202, 502, 802, 803) via a relay transceiver (e.g., relay transceivers 808, 809, 904), based on an input received at a remote device (e.g., remote devices 160, 194, 226, 520, 812, 816, 818), from a perspective of a remote device. At operation 1002, user authentication information is received. The user authentication information may be used to log in to the remote device, log in to a network of the remote device (e.g., a hospital VPN or hospital network), or otherwise verify an identity of the remote device or a user of the remote device. As otherwise described herein, the authentication information may be based on hospital security requirements and/or may utilize multi-factor authentication techniques.

At operation 1004, available relay transceivers are displayed. Relay transceivers may be indicated as available when paired with a ventilator (which may or may not be currently ventilating a patient). The available relay transceivers may be provided in a list, as icons, or otherwise organized. Relay transceivers may be named. A name of a relay transceiver may include identification information, such as an identifier associated with an assignment of the relay transceiver (e.g., Dr. J, Room 123, neonatal, etc.), or an identifier associated with a paired ventilator or the relay transceiver (e.g., IP address, serial number, etc. of the paired ventilator and/or the relay transceiver).

At operation 1006, a selection of a relay transceiver is received. For instance, a selection of an icon representing a relay transceiver may be received. A selection of a relay transceiver may cause the remote device to connect with the relay transceiver. At operation 1008, authentication information is provided to the selected relay transceiver. The authentication information may be the same or different authentication information received at operation 1002. For example, a hospital's multi-factor authentication may be used to identify a user to log in to a remote device and also act as authentication of a remote device or the user of the remote device.

At operation 1010, a disclaimer is received and/or accessed locally on the remote device. The disclaimer may include a usage agreement, setting preferences, or other warnings or information. In an example, a usage agreement is received from the selected relay transceiver every time a remote device connects to the relay transceiver. The usage agreement may require action (e.g., accept or deny) before proceeding to remote ventilator access via the relay transceiver. At operation 1012, an acceptance of the disclaimer is received by the remote device from the user and an indication of the acceptance may be sent to the selected relay transceiver.

At operation 1014, a connection to the selected relay transceiver is established. As further described herein, access permissions of the connection may include view-only permissions or view and control permissions.

At operation 1016, ventilator data is received. The ventilator data may be continuously updated. As further described herein, the ventilator data may include a video feed or successive image captures in substantially real time to replicate at least a portion of the ventilator GUI (displayed at the ventilator) at the remote user interface (on the remote device). At operation 1018, a remote user interface is displayed based on the ventilator data. The remote user interface that is replicating a portion of a live ventilator display may be associated with an overlay to recognize how a selection at the remote user interface of the remote device correlates with a selection at the live ventilator display. Additionally, the remote user interface may include one or more features described herein, including user interface elements (e.g., a virtual bezel key, a ventilator setting icon, an adjustment user interface element, etc.), subdivision into one or more sections (e.g., a selection section/panel, an adjustment section/panel, or a mode-changeable section/panel changeable to display different view modes). Operations 1016 and 1018 may repeat as required or desired (e.g., while the remote device is connected to the relay transceiver) such that the ventilator data may be used to replicate the ventilator UI in real time.

If access to the relay transceiver is a view-only mode, method 1000 may end at operation 1018. At operation 1020, a change associated with a selected ventilator setting icon is received. An increment of the change to the ventilator setting associated with the ventilator settings icon may be indicated based on an interaction with an adjustment element at the remote user interface (e.g., slide bar, an upward or downward adjustment icon, a rotatable dial, etc.). At operation 1022, the change is transmitted to the relay transceiver. The change (e.g., including the ventilator setting and an increment to adjust the ventilator setting) is associated with an update of a setting on the ventilator paired with the relay transceiver. Operations 1016 through 1022 may repeat as required or desired (e.g., while the remote device is connected to the relay transceiver) such that the ventilator data may be used to replicate the ventilator UI in real time (e.g., as ventilator settings are changed).

Figure 11:
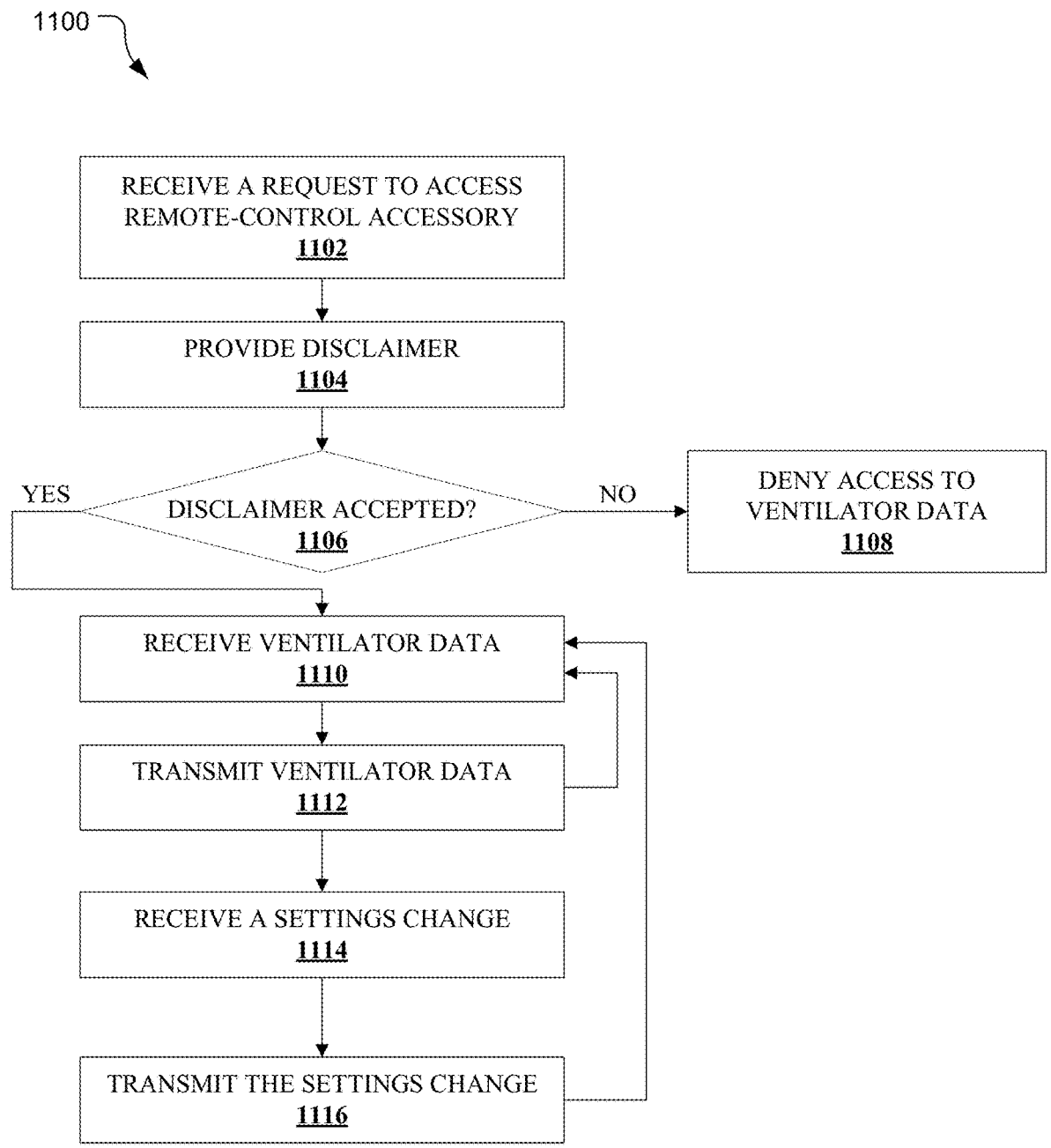
FIG. 11 depicts a method for remotely adjusting a ventilator from a perspective of a relay transceiver.

FIG. 11 depicts a method 1100 for remotely adjusting and/or accessing a ventilator (such as ventilators 100, 202, 502, 802, 803) via a relay transceiver (e.g., relay transceivers 808, 809, 904), based on an input received at a remote device (e.g., remote devices 160, 194, 226, 520, 812, 816, 818), from a perspective of a relay transceiver. At operation 1102, a request to access the relay transceiver is received. The request may be received from a remote device that communicates with the relay transceiver via a wired or wireless connection. The request to access the relay transceiver may be authenticated to verify a remote device and/or a user of the remote device requesting access.

At operation 1104, a disclaimer is provided to the remote device. The disclaimer may be similar to the disclaim described above for operation 1010 in FIG. 10. At determination 1106, it is determined if one or more portions of the disclaimer are accepted. If an acceptance is not received (e.g., the disclaimer times out or is declined at the remote device), flow proceeds as "NO" to operation 1108 where access to ventilator data (e.g., data received from a paired ventilator) is denied. Denial may prompt closing of an application on the remote device.

If, alternatively, an acceptance is received, flow proceeds as "YES" to operation 1110. At operation 1110, ventilator data is received (e.g., from the ventilator to the relay transceiver). The ventilator data may be similar to that described in operation 1016 in FIG. 10.

At operation 1112, the ventilator data is transmitted. The relay transceiver may send or forward the ventilator data to the remote device to allow the remote device to replicate the ventilator GUI. The transmission may be continuously forwarded as ventilator information is received by the relay transceiver from the ventilator. Operations 1110 and 1112 may repeat as required or desired (e.g., while the remote device is connected to the relay transceiver) to allow an application running on the remote device to display the ventilator UI in real time.

At operation 1114, a settings change is received from the remote device. The settings change may be associated with a ventilator setting and an adjustment increment to adjust a value of the ventilator setting. At operation 1116, the settings change is transmitted. The settings change is transmitted to the ventilator to update a setting of the ventilator paired with the relay transceiver. Operations 1110 through 1116 may repeat as required or desired (e.g., while the remote device is connected to the relay transceiver) such that the ventilator data may be used to replicate the ventilator UI in real time at the remote device (e.g., as ventilator settings are changed).

Figure 12:
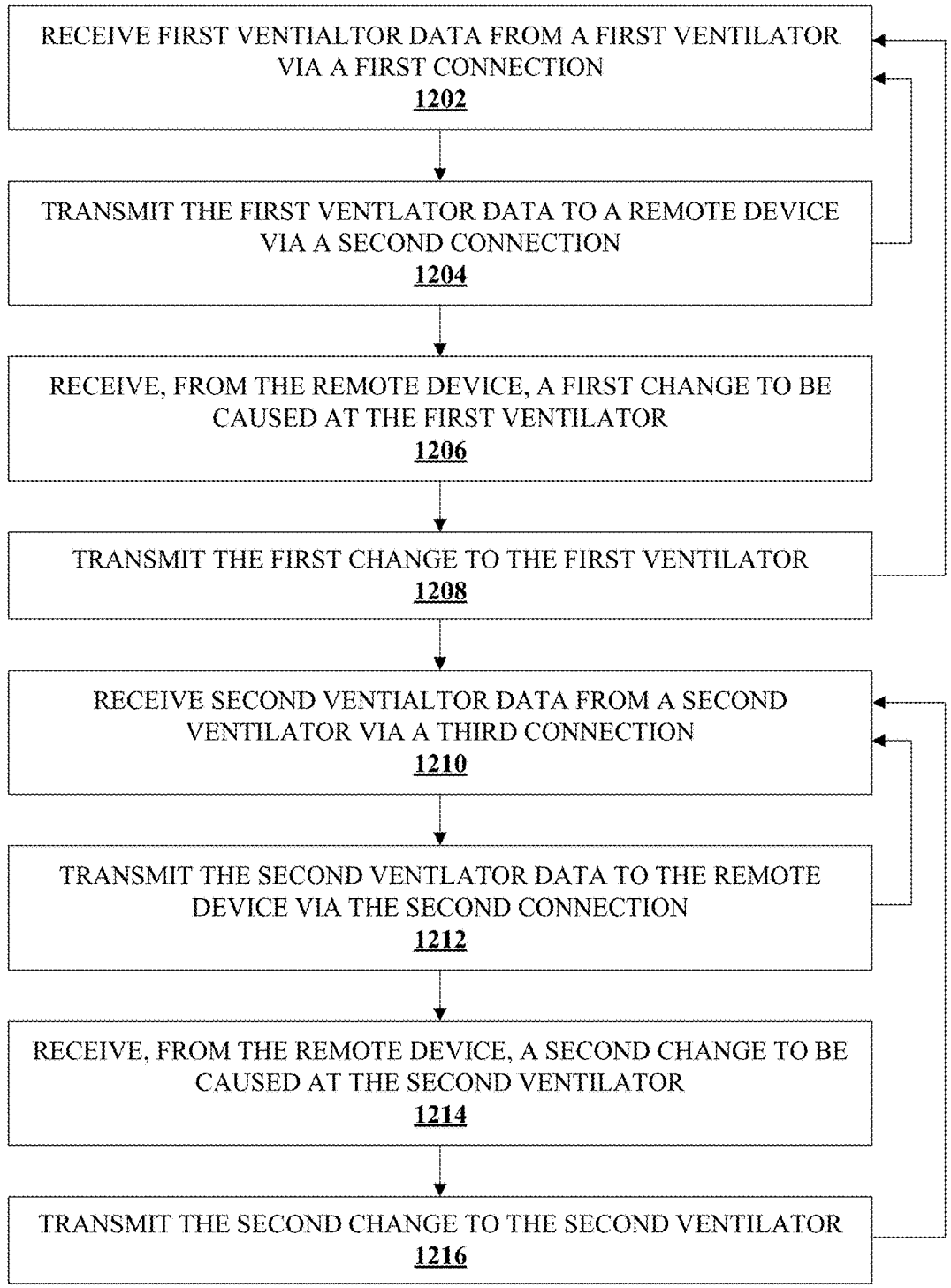
FIG. 12 depicts a method for pairing a relay transceiver with multiple ventilators.

FIG. 12 depicts a method 1200 for pairing a relay transceiver (e.g., relay transceivers 808, 809, 904) with multiple ventilators (e.g., ventilators 100, 202, 502, 802, 803). At operation 1202, first ventilator data is received from a first ventilator via a first connection. The first connection between the relay transceiver and the first ventilator may be a physical connection (e.g., a wired connection, a connection via a port on the ventilator, integrated into the ventilator, etc., as otherwise described herein). The first ventilator data may be continuously received while the first connection is established (e.g., until the relay transceiver is physically disconnected from the first ventilator). The relay transceiver may transmit a disconnection notice to the remote device when a connection between the relay transceiver and a ventilator is lost or disconnected (e.g., as may be displayed at a remote user interface of the remote device as a connect or disconnect button 708 or as information 710).

At operation 1204, the first ventilator data is transmitted to a remote device via a second connection. The second connection (the connection between the relay transceiver and the remote device) may be a wireless connection. The first ventilator data may be continuously transmitted or forwarded to the remote device while the first connection and the second connection are established (e.g., until the relay transceiver is disconnected from the first ventilator or until the remote device is disconnected from the relay transceiver).

At operation 1206, a first change, to be caused at the first ventilator, is received form the remote device. As otherwise described herein, a change (e.g., the first change) may be associated with a ventilator setting and an adjustment increment to adjust a value of the ventilator setting (e.g., by selection of a ventilator settings icon displayed at the remote device). The adjustment increment may be indicated based on an interaction with an adjustment element at the remote user interface.

At operation 1208, the first change is transmitted to the first ventilator. Transmission of the change may cause a setting of the ventilator to be adjusted by an amount indicated by the first change. For instance, upon receiving the first change or indication of the first change, the ventilator changes or adjusts the respective setting. Operations 1202-1204 and 1202-1208 may repeat as required or desired.

At operation 1210, second ventilator data is received from a second ventilator via a third connection. The third connection, between the relay transceiver and the second ventilator, may be the same or similar to the connection described in operation 1202 between the relay transceiver and the first ventilator.

To establish the first connection and/or the third connection, relay transceiver may be required or desired to be located near (e.g., in the same room) as the ventilator to which it is connected. The first ventilator and the second ventilator may be in different locations (e.g., different rooms of a hospital, different wings of a hospital, different buildings, etc.). In this instance, the relay transceiver may be in a first room when receiving the first ventilator data over the first connection and may be relocated to a second room when receiving the second ventilator data over the third connection. For instance, a clinician may unplug the relay transceiver from the first ventilator, carry the relay transceiver to the second ventilator, and plug the relay transceiver into the second ventilator. Additionally, the first connection and the third connection may be established at different times and may be mutually exclusive.

Alternatively, the relay transceiver may establish the first connection and the third connection concurrently. For instance, multiple ports of the relay transceiver may be used. A first cable from a first port of the relay transceiver may be connected to a port of the first ventilator, and a second cable from a second port of the relay transceiver may be connected to a port of the second ventilator. In an example where the first connection and the third connection are not established concurrently, the first connection may be disconnected prior to establishing the third connection and prior to receiving second ventilator data from the second ventilator at operation 1210.

At operation 1212, the second ventilator data is transmitted to the remote device via the second connection. At operation 1214, a second change, to be caused at the second ventilator, is received from the remote device. At operation 1216, the second change is transmitted to the second ventilator. Operations 1212-1216 may be the same or similar to operations 1204-1208, except relating to the third connection between the relay transceiver and the second ventilator (instead of the first connection between the relay transceiver and the first ventilator). Operations 1210-1212 and 1210-1216 may repeat as required or desired.

Figure 13:
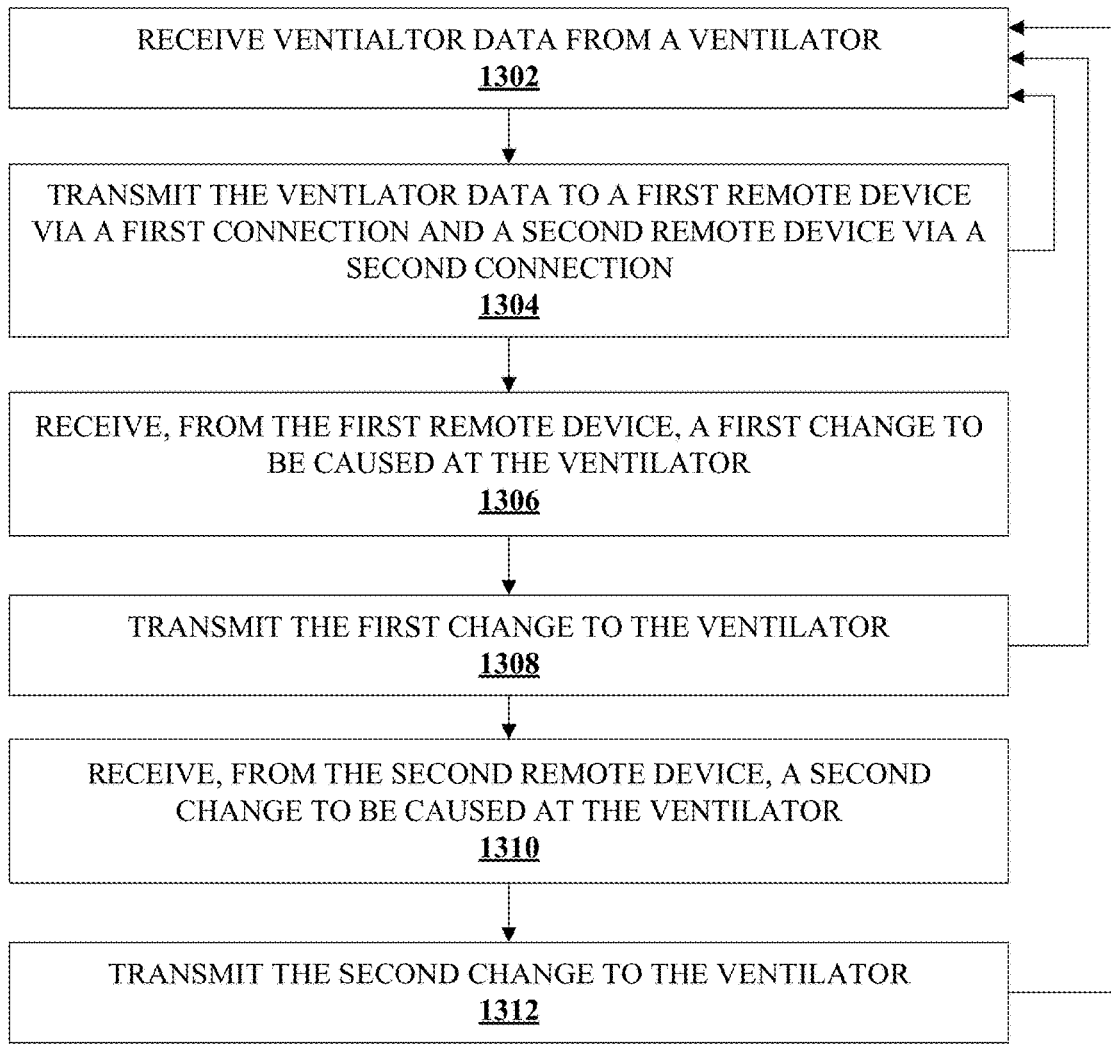
FIG. 13 depicts a method for receiving changes to be caused at a ventilator from multiple remote devices.

FIG. 13 depicts a method 1300 for receiving changes to be caused at a ventilator (e.g., ventilators 100, 202, 502, 802, 803) from multiple remote devices (e.g., remote devices 160, 194, 226, 520, 812, 816, 818). At operation 1302, ventilator data is received from a ventilator. The ventilator data may be received over a connection between a relay transceiver and the ventilator. The connection between the relay transceiver and the ventilator may be a physical connection (e.g., a wired connection, a connection via a port on the ventilator, integrated into the ventilator, etc.). The ventilator data may be continuously received while the connection between the relay transceiver and the ventilator is established (e.g., until the relay transceiver is disconnected from the ventilator).

At operation 1304, the ventilator data is transmitted to a first remote device via a first connection and a second remote device via a second connection. The first connection, the connection between the relay transceiver and the first remote device, and/or the second connection, the connection between the relay transceiver and the second remote device, may be wireless connections. The ventilator data may be continuously transmitted or forwarded to the first remote device and the second remote device as it is received from the ventilator. The first remote device and/or the second remote device may be located outside of a room in which the ventilator is located. Operations 1302-1304 may repeat as required or desired.

At operation 1306, a first change to be caused at the ventilator is received from the first remote device. As further described herein, a change (e.g., the first change) may be associated with a ventilator setting (associated with a ventilator settings icon at the remote device) and an adjustment increment (associated with an adjustment element at the remote device) to adjust a value of the ventilator setting.

At operation 1308, the first change is transmitted to the ventilator. Transmission of the first change may cause a first setting of the ventilator to be adjusted by an amount indicated by the first change. Operations 1302-1308 may repeat as required or desired.

At operation 1310, a second change to be caused at the ventilator is received from the second remote device. Similar to the first change described in operation 1306, the second change may be associated with a ventilator setting and an adjustment increment to adjust a value of the ventilator setting. The first change and the second change may be associated with different ventilator settings or the same ventilator setting. Additionally, the first change and the second change may be associated with a same or different adjustment increment (e.g., a same change to a value of a setting). For example, a first change may be a +0.1 $cmH_2O$ adjustment increment to PEEP and the second change may also be a +0.1 $cmH_2O$ adjustment increment to PEEP, resulting in a total change of +0.2 $cmH_2O$ to the PEEP ventilation setting. In another example, a first change may be a +0.1 $cmH_2O$ adjustment increment to PEEP and a second change may be a −2 f/mm adjustment increment to respiratory rate.

Adjustments to ventilator settings (e.g., a first change and a second change) may be restricted. For example, the second change may be prevented from being received at the relay transceiver (and/or prevented from being received at a user interface of the second remote device) until after receiving and/or transmitting, or between receiving and transmitting, the first change (e.g., while the first change is being caused at the ventilator). Additionally or alternatively, local control of the ventilator (e.g., at the user interface of the ventilator itself) may be prevented until after receiving and/or transmitting, or between receiving and transmitting, the first change. The local control at the ventilator or one or more remote devices may be prioritized for causing changes to ventilator settings. For example, the local control may override any incoming changes from remote devices (e.g., the first remote device or the second remote device). In another example, a prioritized remote device may override any changes to ventilator settings (e.g., local changes or changes from other remote devices). In another example, changes from remote devices may be prevented for a lockout period (e.g., a specified period of time, such as 10 seconds, 30 seconds, 1 minute, 2 minutes, 5 minutes, 10 minutes, etc.) when local control of the ventilator is detected (e.g., by the relay transceiver determining a change in the ventilator data and/or a change in one or more values of a ventilator setting). If changes are not currently available at a remote device, the remote device may be designated in a view-only mode (e.g., have view-only access or permission to the ventilator data). If changes are permitted by the remote device, the remote device, then the remote device may be operating in a view and control mode (e.g., have view and control access or permission to the ventilator data).

At operation 1312, the second change is transmitted to the ventilator. Transmission of the second change may cause a second setting of the ventilator (e.g., which may be the same as or different from the first setting associated with the first change) to be adjusted by an amount indicated by the second change. Operations 1302-1312 may repeat as required or desired. Although two remote devices are provided in the example method 1300, any number of remote devices is appreciated.

Those skilled in the art will recognize that the methods and systems of the present disclosure may be implemented in many manners and as such are not to be limited by the foregoing aspects and examples. In other words, functional elements being performed by a single or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, myriad software/hardware/firmware combinations are possible in achieving the functions, features, interfaces, and preferences described herein. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

In an aspect, the present technology relates to a system for remotely adjusting a ventilator. The system includes a display, a processor, and memory storing instructions that, when executed by the processor, cause the system to perform a set of operations. The set of operations include displaying, on the display, a ventilator user interface comprising an icon associated with a ventilation setting. The set of operations further include receiving, from a remote device, selection data comprising position information and selection information of a time-varying user input. Based on the selection data, the set of operations include determining a selection of the icon. The set of operations additionally includes displaying, on the ventilator user interface a value associated with the selected icon. Thereafter, the set of operations includes determining, based on the selection data, a change in the value associated with the selected icon. Additionally, the set of operations includes displaying, on the ventilator user interface, the change in the value and updating the ventilation setting based on the change in the value.

For example, the set of operations further includes sending display information to a replicate display device to replicate a portion of the ventilator user interface. In another example, the replicate display device is the remote device. In a further example, the replicate display device is different from the remote device and is non-interactive. In yet another example, an intermediate device relays the selection data from the remote device to the ventilator. In still a further example, the system further includes a physical input component configured to adjust the value. In another example, the physical input component is a rotatable dial, and the change in the value is associated with an angle of rotation of the rotatable dial. In a further example, the set of operations further includes receiving, from the remote device, adjustment data associated with the change in the value.

In another example, a method for remotely adjusting a ventilator is provided. The method includes displaying, on a remote device, a remote user interface and receiving, at the remote user interface, a time-varying user input comprising an input position and an input selection. The method further includes sending, to the ventilator, selection data based on the input position and the input selection and receiving, from the ventilator, a selection indication of a selected ventilator icon associated with the selection data. Thereafter, the method includes receiving, from the ventilator, a change indication of a change in a value associated with the selected ventilator icon.

In examples, the remote user interface includes a virtual trackpad. In another example, the method further includes receiving, from the ventilator, display data comprising display information to replicate a portion of the ventilator user interface. In a further example, the remote user interface includes the portion of the ventilator user interface and a virtual trackpad, the portion of the ventilator user interface comprising a local position indicator. In yet another example, the method further includes receiving, at the remote user interface, an adjustment input associated with the selected ventilator icon, wherein the remote user interface comprises a remote adjustment element and the adjustment input is based on the time-varying user input at the remote adjustment element. In still a further example, the remote adjustment element is a virtual rotatable dial capable of receiving the adjustment input. In another example, the virtual rotatable dial is associated with a physical rotatable dial on the ventilator. In yet another example, a position of the remote adjustment element is associated with a non-selectable region of a corresponding ventilator user interface. In a further example, the method further includes enabling the remote adjustment element based on the selection indication. In another example, the method further includes receiving, from the ventilator, a de-selection indication of the selected ventilator control element; and disabling the remote adjustment element. In a further example, the method further includes displaying the selection indication on the remote user interface.

In a further example, a method for remotely adjusting a ventilator is provided. The method includes displaying, by the ventilator, a ventilator user interface comprising a ventilator control element associated with a ventilation setting and displaying, on a remote device, a remote user interface. The method further includes receiving, at the remote device, a time-varying user input at the remote user interface comprising an input position and an input selection and sending, from the remote device to the ventilator, selection data based on the selection input. Additionally, the method includes receiving, at the ventilator, the selection data from the remote device and determining, by the ventilator, a selection of the ventilator control element, based on the selection data. The method includes displaying, by the ventilator on the ventilator user interface a value associated with the selected ventilator control element. Thereafter, the method includes determining, by the ventilator, a change in a value associated with the selected ventilator control element. The method further includes displaying, by the ventilator on the ventilator user interface, the change in the value; and updating the ventilation setting based on the change in the value.

In another example, a method for remotely accessing a medical ventilator is provided. The method includes connecting, via a wired or wireless connection, a remote computing device to a ventilator, the ventilator having a ventilator display; and providing, on the remote computing device, a view of the ventilator display. The method further includes tracking, on the remote computing device, cursor movement and a cursor activation. Additionally, the method includes displaying, on the remote computing device, the cursor movement overlaid on the view of the ventilator display; and transmitting the cursor activation to the ventilator, via the wired or wireless connection.

In an example, the set of operations further includes: receiving updated ventilator data from the relay transceiver associated with the settings change caused at the ventilator; and updating the remote user interface based on the updated ventilator data. In another example, the set of operations further comprise: displaying, on the display, a plurality of relay icons corresponding to a plurality of relay transceivers; receiving a selection of a particular relay icon; and based on the received selection of the particular relay icon, establishing a connection with a particular relay transceiver corresponding to the particular relay icon. In a further example, the system is located outside a of a room in which the particular relay transceiver and the ventilator are located. In yet another example, the ventilator data is received over a wireless network of a hospital. In still a further example, the remote ventilator user interface includes at least one ventilator settings icon, and wherein the selected ventilator setting is the at least one ventilator settings icon. In another example, the remote interface includes a virtual bezel key representing at least one physical bezel key on the ventilator, and wherein the selected ventilator setting is the virtual bezel key. In a further example, the remote user interface includes an adjustment element, and wherein the settings change is defined by a received interaction with the adjustment element. In yet another example, the adjustment element is a slide bar. In still a further example, the remote user interface comprises three panels: a changeable panel including the remote ventilator user interface; a selection panel including the virtual bezel key; and an adjustment panel including the adjustment element.

In another aspect, a relay transceiver for remotely adjusting a ventilator is disclosed. The relay transceiver system includes a processor; and memory storing instructions that, when executed by the processor, cause the system to perform a set of operations. The set of operations includes: receiving a request, from a remote device over a wireless connection between the remote device and the relay transceiver, to access ventilator data of a ventilator; and receiving the ventilator data from the ventilator over a wired connection between the ventilator and the relay transceiver. The set of operations further includes transmitting the ventilator data to the remote device over the wireless connection, the ventilator data causing a portion of the ventilator user interface to be replicated at the remote user interface. Additionally, the set of operations includes receiving, from the remote device over the wireless connection, a settings change of the at least one adjustable ventilator setting; and transmitting the settings change to the ventilator over the wired connection.

In an example, the wireless connection between the remote device and the relay transceiver is over a hospital network. In another example, the wired connection between the ventilator and the relay transceiver is established with at least one of: an HDMI-to-USB adapter; a dongle; a self-supported HDMI connection; and a smart cable. In a further example, the set of operations further includes: receiving a patient video feed from a camera; and transmitting the patient video feed to the remote device for display at the remote user interface. In yet another example, the ventilator data includes a video of the ventilator user interface. In still a further example, the at least one adjustable ventilator setting is associated with one of: a physical bezel key on the ventilator; and a ventilator user interface element on the ventilator user interface. In another example, the at least one adjustable ventilator setting associated with the physical bezel key is one of: a display brightness; a display lock; an alarm volume; a manual inspiration; an inspiratory pause; an expiratory pause; an alarm reset; and an audio pause. In a further example, the at least one adjustable ventilator setting associated with the ventilator user interface element is one of: an inhalation flow; a respiratory rate; a tidal volume; and a positive end-expiratory pressure (PEEP). In yet another example, the set of operations further includes in response to receiving the request to access ventilator data of the ventilator, transmitting a usage agreement to the remote device over the wireless connection; and receiving an acceptance of the usage agreement from the remote device over the wireless connection.

In a further aspect, a method for remotely accessing a ventilator is disclosed. The method includes receiving ventilator data from a relay transceiver communicatively coupled to a ventilator. Based on the ventilator data, the method includes displaying a remote user interface including a remote ventilator user interface replicating at least a portion of a ventilator user interface of the ventilator. Additionally, the method includes receiving, at the remote user interface, a selection of a ventilator setting; receiving, at the remote user interface, a settings change to the selected ventilator setting; and transmitting the settings change to the relay transceiver.

In another aspect, a method for pairing a relay transceiver with a first ventilator and a second ventilator is described. The method includes: receiving first ventilator data from a first ventilator over a first wired connection between the relay transceiver and the first ventilator; and transmitting the first ventilator data to a remote device over a wireless connection between the relay transceiver and the remote device. Additionally, the method includes receiving, from the remote device, a first change to be caused at the first ventilator; transmitting the first change to the first ventilator; and receiving second ventilator data from a second ventilator over a second wired connection between the relay transceiver and the second ventilator. The method further includes transmitting the second ventilator data to the remote device over the wireless connection; receiving, from the remote device, a second change to be caused at the second ventilator; and transmitting the second change to the second ventilator.

In an example, the first wired connection and the second wired connection are not concurrently established. In another example, the relay transceiver is physically disconnected from the first ventilator prior to the second wired connection being established. In a further example, the method further includes: when receiving the first ventilator data, the relay transceiver is removably attached to a physical port of the first ventilator accessible outside of a housing of the first ventilator; and when receiving the second ventilator data, the relay transceiver is removably attached to a physical port of the second ventilator accessible outside of a housing of the second ventilator. In yet another example, when receiving the second ventilator data, the relay transceiver is not attached to the physical port of the first ventilator. In still a further example, the first ventilator and the second ventilator are in different rooms of a hospital. In another example, the first wired connection is contained inside a room of a hospital and the remote device is outside of the room. In a further example, transmitting the first change to the first ventilator causes a settings change at the first ventilator. In yet another example, the method further includes transmitting a disconnection notice to the remote device. In still a further example, the first ventilator data includes video data.

In a further aspect, a method for receiving settings changes from multiple remote devices at a relay transceiver is disclosed. The method includes receiving ventilator data from a ventilator over a wired connection; and transmitting the ventilator data to a first remote device over a first wireless connection and a second remote device over a second wireless connection. The method further includes receiving, from the first remote device, a first change to be caused at the ventilator; and transmitting the first change to the ventilator. Additionally, the method includes receiving, from the second remote device, a second change to be caused at the ventilator; and transmitting the second change to the ventilator.

In an example, the first wireless connection and the second wireless connection are over a hospital network. In another example, the ventilator data includes video data associated with the ventilator. In a further example, the method further includes: receiving a patient video feed from a camera; and transmitting the patient video feed to the first remote device. In yet another example, the first remote device and the second remote device are located outside of a room in which the ventilator is located. In still a further example, the ventilator data is continuously received and transmitted. In another example, the second change is prevented from being received until after transmitting the first change. In a further example, changes from the first remote device and the second remote device are prevented for a lockout period when local control of the ventilator is detected. In yet another example, the method further includes transmitting the ventilator data to a third remote device while preventing any changes to be received from the third remote device. In still a further example, the first remote device has view and control access to the ventilator data and the third remote device has view-only access to the ventilator data.

What is claimed is:

1. A relay transceiver for remotely adjusting a ventilator, the relay transceiver comprising:
 a processor;
 memory storing instructions that, when executed by the processor, cause the relay transceiver to perform a set of operations comprising:
  receiving a first request, from a remote device, over a wireless connection between the remote device and the relay transceiver, to access ventilator data of a first ventilator;
  receiving the ventilator data from the first ventilator over a first wired connection between the first ventilator and the relay transceiver;
  transmitting the ventilator data to the remote device over the wireless connection to cause a portion of a ventilator user interface of the first ventilator to be replicated at the remote device;
  receiving a second request, from the remote device over the wireless connection between the remote device and the relay transceiver, to access ventilator data of a second ventilator connected to the relay transceiver via a second wired connection; and in response to the second request, transmitting the ventilator data of the second ventilator to the remote device over the wireless connection to cause a portion of a ventilator user interface of the second ventilator to be replicated at the remote device.

2. The relay transceiver of claim 1, wherein the remote device is a first remote device, and wherein the set of operations further comprises:
receiving a third request, from a second remote device over a wireless connection between the second remote device and the relay transceiver, to access the ventilator data of the first ventilator;
based on the third request, authenticating the second remote device; and
in response to authenticating the second remote device, transmitting the ventilator data of the first ventilator to the second remote device while transmitting the ventilator data of the first ventilator to the first remote device.

3. The relay transceiver of claim 1, wherein the set of operations further comprises receiving an assignment for the relay transceiver to a user.

4. The relay transceiver of claim 3, wherein the remote device is a first remote device, and wherein the set of operations further comprises:
receiving a third request, from a second remote device over a wireless connection between the second remote device and the relay transceiver, to access the ventilator data of the first ventilator;
determining that third request is not valid, based on the assignment; and
denying access of the second remote device to the ventilator data of the first ventilator.

5. The relay transceiver of claim 4, wherein the assignment of the relay transceiver is to a user group including the user.

6. The relay transceiver of claim 5, wherein the user group is a team of medical professionals on-site with the relay transceiver.

7. The relay transceiver of claim 1, wherein the ventilator data of the first ventilator includes a video feed of at least a portion of the ventilator user interface of the first ventilator.

8. A method for remotely adjusting a ventilator, the method comprising:
receiving, at a relay transceiver from a remote device over a wireless connection, a first request to access ventilator data of a first ventilator;
in response to the first request, transmitting, from the relay transceiver to the remote device in real time, the ventilator data from the first ventilator to cause a portion of a ventilator user interface of the first ventilator to be replicated at a remote user interface of the remote device;
receiving, at the relay transceiver from the remote device, a second request to access ventilator data of a second ventilator; and
in response to the second request, transmitting, from the relay transceiver to the remote device over the wireless connection, the ventilator data of the second ventilator to cause a portion of a ventilator user interface of the second ventilator to be replicated at the remote user interface of the remote device.

9. The method of claim 8, further comprising:
receiving, at a relay transceiver, an assignment for the relay transceiver to a user; and
authenticating the remote device at the relay transceiver, wherein authenticating the remote device includes determining that the remote device is accessed by the user.

10. The method of claim 9, wherein the assignment of the relay transceiver is to a user group including the user.

11. The method of claim 9, wherein the remote device is a first remote device, and the method further comprises:
receiving a third request, from a second remote device over a wireless connection between the second remote device and the relay transceiver, to access the ventilator data of the first ventilator;
determining that third request is not valid, based on the assignment; and
denying access of the second remote device to the ventilator data of the first ventilator.

12. The method of claim 8, wherein the remote user interface includes a virtual bezel key representing at least one physical bezel key on the first ventilator.

13. The method of claim 8, wherein the wireless connection between the remote device and the relay transceiver is over a hospital network.

14. The method of claim 8, wherein the ventilator data of the first ventilator includes a video feed of at least a portion of the ventilator user interface of the first ventilator.

15. The method of claim 8, wherein the remote device is a first remote device, and wherein the method further comprises:
receiving a third request, from a second remote device over a wireless connection between the second remote device and the relay transceiver, to access the ventilator data of the first ventilator;
based on the third request, authenticating the second remote device; and
in response to authenticating the second remote device, transmitting the ventilator data of the first ventilator to the second remote device while transmitting the ventilator data of the first ventilator to the first remote device.

16. A ventilation system comprising:
a first ventilator;
a second ventilator; and
a relay transceiver for remotely adjusting a ventilator, the relay transceiver comprising:
a processor;
memory storing instructions that, when executed by the processor, cause the relay transceiver to perform a set of operations comprising:
receiving a first request, from a remote device, over a wireless connection between the remote device and the relay transceiver, to access ventilator data of the first ventilator;
receiving the ventilator data from the first ventilator over a first wired connection between the first ventilator and the relay transceiver;
transmitting the ventilator data to the remote device over the wireless connection to cause a portion of a ventilator user interface of the first ventilator to be replicated at the remote device;
receiving a second request, from the remote device over the wireless connection between the remote device and the relay transceiver, to access ventilator data of the second ventilator connected to the relay transceiver via a second wired connection; and
in response to the second request, transmitting the ventilator data of the second ventilator to the remote device over the wireless connection to cause a portion of a ventilator user interface of the second ventilator to be replicated at the remote device.

17. The ventilation system of claim 16, wherein the operations further comprise:
   receiving, at a relay transceiver, an assignment for the relay transceiver to a user; and
   authenticating the remote device at the relay transceiver, wherein authenticating the remote device includes determining that the remote device is accessed by the user.

18. The ventilation system of claim 17, wherein the assignment of the relay transceiver is to a user group including the user.

19. The ventilation system of claim 16, wherein the ventilator data of the first ventilator includes a video feed of at least a portion of the ventilator user interface of the first ventilator.

20. The ventilation system of claim 19, wherein the remote interface includes a virtual bezel key representing at least one physical bezel key on the first ventilator.

* * * * *